US011351244B2

(12) United States Patent
Calvert et al.

(10) Patent No.: US 11,351,244 B2
(45) Date of Patent: Jun. 7, 2022

(54) EFFECTIVE VACCINATION AGAINST PORCINE REPRODUCTIVE AND RESPIRATORY SYNDROME (PRRS) VIRUS PRIOR TO WEANING

(71) Applicant: Zoetis Services LLC, Parsippany, NJ (US)

(72) Inventors: Jay Gregory Calvert, Otsego, MI (US); Robert G. Ankenbauer, Portage, MI (US); Jacqueline Gayle Marx, Portage, MI (US); Douglas S. Pearce, Kalamazoo, MI (US); Marcia L. Keith, Plainwell, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 16/822,830

(22) Filed: Mar. 18, 2020

(65) Prior Publication Data

US 2020/0215181 A1 Jul. 9, 2020

Related U.S. Application Data

(63) Continuation of application No. 13/895,564, filed on May 16, 2013, now Pat. No. 10,610,581.

(60) Provisional application No. 61/648,461, filed on May 17, 2012.

(51) Int. Cl.

| | |
|---|---|
| *A61K 39/12* | (2006.01) |
| *C12N 7/00* | (2006.01) |
| *A61K 39/00* | (2006.01) |

(52) U.S. Cl.

CPC ................ *A61K 39/12* (2013.01); *C12N 7/00* (2013.01); *A61K 2039/5254* (2013.01); *A61K 2039/53* (2013.01); *A61K 2039/55* (2013.01); *A61K 2039/552* (2013.01); *C12N 2770/10034* (2013.01); *C12N 2770/10064* (2013.01)

(58) Field of Classification Search

None

See application file for complete search history.

(56) References Cited

U.S. PATENT DOCUMENTS

| | | | |
|---|---|---|---|
| 3,137,631 | A | 6/1964 | Soloway |
| 3,519,710 | A | 7/1970 | Bass |
| 3,959,457 | A | 5/1976 | Speaker et al. |
| 4,016,100 | A | 4/1977 | Suzuki et al. |
| 4,205,060 | A | 5/1980 | Monsimer et al. |
| 4,452,747 | A | 6/1984 | Gersonde et al. |
| 4,606,940 | A | 8/1986 | Frank et al. |
| 4,744,933 | A | 5/1988 | Rha et al. |
| 4,921,706 | A | 5/1990 | Roberts et al. |
| 4,927,637 | A | 5/1990 | Morano et al. |
| 4,944,948 | A | 7/1990 | Uster et al. |
| 5,008,050 | A | 4/1991 | Cullis et al. |
| 5,009,956 | A | 4/1991 | Baumann |
| 5,132,117 | A | 7/1992 | Speaker et al. |
| 5,789,543 | A | 8/1998 | Ingham et al. |
| 5,866,401 | A | 2/1999 | Hesse |
| 5,951,977 | A | 9/1999 | Nisbet et al. |
| 5,998,601 | A | 12/1999 | Murtaugh et al. |
| 6,015,686 | A | 1/2000 | Dubensky, Jr. et al. |
| 6,033,886 | A | 3/2000 | Conzelmann |
| 6,042,830 | A | 3/2000 | Chladel et al. |
| 6,268,199 | B1 | 7/2001 | Meulenberg et al. |
| 6,500,662 | B1 | 12/2002 | Calvert et al. |
| 6,943,152 | B1 | 9/2005 | Audonnet et al. |
| 7,132,106 | B2 | 11/2006 | Calvert et al. |
| 7,232,680 | B2 | 6/2007 | Calvert et al. |
| 7,473,428 | B2 | 1/2009 | Johnson et al. |
| 7,618,797 | B2 | 11/2009 | Calvert et al. |
| 7,691,389 | B2 | 4/2010 | Calvert et al. |
| 7,754,464 | B2 | 7/2010 | Calvert et al. |
| 8,058,050 | B2 | 11/2011 | Calvert et al. |
| 8,110,390 | B2 | 2/2012 | Faaberg et al. |
| 8,420,373 | B2 | 4/2013 | Delputte et al. |
| 8,481,705 | B2 | 7/2013 | Calvert et al. |
| 8,492,132 | B2 | 7/2013 | Calvert et al. |
| 8,609,827 | B2 | 12/2013 | Calvert et al. |
| 9,102,912 | B2 | 8/2015 | Calvert et al. |
| 9,566,324 | B2 | 2/2017 | Calvert et al. |
| 2004/0087521 | A1 | 5/2004 | Donnelly et al. |
| 2011/0177118 | A1 | 7/2011 | Zuckermann |
| 2012/0213810 | A1 | 8/2012 | Burgard |

(Continued)

FOREIGN PATENT DOCUMENTS

| | | |
|---|---|---|
| EP | 0839912 A1 | 5/1998 |
| JP | 9313188 | 12/1997 |

(Continued)

OTHER PUBLICATIONS

Alignment of SEQ ID No. 6 with U.S. Pat. No. 6,500,662—SEQ ID Dec. 1, 1999.*

U.S. Appl. No. 60/694,021, Han et al., filed Jun. 24, 2005

Ishizeki, S. et al, Jul. 18-21, 2010, "Evaluation of the efficacy of PRRSV modified live vaccine in one-day old piglets," Poster Presentations, p. 232, Proceedings of the 21st IPVS Congress, Vancouver, Canada.

Markowska-Daniel, I. et al., 2011, "The influence of age and maternal antibodies on the postvaccinal response against swine influenza viruses in pigs," Veterinary Immunology and Immunopathology, 142:81-86.

(Continued)

*Primary Examiner* — Shanon A. Foley

(74) *Attorney, Agent, or Firm* — Vyacheslav Vasilyev

(57) ABSTRACT

The invention provides isolated polynucleotide molecules that comprise a DNA sequence encoding an infectious RNA sequence encoding a genetically-modified North American PRRS virus, methods to make it and related polypeptides, polynucleotides, and various components. Vaccines comprising the genetically modified virus and polynucleotides and a diagnostic kit to distinguish between naturally infected and vaccinated animals are also provided.

5 Claims, 8 Drawing Sheets

Specification includes a Sequence Listing.

(56) References Cited

U.S. PATENT DOCUMENTS

| | | | |
|---|---|---|---|
| 2013/0309263 | A1 | 11/2013 | Calvert et al. |
| 2014/0186395 | A1 | 7/2014 | Delputte et al. |
| 2017/0136117 | A1 | 5/2017 | Calvert et al. |
| 2020/0197507 | A1* | 6/2020 | Calvert .................. A61K 39/12 |

FOREIGN PATENT DOCUMENTS

| | | |
|---|---|---|
| WO | WO 92/21375 | 12/1992 |
| WO | WO 93/03760 | 3/1993 |
| WO | WO 96/04010 A1 | 2/1996 |
| WO | WO 96/06619 | 3/1996 |
| WO | WO 95/28227 | 10/1996 |
| WO | WO 96/40932 | 12/1996 |
| WO | WO 98/55626 | 12/1998 |
| WO | WO 2007/002321 A2 | 1/2007 |
| WO | WO 2012/063212 A1 | 5/2012 |

OTHER PUBLICATIONS

O'Neill, K. et al., 2012, "Use of commercial subunit and chimeric vaccines in 5-day-old piglets is effective in protecting from PCV2 viremia and PCVAD in a PCV2, PPV and PRRSV triple challenge model," American Association of Swine Veterinarians Annual Meeting, p. 43.

Rossow, K. D., 1998, "Porcine reproductive and respiratory syndrome," Veterinary Pathology, 35: 1-20.

Butler, J. E., D. H. Francis, J. Freeling, P. Weber and A. M. Krieg (2005). "Antibody repertoire development in fetal and neonatal piglets. IX. Three pathogen-associated molecular patterns act synergistically to allow germfree piglets to respond to type 2 thymus-independent and thymus-dependent antigens." Journal of Immunology (Baltimore, Md.: 1950) 175: 6772-6785.

Butler, J. E. and M. E. Kehrle (2005). Immunoglobulins and immunocytes in the mammary gland and its secretions. Mucosal Immunology. J. Mestecky, M. E. Lamm, W. Strober et al., Academic Press. 2: 1763-1793.

Butler, J. E., M. Sinkora, N. Wertz, W. Holtmeier and C. D. Lemke (2006). "Development of the neonatal B and T cell repertoire in swine: implications for comparative and veterinary immunology." Veterinary Research 37: 417-441.

Hammerberg, C., G. G. Schurig and D. L. Ochs (1989). "Immunodeficiency in young pigs." American journal of veterinary research (USA)(6): 868.

Hurley, D. J. (2004). Neonatal immune development in swine management. American Association of Swine Veterinarians, Des Moines, Iowa.

Kumar, A., A. N. Vlasova, Z. Liu, K. S. Chattha, S. Kandasamy, M. Esseili, X. L. Zhang, G. Rajashekara and L. J. Saif (2014). "In vivo gut transcriptome responses to Lactobacillus rhamnosus GG and Lactobacillus acidophilus in neonatal gnotobiotic piglets." Gut Microbes, 5: 152-164.

Lemke, C. D., J. S. Haynes, R. Spaete, D. Adolphson, A. Vorwald, K. Lager and J. E. Butler (2004). "Lymphoid hyperplasia resulting in immune dysregulation is caused by porcine reproductive and respiratory syndrome virus infection in neonatal pigs." Journal of Immunology (Baltimore, Md.: 1950) 172: 1916-1925.

Roth, J. A. (1999). The immune system. Diseases of Swine. B. E. Straw, S. D'Allaire, W. L. Mengeling and D. J. Taylor. Ames, Iowa, Iowa State Press: 799-820.

Sun, X. Z., N. Wertz, K. L. Lager, G. Tobin and J. E. Butler (2012). "Antibody repertoire development in fetal and neonatal piglets. XXIII: fetal piglets infected with a vaccine strain of PRRS virus display the same immune dysregulation seen in isolator piglets." Vaccine, 30: 3646-3652.

Zeidler, R. B. and H. D. Kim (1985). "Phagocytosis, chemiluminescence, and cell volume of alveolar macrophages from neonatal and adult pigs." Journal of Leukocyte Biology, 37: 29-43.

Ausubel, et al., "Current Protocols in Molecular Biology," Greene Publishing Associates & Wiley Interscience, NY (1989).

Allende, R ,et al., EMBL online database, AF046869 PRRS virus 16244B, complete genome Oct. 21, 1998.

Chasin, M., et al., "Biodegradable Polymers as Drug Delivery Systems," Drugs and the Pharmaceutical Sciences, vol. 45 (1990).

Coligan, JE., et al, Curent Protocols in Immunology John Wiley & Sons, Inc. (1998).

Collins, J.E., et al., "Isolation of swine infertility and respiratory syndrome virus (isolate ATCC VR.23 2) in North America and experimental reproduction of the disease in gnotobiotic pigs," J. Vet. Diagn. Invest., 4:117-126 (1992).

Den Boon JA, et al., J. Virol, 65(6):2910-2920 (1991).

Domb, A., et al., "Polymers for Advanced Technologies," 3:279-292(1992).

Erlich, "PCR Technology," Academic Press, Inc. 1992.

Enjuanes et al., Journal of Biotechnology 88:183-203, 2001.

Innis, et al., "PCR Strategies", Academic Press, Inc. (1995).

Kim, H.S., et al., "Enhanced replication of porcine reproductive and respiratory syndrome (PRRS) virus in a homogeneous subpopulation of MA-104 cell line,"Arch Virol., 133:477-483 (1993).

Kwang, J., et al., "Cloning, expression, and sequence analysis of the ORF4 gene of the porcine reproductive and respiratory syndrome virus MN-Ib" Journal Bet. Diagn. Invest. 6:293-296 (1994).

Kreutz, LC. "Cellular membrane factors are the major determinants of porcine reproductive and respiratory syndrome virus tropism," Virus Research 53:121-128, 1998.

Mardassi, H., 1995., Arch. Virol. 140: 1405-1418.

Meulenberg, J.J.M. et al., "Lelystad Virus, the Causative Agent of Porcine Epidemic Abortion and Respiratory Syndrome (PEARS), is Related to LdV and EAV," Virology, 192:62-72(1993).

Murtaugh, MP et al., "Comparison of the structural protein coding sequences of the VR-2332 and Lelystad vims strains of the PRRS virus,"Arch Virol 40:1 pp. 1451-1460 (1995).

Meng, X.J. et al., "Molecular cloning and nucleotide sequencing of the 3'-terminal genomic RNA of the porcine reproductive and respiratory syndrome virus," J. Gen. Virol., 1795-1801(1994).

Meulenberg, J.J.M. et al., Journal of Virology 72, 380-387 (1988).

Murtaugh, EMBL online database, U87392. PRRS virus strain VR-2332 complete genome, Jan. 8, 1998.

Nelson, CJ, et al, GenBank, AF066183, Porcine reproductive and respiratory syndrome vims Resp PRRS MLV, complete genome, May 15, 1998.

Remington, "Pharmaceutical Science," 18th ed. Mack Publishing (1990).

Sambrook, et al., "Molecular Cloning: A Laboratory manual" 2ed., Cold Spring Harbor Laboratory Press, Cold Spring Harbor NY (1989).

Snijder, E.J. et al., "The molecula biology of ariteriviruses," Journal of General Virology, 79:961-979 (1998).

Suarez. P. et al., "Phylogenetic relationships of European strains of porcine reproductive and respiratory syndrome virus (PRRSV) inferred from DNA sequences of putative ORF-5 and ORF-7 genes," Virus Research, 42:159-165(1996).

Terpstra, C. et al., Experimental reproduction of porcine epidemic abortion and respiratory syndrome (mystery swine disease) by infection with Lelystad virus: Koch's postulates fulfilled. Vet. Quart., 13:131-136 (1991).

Van Dinten LC., et al., An infectious arterivirus cDNA clone: identification of a replicase point mutation, which abolishes discontinuous mRNA transcription. Proceedings of the National Academy of Science USA 94: 991-996, (1997).

Wensvoort, G et al., Mystery swine disease in the Netherlands: the isolation of Lelystad virus, Vet Quart., 13:121-130(1991).

Yang SX et al., Comparative sequence analysis of open reading frames 2 to 7 of the modified live vaccine virus and other North American isolates of the porcine reproductive and respiratory syndrome virus, Archives of Virology, New York, NY, US vol. 143, No. 3, 1998, pp. 601-612.

Murtaugh, et al., EMBL Online Database, U87392, PRRS virus strain VR-2332 complete genome, Nov. 19, 1998 last update Version 4.

Choi et al., Journal of Virology, 80: 723-736, 2006.

Nelsen et al., Journal of Virology, 73: 270-280, 1999.

Nielsen et al., Journal of Virology, 77: 3702-3711, 2003.

(56) References Cited

OTHER PUBLICATIONS

Tan et al., Virus Genes, 22: 209-217, 2001.
Abstract 176 from the CRWAD 82$^{nd}$ Annual Meeting, Nov. 2001.
Abstract p. 6.6 from the IXth International Symposium on Nidoviruses, May 2003.
Han et al., Journal of Virology, 83: 9449-9463, 2009.
Posthuma et al., Journal of Virology, 82: 4480-4491, 2008.
Pei et al., Virology, 389: 91-99, 2009.
Kapur et al., Journal of General Virology, 77: 1271-1276, 1996.
Chen, Z., X. Zhou, et al. (2010). "Immunodominant epitopes in nsp2 of porcine reproductive and respiratory syndrome virus are dispensable for replication, but play an important role in modulation of the host immune response." Journal of General Virology, 91: 1047-1057.
Faaberg, K. S., M. E. Kehrli, et al. (2010). "In vivo growth of porcine reproductive and respiratory syndrome virus engineered nsp2 deletion mutants." Virus Research, 154: 77-85.
Guo, B., A. C. Vorwald, et al. (2011). "Large scale parallel pyrosequencing technology: PRRSV strain VR-2332 nsp2 deletion mutant stability in swine." Virus Research, 161: 162-169.
Vandeputte et al., American Journal of Veterinary Research, 2001; 62: 1805-1811.
Murtaugh et al., Vaccine. 2011; 29: 8192-8204.
Issued Patents_NA database sequence alignment of U.S. Pat. No. 6,500,662 SEQ ID No. Dec. 1, 2002 with SEQ ID No. 6.
Issued Patents_NA database sequence alignment of U.S. Pat. No. 7,132,106 SEQ ID No. Nov. 1, 2006 with SEQ ID No. 6.
Issued Patents_NA database sequence alignment of U.S. Pat. No. 7,232,680 SEQ ID No. Jun. 1, 2007 with SEQ ID No. 6.
Issued Patents_NA database sequence alignment of U.S. Pat. No. 7,618,797 Nov. 2009 SEQ ID No. 1 with SEQ ID No. 6.
Issued Patents_NA database sequence alignment of U.S. Pat. No. 7,691,389 Apr. 2010 SEQ ID No. 1 with SEQ ID No. 6.
Issued Patents_NA database sequence alignment of U.S. Pat. No. 8,481,705 Jul. 2013 SEQ ID No. 1 with SEQ ID No. 6.
Issued Patents_NA database sequence alignment of U.S. Pat. No. 8,492,132 Jul. 2013 SEQ ID No. 1 with SEQ ID No. 6.
Published_Applications_NA_Main database sequence alignment of U.S. Appl. No. 12/615,504, now U.S. Pat. No. 8,609,827 Dec. 2013 SEQ ID No. 1 with SEQ ID No. 6.
Published_Applications_NA Main database sequence alignment of U.S. Appl. No. 12/608,305 SEQ ID No. 1 with SEQ ID No. 6.
SEQ ID No. 6 sequence alignment with Genseq AFR07575, Jun. 2007.
GenEmbl ID GP721394 sequence alignment with SEQ ID No. 6, Dec. 2009.
Colson et al., Applied Animal Behavior Science, 2006, vol. 98, pp. 70-88.
O'Neill et al., Clinical and Vaccine Immunology, Nov. 2011, vol. 18, pp. 1865-1871.
Reynolds et al., The Veterinary Journal, 2009, vol. 181, pp. 312-320.
Murtaugh et al., Virus Research, 2010, vol. 154, pp. 18-30.
Savard et al., Canadian Journal of Veterinary Research, 2016, vol. 80, pp. 1-11.
Han et al., Veterinary Microbiology, 2017, vol. 209, pp. 30-47.
Jeong et al., Veterinary Microbiology, 2018, vol. 214, pp. 113-124.
O'Brien et al., "Fostera PRRS Vaccine for One-Day-Old Piglets: Respiratory Efficacy, Duration of Immunity, and Safety Research", Dec. 2014, vol. 1-8, retrieved on internet at: https://www. Zoetisus. com/products/pork/fosteraprrs/documents/tech-update-fostera-prrs-1-day-of-age.pdf.
Zhou et al., Veterinary Microbiology, 2017, vol. 207, pp. 108-116.
Balasch, M. et al., 2018, "Vaccination of 1-day-old pigs with a porcine reproductive and respiratory syndrome virus (PRRSV) modified live attenuated virus vaccine is able to overcome maternal immunity", Porcine Health Management, vol. 4, pp. 1-11.
Pearce, D. S. et al., 2014, "Live virus determination of PRRSV vaccines on primary porcine alveolar macrophages", Proceedings 23rd International Pig Veterinary Society, p. 162, Jun. 8-11, 2014. Cancun, Mexico.
Xiangju Wu et al., "Establishment and Characterization of a High and Stable Porcine CD163-Expressing MARC-145 Cell Line", BioMed Research International, Article ID 4315861, 9 pages, Hindawi Publishers, 2018, https://doi.org/10.1155/2018/4315861.
Sornsen, S. A. et al., "Effect of various stocking methods and extra-label PRRS vaccination on average daily gain", Swine Health and Production, 1998, vol. 6, pp. 7-11.

* cited by examiner

Figure 7

|  | Day 27 | Day31 | Day 35 | Day 37 |
|---|---|---|---|---|
| Mock | 0.61 | 2.74 | 4.02 | 3.95 |
| P129-PK-d43/44 | 2.25 | 2.81 | 3.15 | 2.20 |
| P129-PK-d43/44/46 | 1.59 | 3.64 | 3.52 | 2.96 |
| P129-PK-FL | 2.20 | 1.59 | 1.85 | 1.56 |
| BI | 0.92 | 2.98 | 2.91 | 2.53 |

Virus titer (log10 TCID50/ml)

Figure 8

Virulent isolate P129 (IN, 1995) Passage 0 pig serum and passage 1 on PAM cells 16 passages on PK-9 cells to adapt and attenuate.

parental wild-type virus SEQ ID NO:5 (pas. 0)

Make cDNA clone from passage 17 virus

Infectious cDNA Clone (DNA plasmid) SEQ ID NO:1 (pas.17)

7 additional passages on PK-9 cells to expand, adapt, and attenuate.

vaccine virus SEQ ID NO:3 (pas. 24)

Delete 2 amino acids and modify 2 codons in NLS

Modified infectious cDNA clone (DNA plasmid) SEQ ID NO:2 (pas.17)

17 additional passages on PK-9 cells to expand, adapt, and attenuate.

vaccine virus SEQ ID NO:4 (pas. 34)

EFFECTIVE VACCINATION AGAINST PORCINE REPRODUCTIVE AND RESPIRATORY SYNDROME (PRRS) VIRUS PRIOR TO WEANING

The present application is a continuation of U.S. application Ser. No. 13/895,564, filed May 16, 2013, and claims the benefit under 35 USC 119(e) of U.S. provisional application 61/648,461, filed May 17, 2012.

FIELD OF THE INVENTION

The present invention is in the field of animal health and is directed to infectious cDNA clones of positive polarity RNA viruses, novel RNA viruses and modified live forms thereof, and the construction of vaccines, in particular, swine vaccines, using such cDNA clones. More particularly, the present invention also provides for the safe and early vaccination of piglets prior to weaning, including from immediately after birth (i.e. only 1 day of age or less) to two weeks of age, at all times optionally in combination with multivalent combination swine vaccines, such as bivalent PRRSV/Mycoplasma hyopneumoniae (M. hyo) vaccines, bivalent PRRSV/Porcine Circovirus type 2 (PCV2) vaccines, and trivalent PRRSV/M. hyo/PCV2 vaccines, or simply as a monovalent PRRSV vaccine. Early vaccination against PRRS under such conditions provides an early onset of protective immunity, that arises no later than about 14 days after vaccination, i.e. at Day 15 following vaccination on Day 1 of life, Day 21 following vaccination on Day 7 of life, and no later than about Day 28 following vaccination on Day 14 of life. Although the present specification provides for numerous constructs of the "P129 strain" of North American PRRS virus (see PCT/IB2011/055003 and U.S. Pat. No. 6,500,662), which are highly effective as vaccines, including for such early and safe use, it has been determined that such early onset of protective immunity (i.e. about 2 weeks following immunizing vaccination given as early as Day 1 after birth), is also applicable to use of other North American and European PRRS strains, such as those described in U.S. Pat. Nos. 5,476,778, 5,846,805, 6,380,376, 6,982,160 and 6,197,310.

BACKGROUND OF THE INVENTION

Porcine reproductive and respiratory syndrome (PRRS) is characterized by abortions, stillbirths, and other reproductive problems in sows and gilts, as well as respiratory disease in young pigs. The causative agent is the PRRS virus (PRRSV), a member of the family Arteriviridae and the order Nidovirales. The nidoviruses are enveloped viruses having genomes consisting of a single strand of positive polarity RNA. The genomic RNA of a positive-stranded RNA virus fulfills the dual role in both storage and expression of genetic information. No DNA is involved in replication or transcription in Nidoviruses. The non-structural proteins are translated directly from the genomic RNA of nidoviruses as large polyproteins and subsequently cleaved by viral proteases into discreet functional proteins. A 3'-coterminal nested set of subgenomic RNAs (sgRNAs) is synthesized from the genome and are used as messenger RNAs for translation of the structural proteins. The reproduction of nidoviral genomic RNA is thus a combined process of genome replication and sgRNA synthesis.

In the late 1980's, two distinct genotypes of the virus emerged nearly simultaneously, one in North America and another in Europe. PRRS virus is now endemic in nearly all swine producing countries, and is considered one of the most economically important diseases affecting the global pork industry. Additionally, highly virulent genotypes have been isolated in China and surrounding countries, and such genotypes are generally related to North American genotypes.

Despite significant advances in understanding the biology of PRRSV, control of the virus remains difficult. Vaccination of animals in the field has proven to be largely ineffective. PRRS commonly re-emerges in immunized herds, and most on-farm PRRSV vaccination campaigns ultimately fail to control the disease.

Without being limited as to theory, infection of pigs with wild type PRRSV or their vaccination with a live attenuated form of this pathogen unfortunately only elicits an exuberant production of non-neutralizing antibodies. During this time interval, for example, only limited quantities of interferon (IFN)-γ (secreting cells are generated. Thus, PRRSV seems to inherently stimulate an imbalanced immune response distinguished by consistently abundant humoral (antibody-based) immunity, and a variable and limited but potentially protective T helper (Th) 1-like IFN-γ response. One characteristic of PRRSV infection that most likely contributes to the imbalanced development of adaptive immunity is the lack of an adequate innate immune response. Usually, virus-infected cells secrete type I interferon "IFN" (including IFN-α and IFN-β), which protects neighboring cells from infection. In addition, the released type I IFN interacts with a subset of naïve T cells to promote their conversion into virus-specific type II IFN (IFN-γ) secreting cells. In contrast, the IFN-α response of pigs to PRRSV exposure is nearly non-existent. Such inefficient stimulation of IFN-α production by a pathogen would be expected to have a significant impact on the nature of the host's adaptive immune response, since IFN-α up-regulates IFN-γ gene expression. Accordingly, the former cytokine controls the dominant pathway that promotes the development of adaptive immunity, namely, T cell-mediated IFN-γ responses and peak antiviral immune defenses.

In this regard, it has become evident that a probable link between innate and adaptive immunity in viral infections occurs through a special type of dendritic cell which has the ability to produce large amounts of type I interferon, and which plays a critical role in the polarization of T-cell function. Specifically, an infrequent but remarkable type of dendritic cell, the plasmacytoid dendritic cell (PDC), also known as a natural IFN-α/β-producing cell, plays a critical role in anti-viral immunity by means of their ability to cause naïve T cells to differentiate into IFN-γ secreting cells. Although rare, the PDC are enormously potent producers of IFN-α, with each cell being capable of producing 3-10 pg of IFN-α in response to virus. In contrast, monocytes produce 5- to 10-fold less IFN-α on a per cell basis. The phenotype and some biological properties of porcine PDC have been described (Summerfield et al., 2003, Immunology 110:440). Recent studies have determined that PRRSV does not stimulate porcine PDCs to secrete IFN-α (Calzada et al., 2010, Veterinary Immunology and Immunopathology 135:20).

This fact, in combination with the observation that exogenously added IFN-α at the time of vaccination has been found to improve the intensity of the PRRSV-specific IFN-γ response (W. A. Meier et al., Vet. Immunol. Immunopath. 102, pp 299-314, 2004), highlights the critical role that IFN-α plays during the infection of pigs with this virus. Given the apparent critical role of IFN-α on the development of protective immunity, it is important to determine the ability of different PRRS virus stocks to stimulate and/or inhibit the production of IFN-α. Accordingly, there is a pressing need for new and improved modified live vaccines to protect against PRRS. As described below, it is clear that viruses derived from the novel infectious cDNA clone, pCMV-S-P129-PK, and others, have a different phenotype than either the wild-type P129 virus or two commercially available modified live PRRS vaccines. Without being limited as to theory, the present invention provides for vaccines that facilitate cell-based immune response against the virus, and define a new and effective generation of PRRS vaccines.

SUMMARY OF THE INVENTION

In a first embodiment, the present invention provides an isolated polynucleotide molecule including a DNA sequence encoding an infectious RNA molecule encoding a PRRS virus that is genetically modified such that, as a vaccine, it elicits an effective immunoprotective response against the PRRS virus in porcine animals. In certain aspects, the invention provides for a DNA sequence as set forth herein including SEQ ID NO.:1, SEQ ID NO.:2, SEQ ID NO.:3, SEQ ID NO.:4, or SEQ ID: NO:6, or a sequence having at least 70% identity thereto, preferably 80% identity thereto, and more preferably 85%, 90%, 95%, 96%, 97%, 98% or 99% identity thereto.

In certain embodiments, the invention provides for a plasmid that includes an isolated polynucleotide molecule as set forth herein and a promoter capable of transcribing the polynucleotide molecule in a suitable host cell. In another embodiment, the North American or Chinese PRRS encoding sequence of the plasmid herein further encodes one or more detectable heterologous antigenic epitopes. The present invention provides for a transfected host cell that includes the plasmid set forth herein.

In another aspect, the present invention provides for a vaccine for protecting a porcine animal from infection by a PRRS virus. The vaccine may include a North American or Chinese PRRS virus encoded by an infectious RNA molecule, the infectious RNA molecule, or a plasmid, each of which are encoded by the isolated polynucleotide molecule as set forth herein. In yet another aspect, the vaccine includes a viral vector including the polynucleotide herein. The vaccine set forth herein may optionally include a vaccine carrier acceptable for veterinary use. In one important aspect, the vaccine has a decreased interferon-α inhibitory effect as compared to wild-type P129 PRRS virus (see ATCC 203488, 203489, U.S. Pat. No. 6,500,662).

In one embodiment, the present invention provides for diagnostic kit including polynucleotide molecules which distinguish (a so-called DIVA test) between porcine animals naturally infected with a field strain of a PRRS virus and porcine animals vaccinated with the modified live vaccine set forth herein.

In other embodiments, the invention provides for a method of protecting a porcine animal from infection with a strain of PRRS virus including administering to the animal an immunogenically protective amount of the vaccine of the claims set forth herein.

Further and preferred embodiments of the invention include an isolated Porcine Reproductive and Respiratory Syndrome Virus (PRRS), or a polynucleotide sequence encoding therefor, wherein the protein encoded by ORF1a is selected from a group consisting of those that contain any of the following amino acid sequences, wherein the underlined residues are believed to be novel: AMANVYD (SEQ ID NO: 9); IGHNAVM (SEQ ID NO: 12); TVPDGNC (SEQ ID NO: 15); CWWYLFD (SEQ ID NO: 18); HGVHGKY (SEQ ID NO: 21); AAKVDQY (SEQ ID NO: 24); PSATDTS (SEQ ID NO: 27); LNSLLSK (SEQ ID NO: 30); APMCQDE (SEQ ID NO: 33); CAPTGMD (SEQ ID NO: 36); PKVAKVS (SEQ ID NO: 39); AGEIVGV (SEQ ID NO: 42); ADFNPEK (SEQ ID NO: 45); and QTPILGR (SEQ ID NO: 48). In a further preferred embodiment of the invention, the invention provides an isolated North American or Chinese PRRS that contain any of the above-identified sequences within the protein encoded from ORF1a, including any combinations (2, 3, 4 . . . up to 17) of these identified sequences.

The invention further provides for an isolated Porcine Reproductive and Respiratory Syndrome Virus (PRRS) wherein the protein thereof encoded by ORF1a is selected from a group consisting of those amino acid sequences that contain any of: ANV (see SEQ ID NO: 9); HNA (see SEQ ID NO: 12); PDG (see SEQ ID NO: 15); WYL (see SEQ ID NO: 18); VHG (see SEQ ID NO: 21); KVD (see SEQ ID NO: 24); ATD (see SEQ ID NO: 27); SLL (see SEQ ID NO: 30); MCQ (see SEQ ID NO: 33); PTG (see SEQ ID NO: 36); VAK (see SEQ ID NO: 39); EIV (see SEQ ID NO: 42); FNP (see SEQ ID NO: 45); and PIL (see SEQ ID NO: 48), including any combinations (2, 3, 4 . . . up to 17) of these identified sequences.

In a further preferred embodiment, the invention provides an isolated North American or Chinese PRRS wherein, irrespective of the identity of any other specific nucleotide or amino acid sequence positions at any point in a polynucleotide encoding the virus or the proteins encoded therefrom, the ORF1a virus protein contains:
(a) any of the following specific amino acids in the specified sequences,
an amino acid N within the amino acid sequence ANV (see SEQ ID NO: 9);
an amino acid N within the amino acid sequence HNA (see SEQ ID NO: 12);
an amino acid D within the amino acid sequence PDG (see SEQ ID NO: 15);
an amino acid Y within the amino acid sequence WYL (see SEQ ID NO: 18);
an amino acid H within the amino acid sequence VHG (see SEQ ID NO: 21);
an amino acid V within the amino acid sequence KVD (see SEQ ID NO: 24);
an amino acid T within the amino acid sequence ATD (see SEQ ID NO: 27);
an amino acid L within the amino acid sequence SLL (see SEQ ID NO: 30).
an amino acid C within the amino acid sequence MCQ (see SEQ ID NO: 33);
an amino acid T within the amino acid sequence PTG (see SEQ ID NO: 36);
an amino acid A within the amino acid sequence VAK (see SEQ ID NO: 39);
an amino acid I within the amino acid sequence EIV (see SEQ ID NO: 42);
an amino acid N within the amino acid sequence FNP (see SEQ ID NO: 45); and
amino acid I within the amino acid sequence PIL (see SEQ ID NO: 48), to include any combinations (2, 3, 4 . . . up to 17) of these identified sequences, or
(b) contains said specific underlined single amino acids in the specified 3-residue ORF1a peptide sequences of any other North American or Chinese PRRS viruses that correspond to the 3-residue sequences as specified above, taking into account that said other specific 3-residue amino acid sequences may show one or two additional amino sequence changes, but still be recognized as corresponding to the sequences specified above. For the purposes of this embodiment of the invention, "corresponding" means that the relative sequences can be optimally aligned using a BLOSUM algorithm as described in Henikoff et al. Proc Natl. Acad. Sci., USA, 89, pp. 10915-10919, 1992.

In a further preferred embodiment of the invention, an isolated Porcine Reproductive and Respiratory Syndrome Virus (PRRS) is provided wherein the protein thereof encoded by ORF1a has an amino acid sequence that contains one or more of variations (a), (b), (c) and (d), wherein each said variation is defined as follows:
variation (a),
an amino acid N within the amino acid sequence ANV (see SEQ ID NO: 9);
an amino acid N within the amino acid sequence HNA (see SEQ ID NO: 12);
an amino acid D within the amino acid sequence PDG (see SEQ ID NO: 15),
an amino acid Y within the amino acid sequence WYL (see SEQ ID NO: 18);
an amino acid H within the amino acid sequence VHG (see SEQ ID NO: 21), or any subset of variation (a);
variation (b),
an amino acid V within the amino acid sequence KVD (see SEQ ID NO: 24);
an amino acid T within the amino acid sequence ATD (see SEQ ID NO: 27);
an amino acid L within the amino acid sequence SLL (see SEQ ID NO: 30).
an amino acid C within the amino acid sequence MCQ (see SEQ ID NO: 33), or any subset of variation (b);
variation (c),
an amino acid T within the amino acid sequence PTG (see SEQ ID NO: 36);
an amino acid A within the amino acid sequence VAK (see SEQ ID NO: 39), or any subset of variation (c); and
variation (d),
an amino acid I within the amino acid sequence EIV (see SEQ ID NO: 42);
an amino acid N within the amino acid sequence FNP (see SEQ ID NO: 45);
and amino acid I within the amino acid sequence PIL (see SEQ ID NO: 20), or any subset of variation (d) thereof.

Such PRRS viruses may further contain two or more of the five amino acid sequences identified in variation (a), and/or two or more of the four amino acid sequences identified in variation (b), and/or the two amino acid sequences identified in variation (c), and/or two or more of the three amino acid sequences identified in variation (d).

The present invention also provides a plasmid capable of directly transfecting a suitable host cell and expressing a Porcine Reproductive and Respiratory Syndrome Virus (PRRS) from the suitable host cell so transfected, which plasmid comprises: (a) a DNA sequence encoding an infectious RNA molecule encoding the PRRS virus, and (b) a promoter capable of transcribing said infectious RNA molecule, wherein the protein encoded by ORF1a of said virus has an amino acid sequence that contains:
(1) an amino acid N within the amino acid sequence ANV (see SEQ ID NO: 9);
an amino acid N within the amino acid sequence HNA (see SEQ ID NO: 12);
an amino acid D within the amino acid sequence PDG (see SEQ ID NO: 15),
an amino acid Y within the amino acid sequence WYL (see SEQ ID NO: 18);
an amino acid H within the amino acid sequence VHG (see SEQ ID NO: 21), or any subset thereof; and/or
(2) an amino acid V within the amino acid sequence KVD (see SEQ ID NO: 24);
an amino acid T within the amino acid sequence ATD (see SEQ ID NO: 27);
an amino acid L within the amino acid sequence SLL (see SEQ ID NO: 30).
an amino acid C within the amino acid sequence MCQ (see SEQ ID NO: 33), or any subset thereof; and/or
(3) an amino acid T within the amino acid sequence PTG (see SEQ ID NO: 36);
an amino acid A within the amino acid sequence VAK (see SEQ ID NO: 39), or any subset thereof; and/or
(4) an amino acid I within the amino acid sequence EIV (see SEQ ID NO: 42);
an amino acid N within the amino acid sequence FNP (see SEQ ID NO: 45);
and amino acid I within the amino acid sequence PIL (see SEQ ID NO: 48), or any subset thereof.

It will be appreciated that ORF1a encodes a polyprotein comprising protease function, and ORF1b encodes a polyprotein comprising replicase (RNA polymerase) and helicase functions. Additional information concerning the functions for proteins encoded from various ORFs (open reading frames) of PRRS may be found, for example, in U.S. Pat. No. 7,132,106. See also U.S. Pat. No. 7,544,362 in regard of function of ORF7, and other open reading frames. As would be appreciated in the art, the ORF1-encoded proteins are expected to have additional functions, known and unknown, and the novel amino acid changes useful in the practice of the present invention are not limited via their effects on any one specific function of the ORF1-encoded proteins.

In further preferred embodiments, said plasmid contains a promoter that is a eukaryotic promoter capable of permitting a DNA launch in targeted eukaryotic cells, or a prokaryotic or phage promoter capable of directing in vitro transcription of the plasmid. The invention similarly provides a method of generating a PRRS virus, which method comprises transfecting a suitable host cell with an appropriate plasmid and obtaining PRRS virus generated by the transfected cell.

Accordingly, in a specific and preferred embodiment, the invention provides an isolated polynucleotide molecule comprising a DNA sequence encoding an infectious RNA molecule encoding a North American PRRS virus, wherein said DNA sequence is selected from the group consisting of:
(a) SEQ ID NO:6;
(b) a sequence that has at least 85% identity to the DNA sequence of (a) wherein the protein encoded by ORF1a thereof has an amino acid sequence that contains:
from group (b) (1)
an amino acid N within the amino acid sequence ANV (see SEQ ID NO: 9);
an amino acid N within the amino acid sequence HNA (see SEQ ID NO: 12);
an amino acid D within the amino acid sequence PDG (see SEQ ID NO: 15),
an amino acid Y within the amino acid sequence WYL (see SEQ ID NO: 18);
an amino acid H within the amino acid sequence VHG (see SEQ ID NO: 21), or any subset thereof; and/or
from group (b) (2)
an amino acid V within the amino acid sequence KVD (see SEQ ID NO: 24);
an amino acid T within the amino acid sequence ATD (see SEQ ID NO: 27);

an amino acid L within the amino acid sequence SLL (see SEQ ID NO: 30).
an amino acid C within the amino acid sequence MCQ (see SEQ ID NO: 33), or any subset thereof; and/or
from group (b)(3)
an amino acid T within the amino acid sequence PTG (see SEQ ID NO: 36);
an amino acid A within the amino acid sequence VAK (see SEQ ID NO: 39), or any subset thereof; and/or
from group (b)(4)
an amino acid I within the amino acid sequence EIV (see SEQ ID NO: 42);
an amino acid N within the amino acid sequence FNP (see SEQ ID NO: 45);
and amino acid I within the amino acid sequence PIL (see SEQ ID NO: 20), or any subset thereof; and
(c) a DNA sequence that hybridizes to the complement of a DNA sequence of (a) or
(b) under highly stringent conditions which comprise hybridization to filter bound DNA in 0.5 M NaHPo4, 7% SDS, 1 mM EDTA at 65 degrees C., and washing in 0.1 SSC/0/1% SDS at 68 degrees C.

The invention also provides for host cells transfected with polynucleotide molecules and provides vaccines for protecting a porcine animal against infection by a PRRS virus, which vaccine comprises: (a) a genetically modified North American PRRS virus encoded by such aforementioned polynucleotide molecules, or (b) said infectious molecule, or (c) said polynucleotide molecule in the form of a plasmid, or (d) a viral vector comprising said polynucleotide molecule, wherein the PRRS virus is able to elicit an effective immunoprotective response against infection by PRRS virus, in an amount effective to produce immunoprotection against infection, and a carrier suitable for veterinary use.

The invention also provides RNA polynucleotide sequences corresponding to (i.e. by having complementary base coding sequences):
(a) the DNA sequence of SEQ ID NO:6;
(b) a DNA sequence that has at least 85% identity to the DNA sequence of (a) wherein the protein encoded by ORF1a thereof has an amino acid sequence that contains any of the following, and any combination of any of the following:
an amino acid N within the amino acid sequence ANV (see SEQ ID NO: 9);
an amino acid N within the amino acid sequence HNA (see SEQ ID NO: 12);
an amino acid D within the amino acid sequence PDG (see SEQ ID NO: 15),
an amino acid Y within the amino acid sequence WYL (see SEQ ID NO: 18);
an amino acid H within the amino acid sequence VHG (see SEQ ID NO: 21),
an amino acid V within the amino acid sequence KVD (see SEQ ID NO: 24);
an amino acid T within the amino acid sequence ATD (see SEQ ID NO: 27);
an amino acid L within the amino acid sequence SLL (see SEQ ID NO: 30).
an amino acid C within the amino acid sequence MCQ (see SEQ ID NO: 33),
an amino acid T within the amino acid sequence PTG (see SEQ ID NO: 36);
an amino acid A within the amino acid sequence VAK (see SEQ ID NO: 39),
(an amino acid I within the amino acid sequence EIV (see SEQ ID NO: 42);
an amino acid N within the amino acid sequence FNP (see SEQ ID NO: 45);
and amino acid I within the amino acid sequence PIL (see SEQ ID NO: 20), or
(c) a DNA sequence that hybridizes to the complement of a DNA sequence of (a) or (b) under highly stringent conditions which comprise hybridization to filter bound DNA in 0.5 M NaHPo4, 7% SDS, 1 mM EDTA at 65 degrees C., and washing in 0.1 SSC/0/1% SDS at 68 degrees C.

Accordingly, the invention also provides diagnostic kits comprising polynucleotide molecules which distinguish between porcine animals naturally infected with a field strain of a PRRS virus and porcine animals vaccinated with the vaccines of the invention, which vaccines (viruses) preferably evidence a decreased interferon-α inhibitory effect as compared to wild-type P129 PRRS virus (SEQ ID NO:5).

BRIEF DESCRIPTION OF THE TABLES AND FIGURES

Table 1 shows infectious cDNA clones and the corresponding viruses that were derived by transfection into PK-9 cells.

Table 2 shows the interferon-α inhibitory effect of wild-type PRRS virus and derivatives adapted to growth in cell culture.

Table 3 delineates the interferon-α inhibitory effect of wild-type PRRS virus P129 and its genetically engineered derivatives adapted to grow in CD163-expressing PK-9 cells.

Table 4 shows decreased interferon-α inhibitory effect of the P129-PK-FL and P129-PK-d43/44 viruses as compared to the wild-type P129 virus and the PRRS Ingelvac vaccines.

Table 5 depicts the design of a study conducted to evaluate the safety and efficacy of vaccine viruses.

Table 6 shows all nucleotide differences and resulting amino acid differences between P129 passage 0 and P129-PK-FL passage 17, by genome position.

Table 7 shows a summary of nucleotide and amino acid differences between P129 passage 0 and P129-PK-FL passage 17, by viral protein.

Table 8 shows all nucleotide differences and resulting amino acid differences between the PRRSV genomes found in infectious cDNA clones pCMV-S-P129 and pCMV-S-P129-PK17-FL, by genome position.

Tables 9 and 10 show amino acid changes contributing to the phenotype of the Passage 52 virus (SEQ ID NO:6).

Table 11 shows numbers of pigs with clinical signs following vaccination at one day of age with a modified live PRRSV vaccine.

Table 12 shows serum mean titers following vaccination at one day of age with a modified live PRRSV vaccine.

Table 13 shows percent lung lesions following a challenge of 7-week old pigs previously vaccinated at one day of age with a modified live PRRSV vaccine.

Table 14 shows percent lung lesions following a challenge of 18-week old pigs previously vaccinated at one day of age with a modified live PRRSV vaccine.

Table 15 shows percent lung lesions following a challenge of 26-week old pigs previously vaccinated at one day of age with a modified live PRRSV vaccine.

Table 16 shows percent lung lesions following a challenge of 5-week old piglets previously vaccinated with a modified live PRRSV vaccine.

FIG. 7 is a graphical representation of post-challenge virus load in serum (log TCID50/ml on PAM cells)

FIG. 8 is a pictorial representation of the methods employed for obtaining the vaccines including SEQ ID NO:1 through SEQ ID NO:6, as disclosed herein.

BRIEF DESCRIPTION OF THE MAJOR SEQUENCES

Figure 1:
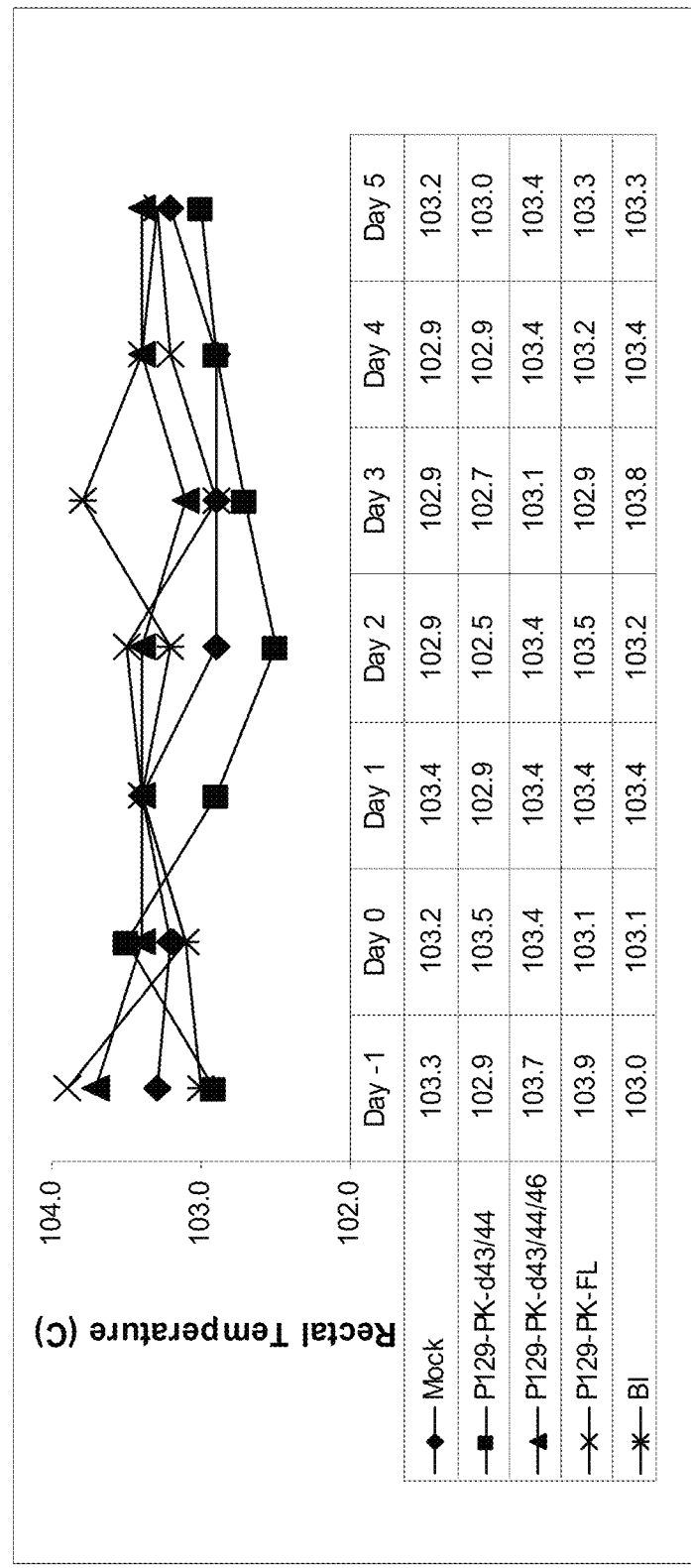
FIG. 1 shows rectal temperatures post-vaccination.

SEQ ID NO:1 provides the P129-PK-FL passage 17 complete genome.

SEQ ID NO:2 provides the P129-PK-d43/44 passage 17 complete genome.

SEQ ID NO:3 provides the P129-PK-FL passage 24 complete genome.

SEQ ID NO:4 provides the P129-PK-d43/44 passage 34 complete genome.

SEQ ID NO:5 provides the P129 passage 0 complete genome.

SEQ ID NO:6 provides the P129 passage 52 complete genome.

DETAILED DESCRIPTION OF THE INVENTION

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

"North American PRRS virus" means any PRRS virus having genetic characteristics associated with a North American PRRS virus isolate, such as, but not limited to the PRRS virus that was first isolated in the U.S. around the early 1990's (see, e.g., Collins, J. E., et al., 1992, J. Vet. Diagn. Invest. 4:117-126); North American PRRS virus isolate MN-1b (Kwang, J. et al., 1994, J. Vet. Diagn. Invest. 6:293-296); the Quebec LAF-exp91 strain of PRRS (Mardassi, H. et al., 1995, Arch. Virol. 140:1405-1418); and North American PRRS virus isolate VR 2385 (Meng, X.-J et al., 1994, J. Gen. Virol. 75:1795-1801). Genetic characteristics refer to genomic nucleotide sequence similarity and amino acid sequence similarity shared by North American PRRS virus strains. Chinese PRRS virus strains generally evidence about 80-93% nucleotide sequence similarity with North American strains.

"European PRRS virus" refers to any strain of PRRS virus having the genetic characteristics associated with the PRRS virus that was first isolated in Europe around 1991 (see, e.g., Wensvoort, G., et al., 1991, Vet. Q. 13:121-130). "European PRRS virus" is also sometimes referred to in the art as "Lelystad virus".

"An effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

A genetically modified PRRS virus is "attenuated" if it is less virulent than its unmodified parental strain. A strain is "less virulent" if it shows a statistically significant decrease in one or more parameters determining disease severity. Such parameters may include level of viremia, fever, severity of respiratory distress, severity of reproductive symptoms, or number or severity of lung lesions, etc.

"Host cell capable of supporting PRRS virus replication" means a cell which is capable of generating infectious PRRS when infected with a virus of the invention. Such cells include porcine cells of the monocyte/macrophage lineage such as porcine alveolar macrophage cells and derivatives, MA-104 monkey kidney cells and derivatives such as MARC-145 cells, and cells transfected with a receptor for the PRRS virus. The term "host cell capable of supporting PRRS virus replication" may also include cells within a live pig.

"Open reading frame", or "ORF", as used herein, means the minimal nucleotide sequence required to encode a particular PRRS virus protein without an intervening stop codon.

"Porcine" and "swine" are used interchangeably herein and refer to any animal that is a member of the family Suidae such as, for example, a pig. The term "PRRS virus", as used herein, unless otherwise indicated, means any strain of either the North American or European PRRS viruses.

"PRRS" encompasses disease symptoms in swine caused by a PRRS virus infection. Examples of such symptoms include, but are not limited to, fever, abortion in pregnant females, respiratory distress, lung lesions, loss of appetite, and mortality in young pigs. As used herein, a PRRS virus that is "unable to produce PRRS" refers to a virus that can infect a pig, but which does not produce any disease symptoms normally associated with a PRRS infection in the pig.

PRRSV "N protein" or "ORF7" as used herein is defined as a polypeptide that is encoded by ORF7 of both the European and North American genotypes of PRRS virus. Examples of specific isotypes of N protein which are currently known are the 123 amino acid polypeptide of the North American PRRS prototype isolate VR2322 reported in Genbank by Accession numbers PRU87392, and the 128 residue N protein of European prototype PRRS isolate Lelystad reported in Genbank Accession number A26843.

"PRRSV N protein NLS-1 region" or "PRRSV ORF7 NLS-1 region" refers to a "pat4" or "nuc1" nuclear localization signal (Nakai & Kanehisa, 1992; Rowland & Yoo, 2003) containing four continuous basic amino acids (lysine or arginine), or three basic residues and a histidine or proline, located within about the first 15 N-terminal residues of the mature N protein. By way of example the VR2332 NLS-1 region sequence is KRKK and is located at residues 9-12, while the Lelystad isolate sequence is KKKK and is located at residues 10-13 of the N protein.

"PRRSV N protein NLS-2 region" or "PRRSV ORF7 NLS-2 region" refers to a second nuclear localization signal within the N protein that can take one of two forms. In North American PRRS viruses NLS-2 has a pattern which we have designated as the "pat8" motif, which begins with a proline followed within three residues by a five residue sequence containing at least three basic residues (K or R) out of five (a slight modification of the "pat7" or "nuc2" motif described by Nakai & Kanehisa, 1992; Rowland & Yoo, 2003). By way of example such a sequence is located at N protein residues 41-47 of the North American PRRSV isolate VR2332, and is represented by the sequence P . . . K In European PRRS viruses NLS-2 has a "pat4" or "nuc1" motif, which is a continuous stretch of four basic amino acids or three basic residues associated with histidine or proline (Nakai & Kanehisa, 1992; Rowland & Yoo, 2003). The NLS-2 of the European PRRSV isolate Lelystad is located at residues 47-50 and is represented by the sequence K . . . K "PRRSV N protein NoLS region" or "PRRSV ORF7 NoLS region" refers to a nucleolar localization signal having a total length of about 32 amino acids and incorporating the NLS-2 region near its amino terminus. By way of example the VR2332 NoLS region sequence is located at residues 41-72 and is represented by the sequence P . . . R (Rowland & Yoo, 2003) and the corresponding Lelystad isolate sequence is located at residues 42-73 and is represented by the sequence P . . . R.

"Transfected host cell" means practically any host cell which as described in U.S. Pat. No. 5,600,662 when transfected with PRRS virus RNA can produce a at least a first round of PRRS virions.

An "infectious DNA molecule", for purposes of the present invention, is a DNA molecule that encodes the necessary elements to support replication, transcription, and translation into a functional virion from a suitable host cell. Likewise, an "isolated polynucleotide molecule" refers to a composition of matter comprising a polynucleotide molecule of the present invention purified to any detectable degree from its naturally occurring state, if any.

For purposes of the present invention, the nucleotide sequence of a second polynucleotide molecule (either RNA or DNA) is "homologous" to the nucleotide sequence of a first polynucleotide molecule, or has "identity" to said first polynucleotide molecule, where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. Homologous polynucleotide sequences also refers to sense and anti-sense strands, and in all cases to the complement of any such strands. For purposes of the present invention, a polynucleotide molecule is useful in practicing the present invention, and is therefore homologous or has identity, where it can be used as a diagnostic probe to detect the presence of PRRS virus or viral polynucleotide in a fluid or tissue sample of an infected pig, e.g. by standard hybridization or amplification techniques. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). In a specific example for calculations according to the practice of the present invention, reference is made to BLASTP 2.2.6 [Tatusova TA and TL Madden, "BLAST 2 sequences—a new tool for comparing protein and nucleotide sequences." (1999) FEMS Microbiol Lett. 174:247-250.]. Briefly, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 89:10915-10919. 1992). The percent identity is then calculated as: Total number of identical matches×100/divided by the length of the longer sequence+number of gaps introduced into the longer sequence to align the two sequences.

Preferably, a homologous nucleotide sequence has at least about 75% nucleotide sequence identity, even more preferably at least about 80%, 85%, 90% 95%, 96%, 97%, 98% and 99% nucleotide sequence identity. Since the genetic code is degenerate, a homologous nucleotide sequence can include any number of "silent" base changes, i.e. nucleotide substitutions that nonetheless encode the same amino acid.

A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tyrptophan and phenylalanine. Amino acids can be classified according to physical properties and contribution to secondary and tertiary protein structure. A conservative substitution is recognized in the art as a substitution of one amino acid for another amino acid that has similar properties. Exemplary conservative substitutions may be found in WO 97/09433, page 10, published Mar. 13, 1997 (PCT/GB96/02197, filed Sep. 6, 1996. Alternatively, conservative amino acids can be grouped as described in Lehninger, (Biochemistry, Second Edition; Worth Publishers, Inc. NY:NY (1975), pp. 71-77). Additional suitable conservative changes and the application thereof are described below.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 (or any other particular polynucleotide sequence) if it hybridizes to the complement of SEQ ID NO:1 under moderately stringent conditions, e.g., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et al editors, Protocols in Molecular Biology, Wiley and Sons, 1994, pp. 6.0.3 to 6.4.10), or conditions which will otherwise result in hybridization of sequences that encode a PRRS virus as defined below. Modifications in hybridization conditions can be empirically determined or precisely calculated based on the length and percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

In another embodiment, a second nucleotide sequence is homologous to SEQ ID NO:1 (or any other sequence of the invention) if it hybridizes to the complement of SEQ ID NO:1 under highly stringent conditions, e.g. hybridization to filter-bound DNA in 0.5 M $NaHPO_4$, 7% SDS, 1 mM EDTA at 65° C., and washing in 0.1×SSC/0.1% SDS at 68° C., as is known in the art (Ausebel et al. Current Protocols in Molecular Biology, Greene Publishing and Wiley Interscience, New York, 1989.

It is furthermore to be understood that the isolated polynucleotide molecules and the isolated RNA molecules of the present invention include both synthetic molecules and molecules obtained through recombinant techniques, such as by in vitro cloning and transcription.

Polynucleotide molecules can be genetically mutated using recombinant techniques known to those of ordinary skill in the art, including by site-directed mutagenesis, or by random mutagenesis such as by exposure to chemical mutagens or to radiation, as known in the art." The mutations may be carried out by standard methods known in the art, e.g. site directed mutagenesis (see e.g. Sambrook et al. (1989) Molecular Cloning: A Laboratory Manual, 2nd Ed., Cold Spring Harbor Laboratory Press, Cold Spring Harbor, N.Y.) of an infectious copy as described (e.g. Meulenberg et al., Adv. Exp. Med. Biol., 1998, 440:199-206).

Accordingly, the subject invention further provides a method for making a genetically modified North American PRRS virus, which method comprises mutating the DNA sequence encoding an infectious RNA molecule which encodes the PRRS virus as described above, and expressing the genetically modified PRRS virus using a suitable expression system. A genetically modified PRRS virus can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro, as is described in further detail below.

The North American PRRSV N protein sequences are highly conserved and the reported sequences have about 93-100% identity with each other. The North American and European PRRSV N proteins are about 57-59% identical and share common structural motifs. Generally, when comparing PRRS encoding sequences and isolates, which might be numbered differently as to specific nucleotides or encoded amino acids, identification of the proper regions are readily achieved by identifying preserved characteristic amino acids in a PRRS strain of interest and aligning it with a reference strain.

Recombinant DNA technology comprises extremely varied and powerful molecular biology techniques aimed at modifying nucleic acids at the DNA level and makes it possible to analyze and modify genomes at the molecular level. In this respect, viruses such as the PRRS virus because of the modest size of its genome is particularly amenable to such manipulations. However, recombinant DNA technology is not immediately applicable to non-retroviral RNA viruses because these viruses do not encompass a DNA intermediate step in their replication. For such viruses, infectious cDNA clones have to be developed before recombinant DNA technology can be applied to their genome to generate modified virus. Infectious clones can be derived through the construction of full-length (genomic length) cDNA (here used in the broad sense of a DNA copy of RNA and not only in the strict sense of a DNA copy of mRNA) of the virus under study, after which an infectious transcript is synthesized in vivo in cells transfected with the full-length cDNA, but infectious transcripts can also be obtained by in vitro transcription from full-length cDNA in a plasmid having a prokaryotic promoter in the presence of a transcription cocktail, or again in vitro using ligated partial-length cDNA fragments that comprise the full viral genome. In all cases, the transcribed RNA carries all the modifications that have been introduced to the cDNA and can be used to further passage the thus modified virus.

The preparation of an infectious clone of a European PRRS virus isolate or Lelystad virus is described in U.S. Pat. No. 6,268,199 which is hereby fully incorporated by reference. The preparation of an infectious cDNA clone of a North American PRRS virus isolate designated P129 (Lee et al., 2005; Yoo et al., 2004) is described in U.S. Pat. No. 6,500,662 which is hereby incorporated fully by reference. The sequence of P129 cDNA is disclosed in Genbank Accession Number AF494042 and in U.S. Pat. No. 6,500, 662. Our work below makes use of such an infectious clone which in the context of a plasmid is expressed by the CMV immediate early promoter and has been designated pCMV-S-P129 and is also disclosed within U.S. Pat. No. 6,500,662. As described in U.S. Pat. No. 6,500,662 there are other plasmids and promoters suitable for use here.

Given the complete sequence of any open reading frame of interest and the location of an amino acid residue of interest, one of ordinary skill need merely consult a codon table to design changes at the particular position desired.

Codons constitute triplet sequences of nucleotides in mRNA and their corresponding cDNA molecules. Codons are characterized by the base uracil (U) when present in a mRNA molecule but are characterized by base thymidine (T) when present in DNA. A simple change in a codon for the same amino acid residue within a polynucleotide will not change the sequence or structure of the encoded polypeptide. It is apparent that when a phrase stating that a particular 3 nucleotide sequence "encode(s)" any particular amino acid, the ordinarily skilled artisan would recognize that the table above provides a means of identifying the particular nucleotides at issue. By way of example, if a particular three nucleotide sequence encodes lysine, the table above discloses that the two possible triplet sequences are AAA and AAG. Glycine is encoded by GGA, GGC, GGT (GGU if in RNA) and GGG. To change a lysine to glycine residue in an encoded protein one might replace a AAA or AAG triplet with any of by GGA and GGC, GGT or GGG in the encoding nucleic acid.

As aforementioned, the present invention is directed to the provision of vaccine strains of PRRS wherein host responses to the virus that are mediated by interferon pathways, among other responses, are not downregulated. As described in detail below, there are various modifications to the viral genome that are effective in this regard, particularly those found in ORF1a as disclosed herein, and combinations thereof. It should be noted that similar modification points can be found in additional open reading frames of the PRRS genome, as also disclosed herein (see Table 9).

It is noteworthy that certain other prior approaches to modification of the PRRS polynucleotide have been successful in order to attenuate the PRRS virus, possibly providing suitability for vaccine use, although the exact cause of the resultant attenuations is not generally known. For example, it has been disclosed to attenuate a virulent PRRS virus by mutating or deleting the NLS-2 region, NoLS region, or the NES region in the nucleocapsid or N protein (encoded by ORF7) of the virus, to include a deletion in open reading frame 7 (ORF7). In another aspect the ORF7 deletion is within the sequence encoding a nuclear localization signal (NLS) of a capsid protein. The ORF7 deletion within the sequence encoding an NLS may include deletion of one or more amino acids at positions 43-48 or deletion of an amino acid at either or both positions 43 and 44. See, for example, the entire disclosure of U.S. Pat. No. 7,544,362 which is incorporated by reference. The nucleocapsid protein (N) of PRRSV, which is encoded by ORF7, is a small basic protein that is phosphorylated (Wootton, Rowland, and Yoo, 2002) and forms homodimers (Wootton and Yoo, 2003). The crystal structure has recently been determined (Doan and Dokland, 2003). The N protein appears to have multiple functions in the infected cell. In addition to forming a spherical capsid structure into which genomic RNA is packaged, a process that takes place in the cytoplasm, a portion of N protein is transported into the nucleus and specifically to the nucleolus of the infected cell. The amino acid sequence of N protein contains two nuclear localization signals (NLS), a nucleolar localization signal (NoLS), and a nuclear export signal (NES) that facilitate transport into the nucleus and nucleolus, and export from the nucleus, respectively (Rowland et al., 1999; Rowland et al., 2003; Rowland and Yoo, 2003). While in the nucleolus, the N protein interacts with the small nucleolar RNA-associated protein fibrillarin and may regulate rRNA processing and ribosome biogenesis in the infected cell in order to favor virus replication (Yoo et al., 2003). Viral mutations of this type are valuable, either alone or in combination with other attenuating mutations, for designing novel PRRS vaccines. In another example of a PRRS virus that has been attenuated, modified to ORF1a was employed. Deletion of the DNA sequence encoding the antigenic epitope between amino acids 616 to 752 in the hypervariable region in the non-structural protein 2 coding region of ORF1a was employed, see. U.S. Pat. No. 7,618,797, which is incorporated by reference in its entirety.

Studies on the immunobiology of PRRS virus are suggestive that the interaction of PRRS virus with PDCs merits examination. This cell type represents 0.2%-0.8% of peripheral blood mononuclear cells in humans, mice, rats, pigs and monkeys. Despite its scarcity, this cell is an important component of the innate immune system and is capable of secreting copious amounts of IFN-α following viral stimulation. It is through the secretion of IFN-α that PDCs play a major role in regulating antiviral innate and adaptive immunity since they promote the function of natural killer cells, B cells, and T cells. Furthermore, the maturation of porcine monocyte derived dendritic cells (MoDC) is aided by the IFN-α secreted by PDCs resulting in an enhanced ability of MoDCs to present antigen and activate T cells. At a later stage of viral infection, PDCs differentiate into a unique type of mature dendritic cell, which directly regulates the function of T cells and direct the differentiation of T cells into cells capable of secreting IFN-γ, which is a major mediator of antiviral immunity against viruses including PRRS virus. Not surprisingly there are human viruses, such as respiratory syncitial virus and measles virus, which are known to suppress the ability of PDCs to secrete IFN-α. This inhibitory effect is thought to play a role in the predominance of a humoral immune response and the associated immunopathology observed as a result of the infection with these viruses, as well as in the increased susceptibility of the host to secondary bacterial and viral infections.

In contrast, the wild-type PRRSV isolates as well as both of the Ingelvac PRRS vaccine strains (see Examples 5 and following, below) inhibited the ability of purified populations of porcine PDC to produce IFN-α, while the novel P129-PK-FL and P129-PK-d43/44 virus stocks (see below) exhibited a minimal to nil inhibitory effect on this PDC function. The significance of these observations resides, in part, on the importance of IFN-α in regulating the development of the adaptive immune response to viruses. Accordingly, it is very likely that an attenuated virus vaccine derived from a minimally IFN-α suppressing virus would elicit a strong antiviral protective immune response. It has previously been demonstrated the adjuvant effect of IFN-α on the Ingelvac PRRS MLV vaccine induced virus-specific T cell mediated IFN-γ response, and that the intensity of the virus-specific T cell mediated IFN-γ response elicited by the vaccine has a positive correlation with protective immunity against the virus under field and laboratory conditions. Accordingly, although not being limited as to theory, it would be reasonable to expect that the cell-mediated immune response and level of protective immunity elicited by a non-IFN-α-inhibitory PRRSV will be significantly greater than that of a PRRSV isolate exhibiting the wild-type (IFN-α inhibitory) phenotype.

Referring to the present invention, it is notable that the P129-PK-FL virus as well as all five deletion mutants derived from the pCMV-S-P129-PK infectious cDNA clone lost the ability to inhibit IFN-α production. Therefore this unusual phenotype can not be solely due to the deletions, but must be due at least in part to genetic changes that became fixed during construction of the infectious clone. Interestingly, uncloned P129 virus that was serially passaged 63 times on PK-9 cells retained the ability to inhibit IFN induction (Table 1). The most likely explanation for the common IFN phenotype seen in all infectious clone-derived viruses is the incorporation of one or more mutations during the generation of the infectious clone. These mutations would have existed, possibly at low levels, in the viral RNA used to construct the infectious clone. Ultimately, the mutations may have existed in the original (passage 0) virus in the pig or they may have been generated and enriched during the process of adapting the virus to growth on PK-9 cells for 16 passages. The possibility that the mutations were the result PCR-induced errors or cloning artifacts cannot be ruled out. At any rate, the mutation(s) responsible for the loss of the IFN-α inhibitory function became "fixed" during infectious clone construction, and would be expected to be present in all viruses derived from this particular infectious clone.

The possibility that mutations responsible for the altered IFN-α inhibition phenotype pre-existed in the viral RNA used to construct the cDNA clone is likely, given that PRRSV is known to readily generate random genetic diversity as a result of errors by the viral RNA-dependent RNA polymerase. Virus quasi-species are comprised of a heterogeneous mixture of closely related genetic variants that naturally appear during virus replication in vivo. Even more relevant is the observation of virus quasi-species after multiple in vitro passages of PRRSV derived from an infectious cDNA clone. This is notable since the starting population of virus genomes in previously conducted studies consisted of a genetically homogenous population, and sequence diversity was rapidly generated during passage in cell culture. In the current study, the level of genomic heterogeneity would have been higher, since the original P129 virus had not been cloned (biologically or molecularly) prior to the 16 PK-9 passages leading up to construction of the infectious clone. Thus the chance selection of a PRRSV RNA variant responsible for the loss of IFN-α inhibition function from among the quasi-species, and incorporation into the pCMV-S-P129-PK17-FL infectious cDNA clone seems plausible. The incorporation of these mutations into an infectious clone might be considered fortuitous, under some circumstances, given that all derivative viruses should share this distinct biological phenotype which may prove important for the development of effective next-generation PRRS vaccines.

The wild-type PRRS virus strain P129, like other strains of this virus, exhibited a strong inhibitory effect on the ability of peripheral blood mononuclear cells (PBMCs) and plasmacytoid dendritic cells (PDCs) to produce interferon (IFN)-α. On the other hand, virus derived from an infectious cDNA clone of P129 (pCMV-S-P129-PK17-FL) exhibited a significant reduction in the IFN-α inhibitory phenotype. This infectious clone was constructed from virus which was previously adapted to grow on the CD163-expressing porcine kidney cell line PK-9 over the course of 16 serial passages (see U.S. Pat. No. 7,754,464 which is incorporated by reference in its entirety). The IFN-α inhibitory phenotype of P129-PK-FL and P129-PK-d43/44 ranged from low to negligible and was in marked contrast to that exhibited by either of the two Ingelvac PRRS modified live virus vaccine strains, both of which were highly inhibitory. These results indicate that the P129-PK-FL and P129-PK-d43/44 viruses are biologically distinct from the parental low-passage P129 isolate, other wild-type PRRS viruses, and both Ingelvac PRRS vaccines. The potential implications of the reduced IFN-α-inhibitory phenotype, as well as possible reasons for the phenotypic change, are discussed.

Amino Acid Modifications of the Invention

According to the practice of the present invention, novel isolates of PRRS, whether of North American or Chinese genotypes, may be field-identified that contain specific contain amino acids at specific positions in the proteins encoded from ORF1, and which confer desirable phenotypes on these viruses. In the alternative, as aforementioned, standard genetic procedures may be employed to modify the genetic sequence (and thus the amino acid sequence) of the encoded ORF1 protein, again to produce modified North American and Chinese PRRS viruses, and infectious clones, and vaccines therefrom, all which provide such phenotypes. In preferred examples the phenotypes include, without limitation, decreased interferon-α inhibitory effect as compared to wild-type PRRS virus, and, optionally, the ability to reproduce or persist in a host animal (a pig) while triggering a robust immune response, but with little detectable pathology.

Thus, in the practice of the invention, North American PRRS strains or isolates that may serve as useful starting points include those disclosed, for example in U.S. Pat. Nos. 6,500,662; 7,618,797; 7,691,389, 7,132,106; 6,773, 908; 7,264,957; 5,695,766; 5,476,778; 5,846,805; 6,042,830; 6,982,160; 6,241,990; and 6,110,468. In regard of Chinese PRRS strains and isolates that may serve as useful starting points, see for example, published Chinese application CN200910091233.6 from Chinese application CN201633909 pertaining to the TJM-92 virus.

In connection with the discussion that follows, internationally recognized single and three-letter designations are used for the most common amino acids encoded by DNA: alanine (Ala, A); arginine (Arg, R); asparagine (Asn, N); aspartic acid (Asp, D); cysteine (Cys, C); glutamic acid (Glu, E); glutamine (Gln, Q); glycine (Gly, G); histidine (His, H); isoleucine (Ile, I); leucine (Leu, L); lysine (Lys, K); methionine (Met, M); phenylalanine (Phe, F); proline (Pro, P); serine (ser, S); threonine (Thr, T); tryptophan (Trp, W); tyrosine (Tyr, Y) and Valine (Val, V).

Tables 9 and 10 identify observed amino acid changes responsible for attenuation of virulence in North American (and Chinese) PRRS which correlate with reduced inhibition of interferon alpha activity, thereby permitting a safe and robust immune response to vaccines. Table 10 identifies highly preferred amino acid modifications in this regard, within ORF1a, and shows how these mutations have arisen in regard of passaging from other P129 cultures (it should be noted that the inspection of this history also facilitates design of mutagenesis strategies to (re) construct encoding DNA having any of the amino acid changes of the invention, as needed). In this regard, the most preferred amino acid improvements to ORF1a (as evidenced by P129 passage 52 include: asparagine at 182, asparagine at 189, tyrosine at 273, histidine at 302, threonine at 665, cysteine at 943, threonine at 1429, alanine at 1505, asparagine at 2410, which also potentially adds numerous glycoslation opportunities and which may further alter protein function.

Accordingly, the invention provides an isolated Porcine Reproductive and Respiratory Syndrome Virus (PRRS) wherein the protein thereof encoded by ORF1a is selected from a group consisting of those amino acid sequences that contain any of:

an amino acid N within the amino acid sequence AMA<u>N</u>VYD (SEQ ID NO: 9);
an amino acid N within the amino acid sequence IGH<u>N</u>AVM (SEQ ID NO: 12);
an amino acid D within the amino acid sequence TVP<u>D</u>GNC (SEQ ID NO: 15);

an amino acid Y within the amino acid sequence CWW Y̲LFD (SEQ ID NO: 18);
an amino acid H within the amino acid sequence HGV H̲GKY (SEQ ID NO: 21);
an amino acid V within the amino acid sequence AAK V̲DQY (SEQ ID NO: 24);
an amino acid T within the amino acid sequence PSAT̲DTS (SEQ ID NO: 27);
an amino acid L within the amino acid sequence LNSL̲LSK (SEQ ID NO: 30).
an amino acid C within the amino acid sequence APM C̲QDE (SEQ ID NO: 33);
an amino acid T within the amino acid sequence CAPT̲GMD (SEQ ID NO: 36);
an amino acid A within the amino acid sequence PKVA̲KVS (SEQ ID NO: 39);
an amino acid I within the amino acid sequence AGEI̲VGV (SEQ ID NO: 42);
an amino acid N within the amino acid sequence ADFN̲PEK (SEQ ID NO: 45); and
an amino acid I within the amino acid sequence QTPI̲LGR (SEQ ID NO: 48).

More specifically, the invention provides an isolated Porcine Reproductive and Respiratory Syndrome Virus (PRRS) wherein the protein thereof encoded by ORF1a is selected from a group consisting of those amino acid sequences that contain any of:
an amino acid N within the amino acid sequence AN̲V (see SEQ ID NO: 9);
an amino acid N within the amino acid sequence HN̲A (see SEQ ID NO: 12);
an amino acid D within the amino acid sequence PD̲G (see SEQ ID NO: 15);
an amino acid Y within the amino acid sequence WY̲L (see SEQ ID NO: 18);
an amino acid H within the amino acid sequence VH̲G (see SEQ ID NO: 21);
an amino acid V within the amino acid sequence KV̲D (see SEQ ID NO: 24);
an amino acid T within the amino acid sequence AT̲D (see SEQ ID NO: 27);
an amino acid L within the amino acid sequence SL̲L (see SEQ ID NO: 30).
an amino acid C within the amino acid sequence MC̲Q (see SEQ ID NO: 33);
an amino acid T within the amino acid sequence PT̲G (see SEQ ID NO: 36);
an amino acid A within the amino acid sequence VA̲K (see SEQ ID NO: 39);
an amino acid I within the amino acid sequence EI̲V (see SEQ ID NO: 42);
an amino acid N within the amino acid sequence FN̲P (see SEQ ID NO: 45); and
amino acid I within the amino acid sequence PI̲L (see SEQ ID NO: 48).

As aforementioned, there are numerous known strains and isolates of North American and Chinese PRRS, and novel strains continue to evolve or to be isolated. Although a high level of amino acid sequence homology exists between all these strains, those skilled in the art will immediately recognize that some variation does exist, and indeed advantage can be taken of these differences and similarities to further improve the phenotypic properties of all vaccine strains.

First, in regard of all of the amino acid motifs defined by SEQ ID NOS as specified directly (on Pages 27-28) above, the underlined and preferred amino acids (as provided from P129 passage 52) generally remain fully beneficial even if adjacent amino acids have otherwise changed from the specified SEQ ID NO sequences. Thus in regard of AMA N̲VYD (SEQ ID NO: 9), as a specific and representative example, it is generally possible to inspect the corresponding ORF1-expressed protein sequence from any North American or Chinese PRRS, to find the corresponding amino acid motif, even if additional changes have occurred in such other strains, as a result of evolution, causing substitutions and/or deletions or additions. As will be appreciated by those skilled in the art, the preferred amino acid changes evidenced by P129 passage 52 should thus also remain operable in spite of other changes in overall amino acid sequence that are directly 5' or 3' to the specified amino acid of Passage 52. This will be so especially if the comparative amino acid changes are considered conservative. Thus in regard of AMAN̲VYD (SEQ ID NO: 9), and the subsequence AN̲V thereof, it should be readily possible to identify the comparable motif in another PRRS strain if, for example, the valine therein is replaced by isoleucine or leucine, or any other residue, or if a residue is simply missing or an additional residue added. Numerous computer programs exist to identify alignments and thus determine if polypeptide sequence motifs correspond, for example the so-called Blosum tables (based on a given level of percent identity), see S. Henikoff et al. "Amino Acid Substitution matrices from protein blocks", Proc Natl Acad Sci, USA, 89(22), pp. 10915-10919, Nov. 15, 1992, 925 and see also A. L. Lehninger et al. Principles of Biochemistry, 2005, MacMillan and Company, 4$^{th}$ edition. Conservative amino acid changes are also recognized based on categorization into 5 overall groups: sulfydryl (Cys); aromatic (Phe, Tyr, and Trp); basic (Lys, Arg, His); aliphatic (Val, Ileu, Leu, Met), and hydrophilic (Ala, Pro, Gly, Glu, Asp, Gln, Asn, Ser and Thr). Thus it is within the practice of the invention to modify any North American or Chinese PRRS encoding nucleotide sequence to incorporate at the appropriate and corresponding position, any of the amino acid changes specified for P129 passage 52, even if one or more of the other amino acids adjacent to the designated position have been added, deleted or substituted.

Additionally, based on similar principles, those skilled in the art will recognize that once a preferred amino acid is identified from the specific Passage 52 changes identified for ORF1a according to the practice of the present invention, that conservative replacements for any such passage 52 amino acids can then also be used, either in P129 variants, or in regard of any other North American or Chinese strains, with substantial preservation of the intended passage 52 phenotype. Thus, as representative examples: in regard of S L̲L (within SEQ ID NO: 30), the designated leucine residue may be further replaced with isoleucine, valine or methionine; in regard of FN̲P (within SEQ ID NO: 45), the designated asparagine may be replaced with any of Ala, Pro, Gly, Glu, Asp, Gln, Ser and Thr; and in regard of VA̲K (see SEQ ID NO: 39), the designated alanine may be replaced with any of Asn, Pro, Gly, Glu, Asp, Gln, Ser and Thr; all and the like, although it will be readily recognized that it is not a requirement of the present invention that any such replacement amino acids work as well as originally identified unique Passage 52 amino acid changes, at the specified locations. Of course, use of standard conservative amino acid changes according to any other recognized model also is practiced in the present invention. For example, and including vice-versa in all cases, Asp for Glu and vice versa, Asn for Gln, Arg for Lys, Ser for Cys or Thr, Phe for Tyr, Val for Leu or Ileu, Ala for Gly, and the like.

Further, within the practice of the present invention, although any of the individual Passage 52 amino acid changes (as identified for ORF1a above) can be usefully placed in any North American of Chinese PRRS with desired phenotypic effect, it is further preferred to in include as many of the Table 9 or Table 10 amino acid selections as possible in a final construct, as typically provided for by appropriate modification of the encoding polynucleotide sequence. Thus, the practice of the present invention includes the provision of Chinese or North American PRRS viruses (and corresponding encoding polynucleotides) that provide for 2, 3, 4, 5, 6, 7, 8, 9, and up to any of the approximately 17 identified Passage 52 ORF1a changes, (Table 9) all within a final viral sequence, to include any specific pairs, triplets, or other higher combinations of all the total identified Passage 52 amino acid changes. Such amino acid changes may, of course, be introduced into the corresponding encoding nucleotide sequences of the virus by site directed mutagenesis, PCR, and other techniques as are well known in the art.

To demonstrate that a particular genetically modified strain is attenuated an experiment described as follows may be used.

At least 10 gilts per group are included in each trial, which are derived from a PRRSV-free farm. Animals are tested free of PRRS virus specific serum antibodies and negative for PRRSV. All animals included in the trial are of the same source and breed. The allocation of the animals to the groups is randomized.

Challenge is performed at day 90 of pregnancy with intranasal application of 1 ml PRRSV with $10^5$ TCID$_{50}$ per nostril. There are at least three groups for each test setup: One group for P129 challenge; one test group for challenge with the possibly attenuated virus; and one strict control group.

The study is deemed valid when the strict controls stay PRRSV-negative over the time course of the study and at least 25% less live healthy piglets are born in the P129 challenged group compared to the strict controls.

Attenuation, in other words less virulence, is defined as the statistical significant change of one or more parameters determining reproductive performance or other symptomology:

Significant reduction in at least one of the following parameters for the test group (possibly attenuated virus) compared to the unmodified parental strain infected group would be an indication of attenuation:
a) frequency of stillborns
b) abortion at or before day 112 of pregnancy
c) number of mummified piglets
d) number of less lively and weak piglets
e) pre-weaning mortality Furthermore a significant increase in one of the following parameters for the test group compared the unmodified parental strain infected group is preferred:
f) number of piglets weaned per sow
g) number of live healthy piglets born per sow In the alternative, respiratory symptoms and other symptoms of PRRSV infection could be examined to establish attenuation.

An attenuated strain is valuable for the formulation of vaccines. The present vaccine is effective if it protects a pig against infection by a PRRS virus. A vaccine protects a pig against infection by a PRRS virus if, after administration of the vaccine to one or more unaffected pigs, a subsequent challenge with a biologically pure virus isolate (e.g., VR 2385, VR 2386, P129 etc.) results in a lessened severity of any gross or histopathological changes (e.g., lesions in the lung) and/or of symptoms of the disease, as compared to those changes or symptoms typically caused by the isolate in similar pigs which are unprotected (i.e., relative to an appropriate control). More particularly, the present vaccine may be shown to be effective by administering the vaccine to one or more suitable pigs in need thereof, then after an appropriate length of time (e.g., 4 weeks), challenging with a large sample ($10^{(3-7)}$TCID$_{(50)}$) of a biologically pure PRRSV isolate. A blood sample is then drawn from the challenged pig after about one week, and an attempt to isolate the virus from the blood sample is then performed. Isolation of a large amount of the virus is an indication that the vaccine may not be effective, while isolation of reduced amounts of the virus (or no virus) is an indication that the vaccine may be effective.

Thus, the effectiveness of the present vaccine may be evaluated quantitatively (i.e., a decrease in the percentage of consolidated lung tissue as compared to an appropriate control group) or qualitatively (e.g., isolation of PRRSV from blood, detection of PRRSV antigen in a lung, tonsil or lymph node tissue sample by an immunoassay). The symptoms of the porcine reproductive and respiratory disease may be evaluated quantitatively (e.g., temperature/fever) or semi-quantitatively (e.g., the presence or absence of one or more symptoms or a reduction in severity of one or more symptoms, such as cyanosis, pneumonia, lung lesions etc.).

An unaffected pig is a pig which has either not been exposed to a porcine reproductive and respiratory disease infectious agent, or which has been exposed to a porcine reproductive and respiratory disease infectious agent but is not showing symptoms of the disease. An affected pig is one which shows symptoms of PRRS or from which PRRSV can be isolated.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta, Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 pg/ml Quil A, 100 [mgr]g/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 .mu.g/ml Quil A, and 50 .mu.g/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: Drugs and the Pharmaceutical Sciences, Vol. 45, M. Dekker, N.Y., which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. Nos. 3,137,631; 3,959,457; 4,205,060; 4,606,940; 4,744,933; 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. Nos. 4,016,100; 4,452,747; 4,921,706; 4,927,637; 4,944,948; 5,008,050; and 5,009,956, all of which are incorporated herein by reference.

An effective amount of any of the above-described vaccines can be determined by conventional means, starting with a low dose of virus, viral protein plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies (see, for example, Examples 2 and 3 below).

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, protein, infectious DNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 mg to about 100 mg, more preferably from about 1 mg to about 10 mg, even more preferably from about 10 mg to about 1 mg. The dose amount of an infectious DNA molecule of the present invention in a vaccine of the present invention preferably ranges from about 0.1 mg to about 100 mg, more preferably from about 1 mg to about 10 mg, even more preferably from about 10 mg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

Suitable doses for viral protein or peptide vaccines according to the practice of the present invention range generally from 1 to 50 micrograms per dose, or higher amounts as may be determined by standard methods, with the amount of adjuvant to be determined by recognized methods in regard of each such substance. In a preferred example of the invention relating to vaccination of swine, an optimum age target for the animals is between about 1 and 21 days, which at pre-weening, may also correspond with other scheduled vaccinations such as against *Mycoplasma hyopneumoniae* or PCV. Additionally, a preferred schedule of vaccination for breeding sows would include similar doses, with an annual revaccination schedule.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. By way of example, vaccines may be delivered orally, parenterally, intradermally, subcutaneously, intramuscularly, intranasally or intravenously. Oral delivery may encompass, for example, adding the compositions to the feed or drink of the animals. Factors bearing on the vaccine dosage include, for example, the weight and age of the pig.

The present invention further provides a method of preparing a vaccine comprising a PRRS virus, infectious RNA molecule, plasmid, or viral vector described herein, which method comprises combining an effective amount of one of the PRRS virus, infectious RNA molecule, plasmid, or viral vector of the present invention, with a carrier acceptable for pharmaceutical or veterinary use.

In addition the live attenuated vaccine of the present invention can be modified as described in U.S. Pat. No. 6,500,662 to encode a heterologous antigenic epitope which is inserted into the PRRS viral genome using known recombinant techniques. See also U.S. Pat. No. 7,132,106 which is incorporated by reference in its entirety. Antigenic epitopes useful as heterologous antigenic epitopes for the present invention include antigenic epitopes from a swine pathogen other than PRRS virus which include, but are not limited to, an antigenic epitope from a swine pathogen selected from the group consisting of porcine parvovirus, porcine circovirus, a porcine rotavirus, swine influenza, pseudorabies virus, transmissible gastroenteritis virus, porcine respiratory coronavirus, classical swine fever virus, African swine fever virus, encephalomyocarditis virus, porcine paramyxovirus, torque teno virus, *Actinobacillus pleuropneumoniae*, *Actinobacillus suis*, *Bacillus anthraci*, *Bordetella bronchiseptica*, *Clostridium haemolyticum*, *Clostridium perfringens*, *Clostridium tetani*, *Escherichia coli*, *Erysipelothrix rhusiopathiae*, *Haemophilus parasuis*, *Leptospira* spp., *Mycoplasma hyopneumoniae*, *Mycoplasma hyorhinis*, *Mycoplasma hyosynovia*, *Pasteurella multocida*, *Salmonella choleraesuis*, *Salmonella typhimurium*, *Streptococcus equismilis*, and *Streptococcus suis*. Nucleotide sequences encoding antigenic epitopes from the aforementioned swine pathogens are known in the art and can be obtained from public gene databases on the worldwide web, such as at Genbank from the (USA) National Center for Biotechnology Information.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. It will be clear that the invention may be practiced otherwise than as particularly described in the foregoing description and examples.

Numerous modifications and variations of the present invention are possible in light of the above teachings and, therefore, are within the scope of the invention.

The following examples are intended to illustrate but not limit the invention.

Example 1

Adaptation and Attenuation of PRRSV Isolate P129 to PK-9 Cells

Virulent PRRS isolate P129 was isolated from a sick pig in Indiana in 1995 at the Animal Disease Diagnostic Laboratory of Purdue University. A serum sample from this pig was passaged once in a high health status pig to expand serum and lung homogenate stocks. Viral RNA was extracted from the serum and lung homogenate and used to determine the complete genome consensus sequence of P129 passage 0 virus. RNA was first primed with random hexamers and used to synthesize cDNA. The genome was amplified in three overlapping pieces using high fidelity (proofreading) PCR. The PCR products from three separate PCR reactions (per genome segment) were T/A cloned and used for DNA sequencing to generate a full length genome consensus sequence (see SEQ ID NO:1).

An aliquot of the same pig serum used for DNA sequencing, containing P129 passage 0, was used to infect primary porcine alveolar macrophage (PAM) cells. The progeny virus from the PAM infection (passage 1) was filtered through a 0.1 micrometer syringe filter and used to infect PK-9 cells.

PK-9 cells are a transgenic cell line derived by stably transfecting the PK0809 porcine kidney cell line with a plasmid encoding a deleted version of the porcine CD163 gene and the neomycin resistance gene. Details of the construction and characterization of the PK-9 cell line have been described previously.

Adaptation of the passage 1 virus from PAM cells to growth on PK-9 cells was difficult, and required several attempts with multiple parallel lineages. Infection was monitored by immunofluorescence of duplicate wells using FITC-conjugated monoclonal antibody SDOW17 specific for the viral nucleocapsid protein (Rural Technologies Inc, Brookings S. Dak.). Early passages resulted in a few small foci, but did not generate enough cell-free virus particles to initiate infection of a fresh monolayer. These passages were accomplished by treating the infected monolayer with Accutase (a trypsin substitute) and reseeding the cells in multiple wells with fresh medium, with or without the addition of non-infected PK-9 cells. After several such passages, some lineages showed a clear increase in the frequency and size of fluorescent foci. Some of these had acquired the ability to be passaged using cell-free virus fluids. By passage 17 (1 on PAM cells, 16 on PK-9), one lineage could reliably be sustained using dilutions of the cell-free fluids from the previous passages, and resulted in the infection of the entire monolayer within a few days. The virus did not cause cytopathic effect on PK-9 cells at any passage level. RNA was extracted from infected PK-9 cells at virus passage 17 and used to construct an infectious cDNA clone.

Example 2

Construction of an Infectious cDNA Clone of P129-PK Passage 17

An infectious cDNA clone of the P129-PK passage 17 virus was constructed, using a backbone plasmid as previously described. The genome of the virus was amplified by reverse transcription and PCR in three overlapping segments, with naturally occurring unique restriction endonuclease sites in the regions of overlap. The products from three separate PCR reactions were cloned and sequenced, and aligned to generate a consensus sequence for each genome segment. If none of the three cloned products of a given segment matched the predicted amino acid sequence of the consensus for that segment, one of the clones was modified by subcloning and/or site-directed mutagenesis until it matched the predicted amino acid sequence of the consensus. The three genome segments and the plasmid backbone were joined using standard cloning techniques and restriction endonuclease sites. The resulting full-length clone, designated pCMV-S-P129-PK17-FL, was infectious when transfected into PK-9 cells. The sequence of this infectious cDNA clone is given in SEQ ID NO:2. The genome is essentially identical to the passage 17 virus from which it was constructed, with authentic termini, and lacks any insertions or deletions relative to the consensus sequences of passage 17. There are no engineered restriction sites or other targeted changes within the viral genome of this infectious cDNA clone.

Nucleotide and amino acid differences between the complete genome consensus sequences of P129 passage 0 and the genome sequence of infectious clone pCMV-S-P129-PK17-FL are listed individually in Table 6. Table 6 includes all nucleotide differences and resulting amino acid differences by genome position. A subset of these mutations are responsible for the change in phenotype from IFN inhibitory (passage 0) to IFN non-inhibitory (all viruses derived from the passage 17 infectious cDNA clone). Table 7 summarizes nucleotide, amino acid, and non-conserved amino acid differences by PRRSV open reading frame (ORF) or non-structural protein (nsp). For the purposes of Table 7, the following groups of amino acids are among those considered conserved: [K, R], [D, E], [L, I, V, A], and [S, T].

Example 3

Deletion Mutants in P129-PK Passage 17

Deletions in two areas of the genome were engineered into infectious cDNA clone pCMV-S-P129-PK17-FL, to generate five genetically modified infectious clones.

One area of the genome to undergo modification was the nuclear localization sequence (NLS) located at amino acid positions 41-47 of the nucleocapsid protein (encoded by PRRSV ORF 7). Two types of deletions were made. These deletions have been described previously within the context of another PRRSV infectious clone. The wild type sequence of amino acid residues 41-49 is PG . . . KN. In mutant "d43/44", also known as "PG-KS", lysine residues 43 and 44 are deleted and asparagine residue 49 is changed to a serine. In mutant "d43l44l46", also known as "PG-S-KS", lysine residues 43, 44, and 46 are deleted and asparagine residue 49 is changed to a serine. The infectious clones derived from pCMV-S-P129-PK17-FL that incorporate these deletions are pCMV-S-P129-PK17-d43/44 and pCMV-S-P129-PK17-d43/44/46 respectively. See U.S. Pat. No. 7,544,362.

The second area of the genome to undergo modification was in the hypervariable region of nsp2, within ORF1a. A deletion of 131 amino acids (393 nucleotides) has been described previously within the context of another PRRSV infectious clone. The infectious clone derived from pCMV-S-P129-PK17-FL that incorporate this deletion is pCMV-S-P129-PK17-nsp2.

Infectious clones that combine the NLS and nsp2 deletions were also generated within the pCMV-S-P129-PK17-FL backbone, and these were designated pCMV-S-P129-PK17-nsp2-d43/44 and pCMV-S-P129-PK17-nsp2-d43/44/46.

Example 4

Generation and Growth of Viruses on PK-9 Cells

The six infectious clones described in Example 3 were transfected into PK-9 cells to generate the six viruses as shown in Table 1. Virus was generated from these infectious clones by direct transfection of the circular plasmid into PK-9 cells using Lipofectamine 2000. Following transfection, recovered viruses were again serially passaged on PK-9 cells in order to further increase titers and attenuate virulence. Stocks were made for in vitro testing and in vivo evaluation as vaccine candidates. In the case of P129-PK17-FL virus derived from the non-modified pCMV-S-P129-PK17-FL infectious clone, the virus was cultured until reaching a total of 52 passages from the pig. The complete genome of this virus was sequenced at passages 24 (SEQ ID NO: 3) and 52 (SEQ ID NO:6).

Example 5

Viruses Derived from the P129-PK Passage 17 Infectious cDNA Clone have Reduced Ability to Inhibit IFN-Alpha Induction Viruses and cells. MARC-145 and ST cells were grown in modified Eagle's medium (MEM) supplemented with 5% fetal bovine serum (FBS) and antibiotics (50 µg/ml gentamicin, 100 UI penicillin and 100 µg/ml streptomycin). The porcine alveolar macrophage ZMAC-1 cells were grown in RPMI-1640 supplemented with 10% FBS. TGE virus strain Purdue was prepared by infection of confluent ST cell monolayers at a multiplicity of 0.01 in modified Eagle's medium. The virus inoculum was removed after 1 h and cells were incubated in MEM supplemented with 2.5% FBS at 37° C. in a 5% $CO_2$ atmosphere. Virus was released by freezing and thawing the cell monolayers after 80% cytopathic effect was observed. The TGE viral stock was centrifuged at 3,500 rpm for 15 min at 4° C. and stored at −80° C. until use. Virus stocks (from PK-9 cells) were as follows: P129-PK-FL and P129-PK-dnsp2-d43/44/46 were at passage 8/25 (8 from the infectious clone, 25 from the pig). The other four viruses (P129-PK-d43/44, P129-PK-d43/44/46, P129-PK-dnsp2, and P129-PK-dnsp2-d43/44) were at passage 21/38. Working stocks of various PRRS viruses were prepared by making a single passage on ZMAC-1 cells, except that commercial vaccines Ingelvac PRRS MLV and Ingelvac PRRS ATP were reconstituted according to the manufacturer's instructions and used directly for infection.

Isolation of porcine PBMC. Fresh heparinized venous blood was diluted with Hank's and PBMC were isolated by density centrifugation through Ficoll-Hypaque 1077 (Sigma) gradient. After being washed twice in Hank's, the cells were suspended in RPMI medium with L-glutamine (Mediatech) supplemented with 5% fetal bovine serum (Gibco), 100 U/ml penicillin, 0.1 mg/ml streptomycin, 1 mM sodium pyruvate, 1× nonessential amino acids (Mediatech) 100 U/ml gentamicin and 250 mM 2-mercaptoethanol (Sigma).

Purification of porcine plasmacytoid dendritic cells. The purification of porcine plasmacytoid dendritic cells was done as previously described (Calzada-Nova, submitted), and was based on the characteristic expression of CD4 and CD172 by these cells (Summerfield et al., 2003) Briefly, fresh porcine PBMC were suspended in PBS with 0.5% BSA and labeled with optimal amounts of mAb recognizing porcine CD172 (74-22-15, VMRD). Following one wash, the cells were then incubated with secondary goat anti-mouse antibody conjugated to PE (Southern Biotech) and after washing, with FITC labeled anti-CD4 (74-12-4, VMRD). PDCs were sorted on a Reflection Cell Sorter (iCyt), sort gates were set on the $CD4^+/CD172^{low}$ population. After the sort the purity of the cells was confirmed by reanalysis. In all cases, the purity was >95%.

Assay for measurement cytokine secretion. PBMC or PDC were stimulated for 16 h (37° C., 5% $CO_2$) with the different stimulants or were mock-stimulated. After incubation, medium overlaying the stimulated cells was assayed for the presence of IFN-α using a sandwich ELISA prepared with monoclonal antibodies available commercially (anti-pig IFN-α mAbs K9 and F17). Briefly, Immulon II plates (Dynatech Inc.) were coated with anti-porcine IFN-α mAb F17 (PBL Laboratories) by overnight incubation at 4° C. followed by blocking with RPMI medium supplemented with 5% fetal bovine serum. After 1 hour the medium was discarded and fifty microliters of the supernatant to be tested added to the assay wells in duplicate. After a 1 h incubation the assay wells were washed 4 times and then incubated sequentially with biotin-labeled, anti-porcine IFN-α mAb K9 (PBL Laboratories), HRP-conjugated streptavidin (Zymed Laboratories), and TMB substrate (KPL). The optical density was determined with an ELISA plate reader.

Viruses derived from the P129-PK passage 17 infectious cDNA clone lack the ability to inhibit IFN-alpha induction. Working virus stocks were prepared from of a group of four different PRRS wild-type virus isolates (P3412, P129, IND5, NADC20) utilizing the porcine alveolar macrophage cell line ZMAC-1. Additional stocks were also prepared from derivatives of the first two wild-type viruses which had been adapted to grow in cell culture by repeated passage in PK-9, FK.D4 or MARC-145 cells. Three of the four wild-type isolates (P129, IND5, NADC20) grew readily and efficiently in the ZMAC-1 cells to titers of about $10^7$ TCID$_{50}$/ml, while the P3412 wild-type isolate reached a titer of only $10^5$ TCID$_{50}$/ml. Notably, stocks of P129 viruses prepared in the ZMAC-1 cell line reached 10-fold higher titers than those obtained in the PK-9 or MARC-145 cells to which the viruses were adapted. Examination of the ability of these viruses to stimulate IFN-α secretion by PBMC revealed that with one exception (isolate P3412 clone C), a very small amount (<50 pg) of IFN-α was secreted by these cells in response to their exposure to any of the PRRS virus stocks tested, which is negligible by comparison to the abundant secretion of IFN-α (17,540 pg) produced by the same cells as a result of their exposure to the porcine coronavirus, transmissible gastroenteritis virus (TGEv).

PRRSV is not only unable to stimulate IFN-α production by porcine PBMC but actively inhibits its production. The inhibitory effects of the PRRSV stocks were determined by measuring the amount of IFN-α secreted by PBMC in response to exposure to TGEv in the presence or absence of PRRSV. As shown in Table 2, all 4 of the wild-type PRRS virus isolates tested, as well as all of the cell culture adapted derivatives, exhibited a strong inhibitory effect (>80%) on the IFN-α response of PBMC to TGEv. The analysis of a group of virus stocks derived from an infectious cDNA clone (pCMV-S-P129-PK17-FL), including full-length P129-PK-FL virus and several genetically engineered deletion mutants was conducted. As shown in Table 3, when compared to the strong inhibitory effect (95%) of the parental wild-type isolate P129 (passage 1), the P129-PK-FL virus and all deletion mutants exhibited a significantly reduced ability to inhibit the induction of IFN-☐ by TGEv in PBMC. To further evaluate the IFN-α phenotype of these viruses, subsequent experiments were focused on performing direct comparisons between the P129-PK-FL and P129-PK-d43/44 viruses, the parental P129 wild-type strain, and/or two commercially available modified live PRRSV vaccines produced by Boehringer Ingelheim (Ingelvac PRRS MLV and Ingelvac PRRS ATP). An additional low-passage reference isolate, NVSL-14, was also tested. As shown in Table 4, in four independent experiments, P129-PK-FL and P129-PK-d43/44 exhibited significantly lesser IFN-α inhibitory effect than the parental P129 virus, the two Ingelvac attenuated strains, or the reference strain. In one instance, co-infection with the P129-PK-FL or P129-PK-d43/44 viruses resulted in an apparent enhancement of the IFN-α response to TGEv.

The results shown in Table 2 are indicative of the interferon-α inhibitory effect of wild-type PRRS virus and derivatives adapted to growth in cell culture. The indicated PRRS virus stocks, were grown in ZMAC-1 cells and the titer of these newly generated stocks determined using ZMAC-1 cells. The amount of IFN-α present in culture supernatants of porcine peripheral blood mononuclear cells exposed for 18 h to the indicated PRRS virus stock in the presence or absence of TGE virus was determined by ELISA. *Response to TGEv alone.

The results shown in Table 3 demonstrate the interferon-α inhibitory effect of wild-type PRRS virus P129 and its genetically engineered derivatives adapted to grow in CD163-expressing PK-9 cells. The amount of IFN-α present in culture supernatants of porcine peripheral blood mononuclear cells (PBMC) exposed for 18 h to the indicated PRRS virus stock in the presence or absence of TGE virus was determined by ELISA. na=not applicable; *Response to TGEv alone.

Table 4 shows decreased interferon-α inhibitory effect of the P129-PK-FL and P129-PK-d43/44 viruses as compared to the wild-type P129 virus and the PRRS Ingelvac vaccines. The amount of IFN-α present in culture supernatants of porcine peripheral blood mononuclear cells (PBMC) exposed for 18 h to the indicated PRRS virus stock in the presence or absence of TGE virus was determined by ELISA. na=not applicable; *Response to TGEV alone.

The plentiful amount of IFN-α secreted by PBMC in response to their exposure to TGEV is derived primarily from a subset of cells that comprise less than 0.3% of the PBMC population. This infrequent but important cell subset is composed of plasmacytoid dendritic cells (PDCs), which received this name due to characteristic plasmacytoid morphology. To further examine the IFN-α phenotype of the P129-PK-FL and the P129-PK-d43/44 viruses, a series of experiments was performed similar to those described above, except that PDC freshly isolated from PBMC to a >95% purity were utilized. As shown in FIG. 1, this series of experiments confirmed that the P129-PK-FL and P129-PK-d43/44 viruses caused negligible inhibition of IFN-α induction by TGEV. Furthermore, in one experiment an apparent enhancing effect was observed on TGEV-mediated IFN-α induction by PDCs in response to P129-PK-FL and P129-PK-d43/44 PRRS viruses. In contrast, the Ingelvac PRRS MLV virus exhibited a strong inhibitory effect on the IFN-α response, as shown in FIG. 1.

The results described in the experimental section reveal that the P129-PK-FL and P129-PK-d43/44 PRRS viruses, as well as other derivatives of the pCMV-S-P129-PK17-FL infectious cDNA clone, have a greatly reduced ability to inhibit the induction of IFN-α by TGEV in infected PBMC or PDC cells. This is in marked contrast to the IFN suppressive effect observed with wild-type (low-passage) PRRS viruses and with two commercially available modified live virus vaccines (Ingelvac PRRS MLV and Ingelvac PRRS ATP). The observation that the P129-PK-FL and P129-PK-d43/44 viruses were minimally suppressive of this important function of PDCs is potentially significant given the major role that these cells play in mediating innate immunity against virus infections.

It should also be noted that the present invention provides clinically effective commercial vaccine viruses adapted to grow on permissive cells that recombinantly express CD163 receptor, and that such viruses and vaccines are not dependent on, nor were developed at any point with, historical "simian cell" culturing technology. See specifically U.S. Pat. No. 7,754,464.

Example 6

Safety and Efficacy of Vaccine Candidates

In order to evaluate their safety and efficacy as vaccines against PRRS, three of the viruses derived from the pCMV-S-P129-PK17-FL infectious cDNA clone, P129-PK-FL (passage 7/24), P129-PK-d43/44 (passage 17/34) and P129-PK-d43/44/46 (passage 17/34) were evaluated in a young pig respiratory disease model. The origin of these viruses is shown in FIG. 8, and the experimental design (treatment groups) are listed in Table 5. Low passage virulent PRRSV isolate NADC20 was used for heterologous challenge at 7 weeks of age (four week past vaccination). Control treatment groups included mock vaccine and commercial PRRS vaccine Ingelvac MLV.

Non-treated (NT) groups were as follows: NT1 pigs were sentinels to monitor the health status of source pigs. They were housed separately and were necropsied prior to PRRSV challenge. NT2 pigs were contact controls housed separately in a pen between the two pens of vaccinated pigs, a total of two per treatment group for each T02 thru T05. NT3 pigs were contact controls housed one per pen with vaccinated pigs, a total of two per treatment group (T01 thru T05). Only NT3 pigs were assigned to the T01 group.

Rectal temperatures of vaccinated animals were measured post-vaccination and compared to the T01 (mock vaccine) treatment group. The results are shown in FIG. 1. None of the vaccines induced fevers. All groups averaged less than 104° C. throughout the post-vaccination observation period.

Figure 2:
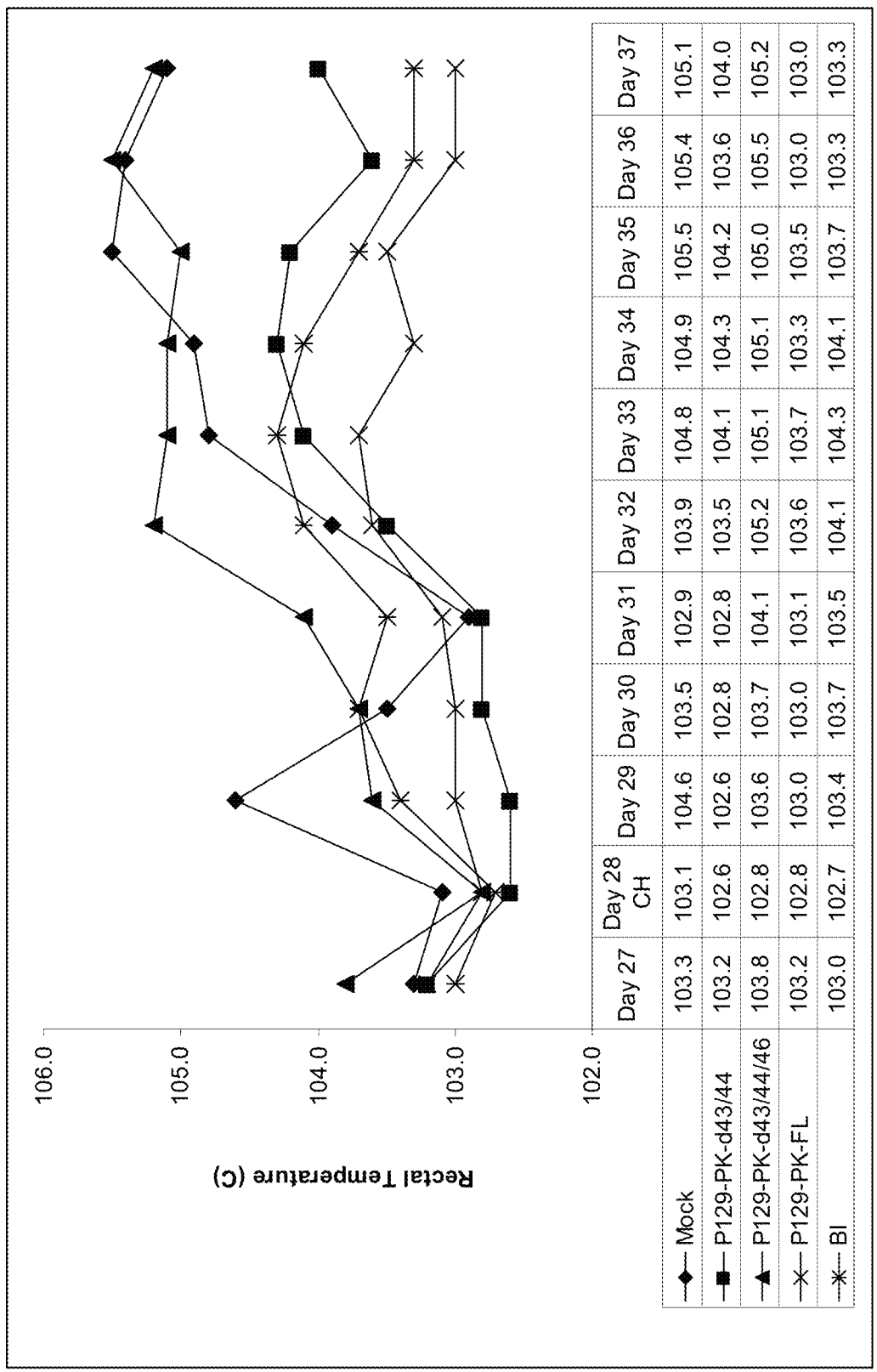
FIG. 2 shows rectal temperatures post-challenge with virulent PRRSV NADC20.

Rectal temperatures of pigs were measured post-challenge. The results are shown in FIG. 2. Unvaccinated T01 pigs showed sustained fevers of greater than 104° C. In contrast, three of the vaccines significantly reduced post-challenge fevers. P129-PK-FL was most effective at reducing fevers.

Figure 3:
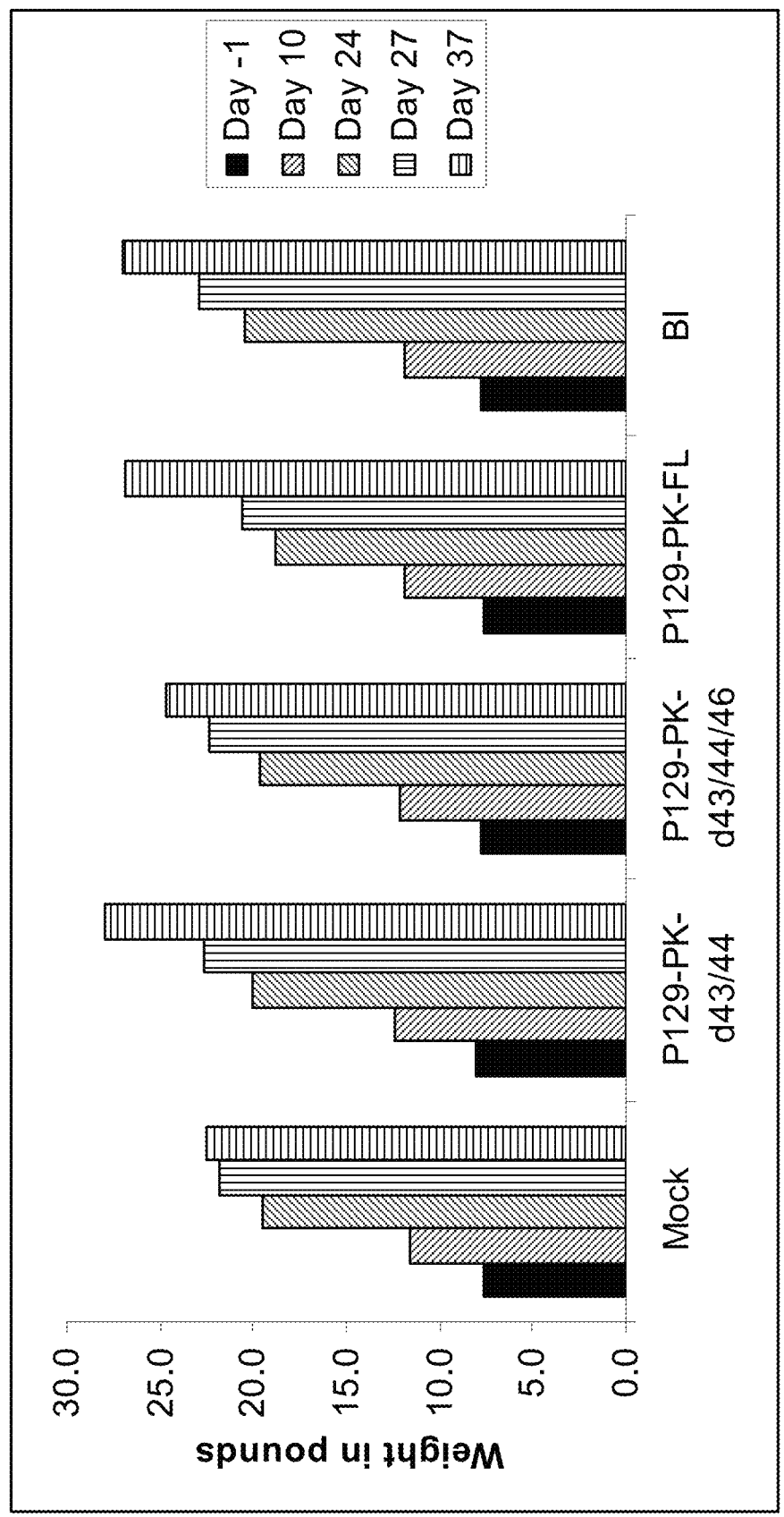
FIG. 3 shows body weights post-vaccination and post-challenge.

The body weight of animals was recorded pre- and post-vaccination. The results are shown in FIG. 3. Body weights were recorded on days −1 (prior to vaccination), 10, 24, 27 (prior to challenge), and 37 of the study. In unvaccinated pigs, challenge with virulent NADC20 virus almost completely eliminated weight gain during the 10 day observation period. The vaccines negated this effect to various degrees.

Figure 4:
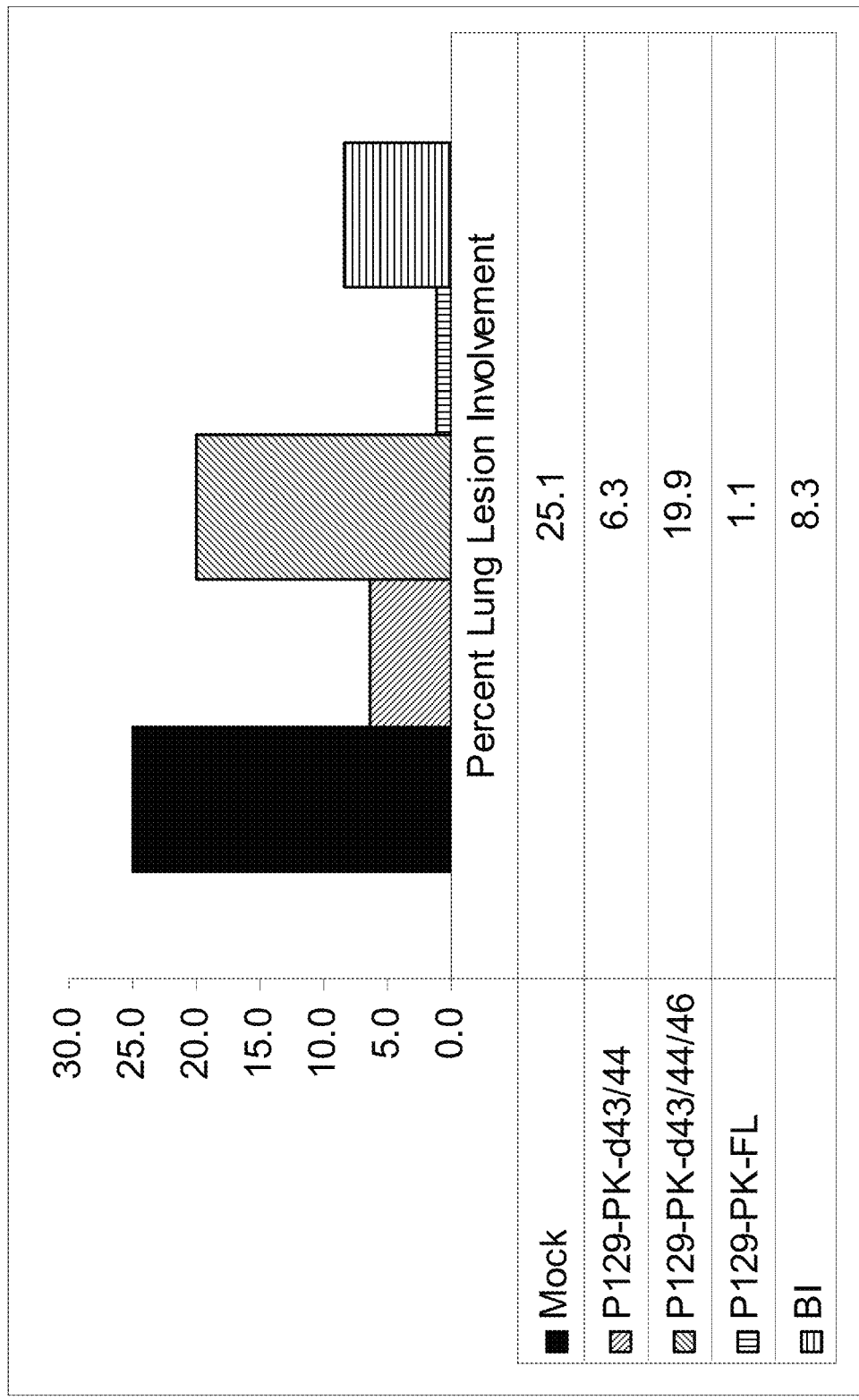
FIG. 4 shows post-challenge data for percentage of lungs with PRRS lesions.

The lungs of challenged animals were examined at necropsied post-challenge. The percentages of each lung involved in lesions are shown in FIG. 4. The T01 mock vaccine group averaged 25.1% lung lesion involvement. The vaccines reduced lung lesions to various degrees. P129-PK-FL was most efficacious, reducing lung lesion involvement to 1.1%.

Figure 5:
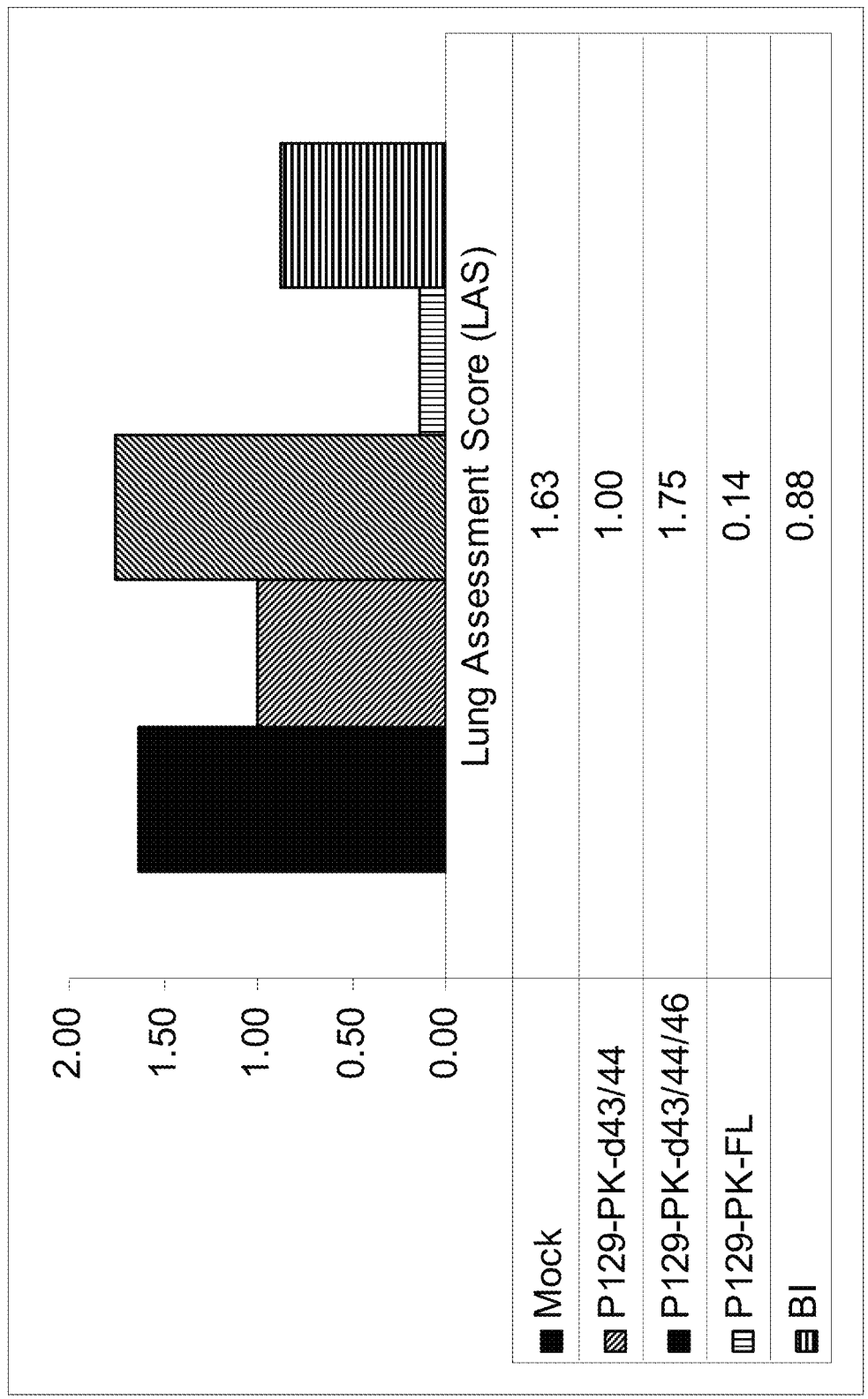
FIG. 5 shows post-challenge lung assessment scores (LAS) for severity of lesions observed.

The severity of the lung lesions was evaluated using a lung assessment score (LAS) as shown in FIG. 5. Three of the vaccines reduced LAS. P129-PK-FL reduced the mean LAS from 1.63 in the mock vaccinated group to 0.14.

Figure 6:
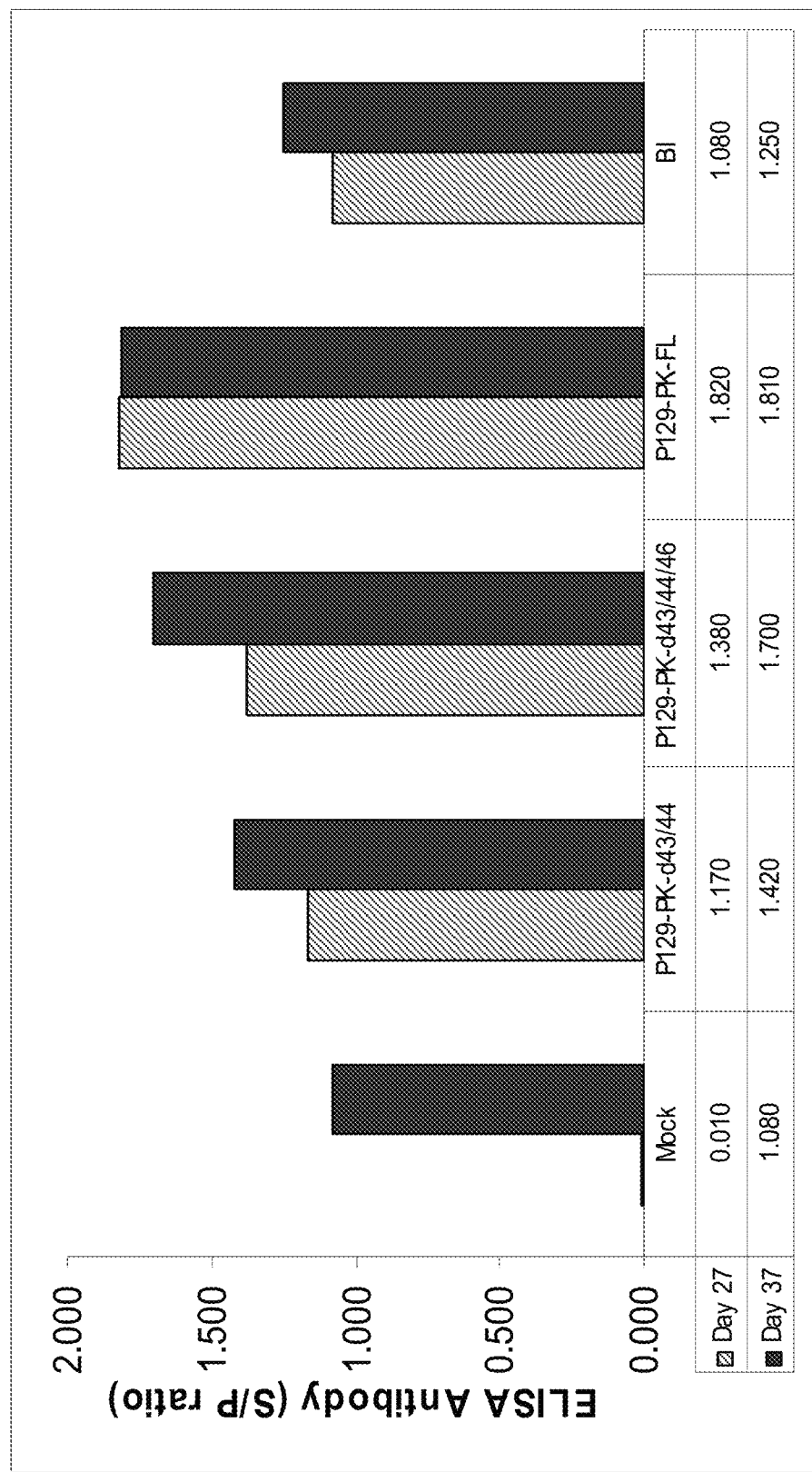
FIG. 6 is a histogram that depicts the anti-PRRSV antibody levels in serum post-vaccination and post-challenge (ELISA S/P ratios).

Serum antibodies to PRRSV were induced by both vaccination and challenge. The IDEXX ELISA S/P ratios were measured on days 27 and 37 of the study. The results are shown in FIG. 6. Vaccination with P129-PK-FL induced the highest levels of anti-PRRS antibodies.

Viremia in the serum of challenged pigs was titrated on PAM cells. Results ($TCID_{50}$/mL) are given in FIG. 7. P129-PK-FL was most effective at reducing post-challenge viremia.

Although the invention has been described with reference to the above examples, and to Attachments, the entire content of each of which are incorporated by reference in their entireties, it will be understood that modifications and variations are encompassed within the spirit and scope of the invention. Accordingly, the invention is limited only by the following claims.

Example 7

Derivation of Infectious cDNA Clone pCMV-S-P129-PK17-FL from Infectious cDNA Clone pCMV-S-P129

The PRRSV infectious cDNA clone of the present invention pCMV-S-P129-PK17-FL can readily be derived from the previously described PRRSV infectious cDNA clone pCMV-S-P129 by one of ordinary skill in the art, using the technique of site-directed mutagenesis. PRRSV infectious cDNA clone pCMV-S-P129 is described in U.S. Pat. No. 6,500,662 and deposited with ATCC under accession number 203489. The DNA sequence of the PRRSV genome in this clone also available in the Genbank (NCBI) database as accession number AF494042. Site-directed mutagenesis kits are commercially available from a number of suppliers, and are capable of making numerous simultaneous nucleotide changes at multiple sites in large plasmids. Such kits include, but are not limited to, Change-IT™ Multiple Mutation Site Directed Mutagenesis Kit (Affymetrix/USB), QuikChange Lightning Multi Site-Directed Mutagenesis Kit (Agilent Technologies—Stratagene Products), and AMAP Multi Site-directed Mutagenesis Kit (MBL International).

A list of nucleotide changes between PRRSV infectious cDNA clone pCMV-S-P129 (available from ATCC) and the PRRSV infectious cDNA clone of the present invention pCMV-S-P129-PK17-FL is presented in Table 8. All changes are in the protein coding regions of the genome. There are a total of 74 nucleotide changes, which can be introduced into the pCMV-S-P129 infectious clone using 74 mutagenic primers and multiple sequential reactions with a commercial site-directed mutagenesis kit, yielding a plasmid molecule that is identical in sequence to pCMV-S-P129-PK17-FL described herein. In actuality, one can get the same result with fewer than 74 mutagenic primers, since clusters of mutations within about 50-60 nucleotides of each other can be changed using a single mutagenic primer. For example, nucleotides 735, 750, and 756 can be changed using a single mutagenic primer, as can nucleotides 965, 992, and 1009. Thus the number of primers is reduced to about 60.

Of the 74 nucleotide changes, the majority (42) are synonymous or "silent", meaning they encode the same amino acid. These nucleotide changes are unlikely to have any measurable effect on the interferon induction or inhibition phenotype of the virus. The remaining 32 nucleotide changes are non-synonymous or "non-silent", and result in amino acid changes in viral proteins. These 32 nucleotide changes are predicted to be directly responsible for the interferon induction/inhibition phenotype of the virus, and should be changed in order to convert the virus encoded by the infectious clone pCMV-S-P129 to the same interferon phenotype as the shown by the virus encoded by infectious clone pCMV-S-P129-PK17-FL. Such a change would require at most 32 mutagenic primers, less if one takes into account the clustering of some of the relevant nucleotides.

Example 8

De Novo Synthesis of Infectious cDNA Clone pCMV-S-P129-PK17-FL

As an alternative to site-directed mutagenesis, the PRRS viral genome of the present invention can be chemically synthesized de novo, with appropriate 5' and 3' adaptor sequences, and cloned into the plasmid backbone used for PRRS infectious cDNA clone pCMV-S-P129 (available from ATCC as accession number 203489) or a similar plasmid backbone. Custom synthesis of genes greater than 50 kb in length (the PRRSV genome is about 15.5 kb) is available as a commercial service from numerous vendors, including (but not limited to): GenScript, DNA 2.0, and Bio Basic Inc. The synthetic viral genome is directionally cloned into the pCMV-S vector by replacing the viral genome in the infectious clone pCMV-S-P129 using the 5' PacI and 3' SpeI restriction enzyme sites that flank the genome. In order to cut the synthetic genome, a 24-nucleotide extension (5'-GCAGAGCTCG<u>TTAATTAA</u>ACCGTC-genome-3', which includes the underlined PacI site) is built into the 5' end of the synthetic genome, and an 83-nucleotide extension (5'-genome-AAAAAAAAAAAAAAAAAAAAAAAATGCAT-ATTTAAATCCCAAGCCGAATTCCAGCACA CTGGCGGCCGTT<u>ACTAGT</u>GAGCGGCCGC-3', which includes the underlined SpeI site) is built into the 3' end of the synthetic genome. After cutting the plasmid and synthetic genome with PacI and SpeI, the appropriate fragments are purified, joined using DNA ligase, and transformed into *Escherichia coli* for screening and propagation using standard cloning techniques well known to persons of ordinary skill in the art.

TABLE 1

| Infectious clone | Virus |
|---|---|
| pCMV-S-P129-PK17-FL | P129-PK-FL |
| pCMV-S-P129-PK17-d43/44 | P129-PK-d43/44 |
| pCMV-S-P129-PK17-d43/44/46 | P129-PK-d43/44/46 |
| pCMV-S-P129-PK17-nsp2 | P129-PK-nsp2 |
| pCMV-S-P129-PK17-nsp2-d43/44/46 | P129-PK-nsp2-d43/44 |
| pCMV-S-P129-PK17-nsp2-d43/44/46 | P129-PK-nsp2-d43/44/46 |

TABLE 2

| SAMPLE | PRRS v stock | CLONE | Passage/Cell type | Estimated PRRS virus titer ($TCID_{50}$) in original stock | PRRS virus titer ($TCID_{50}$) in PRRS virus stocks generated in ZMAC-1 cells | IFN-α (ng/ml) produced by PBMC in response to PRRSv alone | IFN-α (ng/ml) produced by PBMC in response to PRSSv + TGEv | Inhibition of IFN-α response to TGEv (%) |
|---|---|---|---|---|---|---|---|---|
| 1 | P3412 | wt | 0 (serum) | nd | $10^5$ | <0.04 | <0.04 | 99 |
| 2 | P3412 | A | 41/PK | $10^3$ | $10^3$ | <0.04 | 1.166 | 93 |
| 3 | P3412 | C | 41/PK | $10^3$ | $10^3$ | 0.464 | 3.376 | 81 |
| 4 | P3412 | A | 43/FK | $10^5$ | $10^6$ | <0.04 | <0.04 | 99 |
| 5 | P3412 | B | 43/FK | $10^5$ | $10^5$ | <0.04 | 1.86 | 89 |
| 6 | P129 | wt | 0 (serum) | nd | $10^7$ | <0.04 | 0.327 | 98 |
| 7 | P129 | A | 63/PK | $10^4$ | $10^8$ | <0.04 | <0.04 | 99 |
| 8 | P129 | B | 63/PK | $10^4$ | $10^8$ | <0.04 | 2.3 | 87 |
| 9 | P129 | A | 60/FK | $10^5$ | $10^6$ | 0.05 | 2.151 | 88 |
| 10 | P129 | B | 60/FK | $10^5$ | $10^6$ | <0.04 | <0.04 | 99 |
| 11 | P129 | A-1 | 51/MARC | $10^5$ | $10^8$ | <0.04 | 0.686 | 96 |
| 12 | P129 | A-1 | 151/MARC | $10^5$ | $10^8$ | <0.04 | 0.04 | 99 |
| 13 | NADC 20 | wt | 0 (serum) | nd | $10^7$ | <0.04 | <0.04 | 99 |
| 14 | IND5 | wt | 0 (serum) | nd | $10^7$ | <0.04 | <0.04 | 99 |
| — | Mock | — | — | na | na | 0 | 17.54* | na |

TABLE 3

| Experiment | PRRS virus stock | IFN-α (ng/ml) produced by PBMC in response to PRRSv alone | IFN-□α (ng/ml) produced by PBMC in response to PRRSv + TGEv | Inhibition of TGEv induced IFN-α response (%) |
|---|---|---|---|---|
| 1 | P129 | 0.09 | 0.64 | 95 |
|  | P129-PK-FL | 0.53 | 7.37 | 38 |
|  | P129-PK-d43/44 | 0.85 | 8.59 | 28 |
|  | P129-PK-d43/44/46 | 1.01 | 7.65 | 36 |
|  | P129-PK-dnsp2d43/44 | 1.34 | 10.28 | 24 |
|  | P129-PK-dnsp2d43/44/46 | 0.38 | 8.28 | 31 |
|  | P129-PK-dnsp2 | 0.04 | 4.86 | 60 |
|  | Mock | na | 12.16* | na |

TABLE 4

| Experiment | PRRS virus stock | IFN-α (ng/ml) produced by PBMC in response to PRRSv alone | IFN-□α (ng/ml) produced by PBMC in response to PRRSv + TGEv | Inhibition of TGEv induced IFN-α response (%) |
|---|---|---|---|---|
| 1 | P129 | 0.04 | 9.75 | 81 |
|  | P129-PK-FL | 0.07 | 60.22 | 0 |

TABLE 4-continued

| Experiment | PRRS virus stock | IFN-α (ng/ml) produced by PBMC in response to PRRSv alone | IFN-□α (ng/ml) produced by PBMC in response to PRRSv + TGEv | Inhibition of TGEv induced IFN-α response (%) |
|---|---|---|---|---|
| | P129-PK-d43/44 | 0.13 | 70.10 | 0 |
| | Ingelvac PRRS | 0.04 | 13.05 | 74 |
| | Ingelvac PRRS ATP | 0.04 | 9.10 | 82 |
| | NVSL-14 | 0.01 | 13.35 | 74 |
| | Mock | na | 50.06* | na |
| 2 | P129-PK-FL | 0.126 | 13.52 | 26 |
| | P129-PK-d43/44 | 0.127 | 17.18 | 6 |
| | Ingelvac PRRS | 0.04 | 3.09 | 83 |
| | Ingelvac PRRS ATP | 0.04 | 3.11 | 83 |
| | Mock | na | 18.21* | na |
| 3 | P129-PK-FL | 0.04 | 8.28 | 6 |
| | P129-PK-d43/44 | 0.06 | 8.26 | 6 |
| | Ingelvac PRRS | 0.04 | 3.56 | 60 |
| | Ingelvac PRRS ATP | 0.04 | 4.15 | 53 |
| | Mock | na | 8.84* | na |
| 4 | P129-PK-FL | 0.05 | 12.97 | 7 |
| | P129-PK-d43/44 | 0.05 | 13.57 | 3 |
| | Ingelvac PRRS | 0.04 | 6.07 | 57 |
| | Ingelvac PRRS ATP | 0.04 | 5.30 | 62 |
| | Mock | na | 13.95* | na |

TABLE 5

| TX | IVP | Passage or Serial # | Cell Line | Regimen | Volume per IM Dose | # of Pigs |
|---|---|---|---|---|---|---|
| NT1* | NA | NA | NA | NA | NA | 3 |
| NT2* | NA | NA | NA | NA | NA | 8 |
| NT3* | NA | NA | NA | NA | NA | 10 |
| T01 | Mock | NA | NA | Day 0 | 2 mL | 12 |
| T02 | P129-PK-d43/44 | 17/34 | PK9 | Day 0 | 2 mL | 12 |
| T03 | P129-PK-d43/44/46 | 17/34 | PK9 | Day 0 | 2 mL | 12 |
| T04 | P129-PK-FL | 7/24 | PK9 | Day 0 | 2 mL | 12 |
| T05 | BI (Ingelvac MLV) | NA | Monkey kidney | Day 0 | 2 mL | 12 |

TABLE 6

| Genome position | Passage 0 nucleotide | Passage 17 nucleotide | Affected viral protein | Amino acid position | Passage 0 amino acid | Passage 17 amino acid |
|---|---|---|---|---|---|---|
| 407 | C | T | Nsp1a | 72 | P | P |
| 612 | C | T | Nsp1a | 141 | H | Y |
| 735 | G | A | Nsp1b | 2 | D | N |
| 750 | A | G | Nsp1b | 7 | S | G |
| 756 | G | A | Nsp1b | 9 | D | N |
| 992 | A | T | Nsp1b | 87 | E | D |
| 1009 | G | A | Nsp1b | 93 | C | Y |
| 1096 | C | A | Nsp1b | 122 | P | H |
| 1215 | C | T | Nsp1b | 162 | L | L |
| 1620 | G | A | Nsp2 | 94 | A | T |
| 1786 | C | A | Nsp2 | 149 | T | K |
| 1793 | C | T | Nsp2 | 151 | G | G |
| 1808 | T | C | Nsp2 | 156 | D | D |
| 1841 | C | T | Nsp2 | 167 | C | C |
| 2106 | A | G | Nsp2 | 256 | I | V |
| 2164 | T | G | Nsp2 | 275 | M | R |
| 2185 | T | C | Nsp2 | 282 | M | T |
| 2318 | A | G | Nsp2 | 326 | S | S |
| 2403 | G | T | Nsp2 | 355 | V | L |
| 2591 | G | A | Nsp2 | 417 | L | L |
| 2804 | C | T | Nsp2 | 488 | D | D |
| 3019 | A | G | Nsp2 | 560 | Y | C |
| 3074 | T | C | Nsp2 | 578 | S | S |
| 3167 | C | T | Nsp2 | 609 | D | D |
| 3214 | G | A | Nsp2 | 625 | R | K |
| 3563 | C | T | Nsp2 | 741 | I | I |
| 3740 | A | G | Nsp2 | 800 | A | A |
| 4154 | T | C | Nsp2 | 938 | C | C |
| 4477 | A | C | Nsp3 | 72 | K | T |
| 4643 | A | G | Nsp3 | 127 | V | V |
| 4705 | T | C | Nsp3 | 148 | V | A |
| 4736 | C | T | Nsp3 | 158 | P | P |
| 5231 | C | T | Nsp3 | 323 | I | I |
| 5324 | C | T | Nsp3 | 354 | L | L |
| 5393 | G | A | Nsp3 | 377 | L | L |
| 5498 | A | G | Nsp3 | 412 | L | L |
| 5851 | C | A | Nsp4 | 84 | A | E |
| 5855 | T | C | Nsp4 | 85 | D | D |
| 5909 | C | T | Nsp4 | 103 | V | V |
| 5917 | G | A | Nsp4 | 106 | S | N |
| 5985 | C | A | Nsp4 | 129 | L | I |
| 6505 | C | T | Nsp5 | 98 | A | V |
| 6644 | T | C | Nsp5 | 144 | F | F |
| 6653 | T | C | Nsp5 | 147 | R | R |
| 7419 | G | A | Nsp7 | 217 | D | N |
| 8032 | A | G | Nsp9 | 162 | A | A |
| 8074 | C | T | Nsp9 | 176 | G | G |
| 8200 | A | G | Nsp9 | 218 | G | G |
| 8593 | T | C | Nsp9 | 349 | P | P |
| 8831 | G | A | Nsp9 | 429 | V | I |
| 8911 | T | C | Nsp9 | 455 | N | N |
| 9160 | A | G | Nsp9 | 538 | E | E |
| 9568 | A | G | Nsp9 | 674 | L | L |
| 9714 | T | C | Nsp10 | 38 | I | T |
| 10,271 | C | T | Nsp10 | 224 | L | L |
| 10,627 | T | C | Nsp10 | 342 | V | V |
| 11,265 | G | A | Nsp11 | 114 | G | E |
| 11,512 | T | C | Nsp11 | 196 | S | S |
| 11,913 | T | C | Nsp12 | 107 | I | T |
| 12,487 | A | T | ORF2a | 144 | E | V |
| 12,876 | C | T | ORF3 | 66 | A | V |
| 12,949 | A | G | ORF3 | 90 | L | L |
| 13,575 | G | A | ORF4 | 117 | V | V |
| 13,857 | T | G | ORF5 | 29 | V | G |
| 13,869 | A | G | ORF5 | 33 | N | S |
| 13,872 | C | G | ORF5 | 34 | T | S |
| 14,102 | G | A | ORF5 | 111 | V | I |
| 14,143 | C | T | ORF5 | 124 | V | V |
| 14,257 | G | A | ORF5 | 162 | E | E |
| 14,287 | C | T | ORF5 | 172 | N | N |
| 14,379 | T | C | ORF6 | 7 | D | D |
| 14,546 | T | C | ORF6 | 63 | V | A |
| 14,578 | A | G | ORF6 | 74 | T | A |
| 14,780 | C | T | ORF6 | 141 | T | I |
| 14,932 | A | G | ORF7 | 20 | N | N |
| 14,973 | G | A | ORF7 | 34 | S | N |
| 15,124 | T | C | ORF7 | 84 | N | N |
| 15,288 | G | A | 3'UTR | — | — | — |

TABLE 7

| ORF or nsp | Nucleotide differences | Amino acid differences | Non-conservative amino acid differences |
|---|---|---|---|
| Nsp1a | 2 | 1 | 1 |
| Nsp1b | 7 | 6 | 5 |
| Nsp2 | 19 | 8 | 5 |

TABLE 7-continued

| ORF or nsp | Nucleotide differences | Amino acid differences | Non-conservative amino acid differences |
|---|---|---|---|
| Nsp3 | 8 | 2 | 1 |
| Nsp4 | 5 | 3 | 2 |
| Nsp5 | 3 | 1 | 0 |
| Nsp6 | 0 | 0 | 0 |
| Nsp7 | 1 | 1 | 1 |
| Nsp8 | 0 | 0 | 0 |
| Nsp9 | 8 | 1 | 0 |
| Nsp10 | 3 | 1 | 1 |
| Nsp11 | 2 | 1 | 1 |
| Nsp12 | 1 | 1 | 1 |
| ORF2a | 1 | 1 | 1 |
| ORF2b | 0 | 0 | 0 |
| ORF3 | 2 | 1 | 0 |
| ORF4 | 1 | 0 | 0 |
| ORF5 | 7 | 4 | 2 |
| ORF6 | 4 | 3 | 2 |
| ORF7 | 3 | 1 | 1 |

TABLE 8

| Genome position | Passage 10 on MARC-145 cells nucleotide | Passage 17 on PK-9 cells nucleotide | Affected viral protein | Amino acid position | Passage 10 (on MARC-145 cells) amino acid | Passage 17 (on PK-9 cells) amino acid |
|---|---|---|---|---|---|---|
| 407 | C | T | Nsp1a | 72 | P | P |
| 612 | C | T | Nsp1a | 141 | H | Y |
| 735 | G | A | Nsp1b | 2 | D | N |
| 750 | A | G | Nsp1b | 7 | S | G |
| 756 | G | A | Nsp1b | 9 | D | N |
| 965 | T | C | Nsp1b | 78 | G | G |
| 992 | A | T | Nsp1b | 87 | E | D |
| 1009 | G | A | Nsp1b | 93 | C | Y |
| 1096 | C | A | Nsp1b | 122 | P | H |
| 1215 | C | T | Nsp1b | 162 | L | L |
| 1376 | A | G | Nsp2 | 12 | A | A |
| 1395 | T | C | Nsp2 | 19 | C | R |
| 1871 | A | G | Nsp2 | 177 | L | L |
| 2185 | T | C | Nsp2 | 282 | M | T |
| 2235 | G | A | Nsp2 | 299 | D | N |
| 2403 | G | T | Nsp2 | 355 | V | L |
| 2731 | A | G | Nsp2 | 464 | Y | C |
| 2804 | C | T | Nsp2 | 488 | D | D |
| 2918 | T | C | Nsp2 | 526 | S | S |
| 3019 | A | G | Nsp2 | 560 | Y | C |
| 3067 | G | A | Nsp2 | 576 | G | E |
| 3074 | T | C | Nsp2 | 578 | S | S |
| 3214 | G | A | Nsp2 | 625 | R | K |
| 3256 | T | C | Nsp2 | 639 | L | S |
| 3563 | C | T | Nsp2 | 741 | I | I |

TABLE 8-continued

| Genome position | Passage 10 on MARC-145 cells nucleotide | Passage 17 on PK-9 cells nucleotide | Affected viral protein | Amino acid position | Passage 10 (on MARC-145 cells) amino acid | Passage 17 (on PK-9 cells) amino acid |
|---|---|---|---|---|---|---|
| 3740 | A | G | Nsp2 | 800 | A | A |
| 4154 | T | C | Nsp2 | 938 | C | C |
| 4477 | A | C | Nsp3 | 72 | K | T |
| 4643 | A | G | Nsp3 | 127 | V | V |
| 4705 | T | C | Nsp3 | 148 | V | A |
| 4736 | C | T | Nsp3 | 158 | P | P |
| 4784 | C | T | Nsp3 | 174 | V | V |
| 5231 | C | T | Nsp3 | 323 | I | I |
| 5324 | C | T | Nsp3 | 354 | L | L |
| 5498 | A | G | Nsp3 | 412 | L | L |
| 5855 | T | C | Nsp4 | 85 | D | D |
| 5862 | G | A | Nsp4 | 88 | A | T |
| 5985 | C | A | Nsp4 | 129 | L | I |
| 6155 | T | C | Nsp4 | 185 | D | D |
| 6505 | C | T | Nsp5 | 98 | A | V |
| 6776 | A | G | Nsp7 | 2 | L | L |
| 7419 | G | A | Nsp7 | 217 | D | N |
| 7521 | T | C | Nsp7 | 251 | S | P |
| 8032 | A | G | Nsp9 | 162 | A | A |
| 8074 | C | T | Nsp9 | 176 | G | G |
| 8200 | A | G | Nsp9 | 218 | G | G |
| 8263 | T | C | Nsp9 | 239 | S | S |
| 8485 | T | C | Nsp9 | 313 | H | H |
| 8593 | T | C | Nsp9 | 349 | P | P |
| 8831 | G | A | Nsp9 | 429 | V | I |
| 8911 | T | C | Nsp9 | 455 | N | N |
| 9022 | A | G | Nsp9 | 492 | L | L |
| 9714 | T | C | Nsp10 | 38 | I | T |
| 9934 | C | T | Nsp10 | 111 | N | N |
| 10,237 | G | A | Nsp10 | 212 | L | L |
| 10,271 | C | T | Nsp10 | 224 | L | L |
| 10,333 | T | C | Nsp10 | 244 | L | L |
| 10,520 | A | G | Nsp10 | 307 | M | V |
| 10,627 | T | C | Nsp10 | 342 | V | V |
| 10,847 | A | C | Nsp10 | 416 | I | L |
| 10,867 | C | T | Nsp10 | 422 | F | F |
| 10,936 | C | T | Nsp11 | 4 | S | S |
| 11,512 | T | C | Nsp11 | 196 | S | S |
| 12,949 | A | G | ORF3 | 90 | L | L |
| 13,452 | C | T | ORF4 | 76 | P | P |
| 13,575 | G | A | ORF4 | 117 | V | V |
| 13,843 | T | G | ORF5 | 24 | C | W |
| 13,860 | G | A | ORF5 | 30 | S | N |
| 14,287 | C | T | ORF5 | 172 | N | N |
| 14,481 | A | G | ORF6 | 41 | L | L |
| 14,546 | T | C | ORF6 | 63 | V | A |
| 14,578 | A | G | ORF6 | 74 | T | A |
| 14,780 | C | T | ORF6 | 141 | T | I |
| 14,932 | T | C | ORF7 | 20 | N | N |

TABLE 9

Amino acid changes responsible for reduced interferon inhibition and attenuation of virulence.

| Genome Position (nt) | ORF and position (aa) | Nsp and position (aa) | Passage 0 amino acid | Passage 17 amino acid | Passage 52 amino acid |
|---|---|---|---|---|---|
| 735 | ORF1a: 182 | Nsp1b: 2 | AMADVYD | AMANVYD | AMANVYD |
| 756 | ORF1a: 189 | Nsp1b: 9 | ISHDAVM | IGHNAVM | IGHNAVM |
| 992 | ORF1a: 267 | Nsp1b: 87 | TVPEGNC | TVPDGNC | TVPDGNC |
| 1009 | ORF1a: 273 | Nsp1b: 93 | CWWCLFD | CWWYLFD | CWWYLFD |
| 1096 | ORF1a: 302 | Nsp1b: 122 | HGVPGKY | HGVHGKY | HGVHGKY |

TABLE 9-continued

Amino acid changes responsible for reduced interferon inhibition and attenuation of virulence.

| Genome Position (nt) | ORF and position (aa) | Nsp and position (aa) | Passage 0 amino acid | Passage 17 amino acid | Passage 52 amino acid |
|---|---|---|---|---|---|
| 2106 | ORF1a: 639 | Nsp2: 256 | AAKIDQY | AAKVDQY | AAKVDQY |
| 2185 | ORF1a: 665 | Nsp2: 282 | PSAMDTS | PSATDTS | PSATDTS |
| 2403 | ORF1a: 738 | Nsp2: 355 | LVSVLSK | LNSLLSK | LNSLLSK |
| 3019 | ORF1a: 943 | Nsp2: 560 | APMYQDE | APMCQDE | APMCQDE |
| 4477 | ORF1a: 1429 | Nsp3: 72 | CAPKGMD | CAPTGMD | CAPTGMD |
| 4705 | ORF1a: 1505 | Nsp3: 148 | PKVVKVS | PKVAKVS | PKVAKVS |
| 5985 | ORF1a: 1932 | Nsp4: 129 | AGELVGV | AGEIVGV | AGEIVGV |
| 7419 | ORF1a: 2410 | Nsp7: 217 | ADFDPEK | ADFNPEK | ADFNPEK |
| 8831 | ORF1a/1b: 2881 | Nsp9: 429 | QTPVLGR | QTPILGR | QTPILGR |
| 13,857 | ORF5: 29 | — | AVLVNAN | AVLGNAN | AVLGNAN |
| 14,578 | ORF6: 74 | — | VALTMGA | VALAMGA | VALAMGA |
| 14,780 | ORF6: 141 | — | PGSTTVN | PGSITVN | PGSITVN |

TABLE 10

Amino acid changes responsible for reduced interferon inhibition and attenuation of virulence

| Genome Position (nt) | ORF and position (aa) | Nsp and position (aa) | Passage 0 amino acid | Passage 17 amino acid | Passage 52 amino acid |
|---|---|---|---|---|---|
| 735 | ORF1a: 182 | Nsp1b: 2 | AMADVYD | AMANVYD | AMANVYD |
| 756 | ORF1a: 189 | Nsp1b: 9 | ISHDAVM | IGHNAVM | IGHNAVM |
| 1009 | ORF1a: 273 | Nsp1b: 93 | CWWCLFD | CWWYLFD | CWWYLFD |
| 1096 | ORF1a: 302 | Nsp1b: 122 | HGVPGKY | HGVHGKY | HGVHGKY |
| 2185 | ORF1a: 665 | Nsp2: 282 | PSAMDTS | PSATDTS | PSATDTS |
| 3019 | ORF1a: 943 | Nsp2: 560 | APMYQDE | APMCQDE | APMCQDE |
| 4477 | ORF1a: 1429 | Nsp3: 72 | CAPKGMD | CAPTGMD | CAPTGMD |
| 4705 | ORF1a: 1505 | Nsp3: 148 | PKVVKVS | PKVAKVS | PKVAKVS |
| 7419 | ORF1a: 2410 | Nsp7: 217 | ADFDPEK | ADFNPEK | ADFNPEK |

Example 9

Vaccine Consisting of P129-PKC12-FL Virus is Safe for Use in 1 Day Old Pigs and Efficacious for at Least 26 Weeks Existing PRRS modified live vaccines are only recommended for use in pigs two weeks of age or older. Studies were conducted to determine if the attenuated P129-PKC12-FL virus at passage 57 (2.13 log$_{10}$ TCID$_{50}$ in a 2 mL dose) is safe for use in 1-day old neonatal pigs, and sufficiently immunogenic to provide protection against a virulent heterogeneous challenge at up to 6 months (26 weeks) following vaccination. (this is essentially the same as the passage 52 virus, as described in SEQ ID No: 6).

A total of 22 of 24 PRRSV seronegative pregnant sows sourced produced healthy piglets. These pigs (piglets) were administered a single 2.0 mL dose of the Mock Vaccine or the P129-PKC12-FL virus vaccine as an intramuscular injection at approximately 1 day of age (Day 0) according to an allotment. All healthy piglets in a litter/farrowing crate received the same Mock Vaccine (11 litters, 100 piglets) or P129-PKC12-FL virus vaccine (11 litters, 91 piglets) on the same day.

Mock vaccinated sows and piglets remained PRRSV negative throughout the vaccination period. No confounding disease factors were detected. The primary variables used to demonstrate safety in piglets vaccinated at 1 day of age were clinical observations post-vaccination. Serology was used to confirm successful vaccination of all piglets.

Clinical observations were observed and recorded for all piglets on Days 1 thru 10 post vaccination. Of the 100 pigs (piglets) administered the control product (T01) and 91 piglets administered the test product (T02), 15 and 14 pigs, respectively were observed to be not normal (Table 11, referring to the tables as numbered within this specific example). Piglets observed as not normal were further noted as having abnormal general condition and/or depression.

TABLE 11

Number of Pigs Ever Observed with Clinical Signs Following a Vaccination at One Day of Age with a Modified Live PRRSV Vaccine or Control [Number of animals observed with an abnormal health condition (% animals observed with an abnormal condition)]

| Treatment Group | Not Normal | General Condition | Depression | Respiratory Distress | Cough | Sneeze | Other |
|---|---|---|---|---|---|---|---|
| Mock Vaccine | 15 (15.3) | 15 (15.3) | 5 (5.2) | 0 | 0 | 0 | 0 |
| P129-PKC12-FL Vaccine | 14 (15.4) | 14 (15.4) | 5 (5.6) | 0 | 0 | 0 | 0 |

IDEXX ELISA results confirmed all pigs were negative for PRRSV prior to vaccination (S/P ratio <0.4) and all mock vaccine controls remained serologically negative during the vaccination phase of this study. Following vaccination, all pigs in the P129-PKC12-FL Vaccine group were seropositive (S/P ratio >0.4) by Day 21 or 22 (Table 12 below).

TABLE 12

Serum Geometric Mean PRRSV Titers (IDEXX Elisa) Following a Vaccination at One Day of Age with a Modified Live PRRSV Vaccine or Control [Mean titer (Animals positive*/total animals)]

| Treatment Group | Day 0 | Day 10/11 | Day 21/22 |
|---|---|---|---|
| Mock Vaccine | 0.002 (0/100) | 0.000 (0/86) | 0.001 (0/85) |
| P129-PKC12-FL Vaccine | 0.002 (0/91) | 1.322 (76/85) | 2.412 (81/81) |

The data supports the conclusion that attenuated P129-PKC12-FL virus at passage 57 is safe when administered as a single 2 mL IM dose to piglets produced by seronegative sows at one day of age when observed though weaning at 21 or 22 days of age.

Prior to challenge, mock vaccinated and P129-PKC12-FL virus vaccinated piglets were re-housed in pens (2 piglets from the same vaccination group per pen) in rooms, such that each room contained 12 pens from each vaccination group. Challenged was with the virulent heterologous PRRS isolate NADC20 at either 7, 18, or 26 weeks post-vaccination. A challenge dose equaled 4.0 mL (1.0 mL per nostril plus a 2.0 mL intramuscular injection) of NADC20 stock solution at 2.27 $\log_{10}$ $TCID_{50}$/mL (2.87 $\log_{10}$ $TCID_{50}$/4 mL dose). NADC-20 is a very virulent genotype 2 PRRS virus, provided by Dr. Kelly Lager of the National Animal Disease Center, USDA (Ames, Iowa). The NADC-20 ORF5 amino acid sequence is 94.5% identical to P129-PKC12-FL.

The primary variable in determining prevention of disease was percent lung with lesions. Lung lesions were scored at necropsy (10 days post-challenge) such that the percentage of consolidation for each lobe (left cranial, left middle, left caudal, right cranial, right middle, right caudal, and accessory) were scored and recorded as percent of lobe observed with lesions.

At 7 weeks post-vaccination, percent lung with lesions was significantly greater in the mock vaccinated pigs compared to P129-PKC12-FL virus vaccinated piglets (P≤0.0001) (Table 13).

TABLE 13

Back Transformed Least Square Means Percent Lung with Lesions Following a PRRSV NADC20 Challenge of 7-Week-Old Piglets Previously Vaccinated at One-Day of Age with a Modified Live PRRSV Vaccine or Mock Vaccine

| Treatment Group | Number of Pigs | % Lung with Lesions | Standard Error | Lower 95% Confidence Interval | Upper 95% Confidence Interval | Range |
|---|---|---|---|---|---|---|
| Mock Vaccine | 24 | 43.9 | 3.48 | 36.3 | 51.7 | 18.5-68.5 |
| P129-PKC12-FL Vaccine | 22 | 0.7 | 0.29 | 0.2 | 1.5 | 0-8.25 |

At 18 weeks post-vaccination, percent lung with lesions was significantly greater in the mock vaccinated piglets compared to P129-PKC12-FL virus vaccinated piglets (P≤0.0001) (Table 14).

TABLE 14

Back Transformed Least Square Means Percent Lung with Lesions Following a PRRSV NADC20 Challenge of 18-Week-Old Piglets Previously Vaccinated at One-Day of Age with a Modified Live PRRSV Vaccine or Control

| Treatment Group | Number of Pigs | % Lung with Lesions | Standard Error | Lower 95% Confidence Interval | Upper 95% Confidence Interval | Range |
|---|---|---|---|---|---|---|
| Mock Vaccine | 23 | 21.1 | 3.70 | 13.6 | 29.7 | 1.9-63.0 |
| P129-PKC12-FL Vaccine | 20 | 1.0 | 0.43 | 0.3 | 2.1 | 0-5.95 |

At 26 weeks post-vaccination, percent lung with lesions was significantly greater in the mock vaccinated pigs compared to P129-PKC12-FL virus vaccinated piglets (P≤0.0001) (Table 15).

TABLE 15

Back Transformed Least Square Means Percent Lung with Lesions Following a PRRSV NADC20 Challenge of 26-Week-Old Piglets Previously Vaccinated at One-Day of Age with a Modified Live PRRSV Vaccine or Control

| Treatment Group | Number of Pigs | % Lung with Lesions | Standard Error | Lower 95% Confidence Interval | Upper 95% Confidence Interval | Range |
|---|---|---|---|---|---|---|
| Mock Vaccine | 24 | 17.7 | 2.59 | 12.4 | 23.8 | 4.5-51 |
| P129-PKC12-FL Vaccine | 24 | 1.2 | 0.72 | 0.1 | 3.3 | 0-20 |

The results indicate that attenuated vaccine virus P129-PKC12-FL is safe in 1-day old piglets, and is capable of inducing a potent immunological response with an exceptional duration of immunity. A single dose protects 1-day old piglets from a virulent heterologous PRRS challenge for at least 26 weeks.

These properties of safety in 1-day old piglets and 26 week duration of PRRS immunity is useful for multivalent combination swine vaccines, such as bivalent PRRSV/*Mycoplasma hyopneumoniae* (*M. hyo*) vaccines, bivalent PRRSV/Porcine Circovirus type 2 (PCV2) vaccines, and trivalent PRRSV/*M. hyo*/PCV2 vaccines, as well as for monovalent PRRSV vaccines.

Example 10

Vaccine Consisting of P129-PKC12-FL Virus Provides an Early Onset of Protective Immunity Existing modified live PRRS vaccines are recommended for vaccination at least 3 to 4 weeks prior to exposure to virulent PRRS strains. This time interval is believed to be necessary in order to establish protective immunity. The study described here demonstrates significant protection against a virulent heterologous PRRS virus challenge delivered only 14 days following vaccination with the P129-PKC12-FL virus vaccine and two other commercial PRRS vaccines.

During the vaccination phase, treatment groups of 18 pigs (at 3 weeks of age) were housed in four separate rooms in pens of 6 animals each. Pigs (piglets) were administered a single intramuscular injection of the Mock Vaccine (2 mL), the attenuated P129-PKC12-FL passage 57 virus vaccine (3.62 $\log_{10}$ $TCID_{50}$ in a 2 mL dose), Ingelvac PRRS MLV vaccine, or Ingelvac PRRS ATP vaccine, at approximately 3 weeks of age (Day 0) according to manufacturer's instructions.

Prior to challenge, all remaining animals were re-housed in pens of 3 animals each, with one empty pen between each occupied pen, such that multiple pens of animals from each treatment group were housed in each of four rooms. Challenged was with the virulent heterologous PRRS isolate NADC20 at approximately 5 weeks of age (Day 14). A challenge dose equaled 4.0 mL (1.0 mL per nostril plus a 2.0 mL intramuscular injection) of NADC20 stock solution at 2.07 $\log_{10}$ $TCID_{50}$/mL (2.67 $\log_{10}$ $TCID_{50}$/4 mL dose).

The primary variable in determining reduction of disease was percent lung lesions in the vaccinated groups in relation to mock vaccine group. Significant differences were found between all vaccinated groups (P129-PKC12-FL, P=0.0177; Ingelvac PRRS ATP, P=0.0255; Ingelvac PRRS MLV, P=0.0137) when compared to the mock vaccinated group. No significant differences were found when comparing vaccinated groups to each other (Table 16).

TABLE 16

Percent Lung with Lesions Following a PRRSV NADC20 Challenge of Five-Week-Old Pigs Previously Vaccinated with a Modified Live PRRSV Vaccine or Mock Vaccine.

| Treatment Group | Number of Pigs | % Lung with Lesion | Standard Error | Range |
|---|---|---|---|---|
| Mock Vaccine | 18 | 46.1 | 10.12 | 1.4-88.4 |
| P129-PKC12-FL Vaccine | 18 | 17.5 | 7.71 | 0.23-76.6 |
| Ingelvac PRRS ATP Vaccine | 18 | 18.9 | 7.96 | 0.18-88.96 |
| Ingelvac PRRS MLV Vaccine | 17 | 16.0 | 7.62 | 0.45-71.2 |

These results demonstrate that it may be a general property of modified live PRRS virus vaccines to induce partial immunity and a reduction of disease by 14 days post-vaccination. This property may result from a combination of early acquired immunity (e.g. specific antibodies and cytotoxic T cells), innate immunity (e.g. induced interferons and natural killer cells), and/or competition between the vaccine virus and the challenge virus for limited numbers of permissive host cells (e.g. alveolar macrophages) in the pig (piglet). Regardless of the mechanism(s), this property can be utilized to protect pigs from disease associated with natural or intentional PRRS infection (such as intentional exposure of incoming replacement gilts with an endemic farm strain of virulent PRRS).

Thus, as aforementioned, this property of early onset of PRRS immunity is useful for multivalent combination swine vaccines, such as bivalent PRRSV/*Mycoplasma hyopneumoniae* (*M. hyo*) vaccines, bivalent PRRSV/Porcine Circovirus type 2 (PCV2) vaccines, and trivalent PRRSV/*M. hyo*/PCV2 vaccines, as well as for monovalent PRRSV vaccines. As to the components of such vaccines, useful in the practice of the present invention (i.e. to provide early and safe vaccination as early as when the piglet is 1 day of age, optionally with onset of immunity at two weeks thereafter), reference is made to all the combination vaccine components as described in U.S. provisional application 61/620,189 of Niztel et al, entitled "PCV/*Mycoplasma hyopneumoniae*/PRRSZ Combination Vaccine", filed Apr. 4, 2012, the complete and entire disclosure of which is incorporated by reference herein, as if set forth in its entirety.

In regard of specific PRRS vaccines (or PRRS vaccine strains) that may be used in the practice of the present invention (i.e. to provide early and safe vaccination as early as when the piglet is 1 day of age, optionally with onset of immunity at two weeks thereafter), attention is directed to Table 1 of Murtaugh et al., Vaccine, vol 29, pp. 8192-8204, (2011), see Page 8196 thereof, where numerous such viruses/vaccines are identified, including, without limitation, Ingelvac PRRS MLV, Ingelvac PRRS ATP, and Suvaxyn PRRS (derived from Iowa State strain ISU-55). It should be noted that vaccines providing the above-mentioned performance characteristics are also expected to provide a duration of immunity period of about 6 months.

Deposit of Biological Materials

The following biological materials (see also U.S. Pat. No. 6,500,662) were deposited with the American Type Culture Collection (ATCC) at 10801 University Blvd., Manassas, Va., 20110-2209, USA on Nov. 19, 1998, and were assigned the following accession numbers.

Plasmid pT7P129A, accession number 203488
Plasmid pCMV-S-P129, accession number 203489

The complete text and disclosure of the following United States patents is incorporated herein by reference, as if fully set forth: U.S. Pat. Nos. 6,500,662, and 7,618,797.

The invention claimed is:

1. A vaccine for protecting a porcine animal against infection by a PRRS virus, which vaccine comprises (a) a polynucleotide molecule of SEQ ID NO: 6 or a polynucleotide molecule that has at least 85% identity to SEQ ID NO: 6, wherein the protein encoded by ORF1a thereof has an amino acid sequence that contains:

(1) one, two, three, or four of:
   an amino acid N within the amino acid sequence ANV (see SEQ ID NO: 9);
   an amino acid N within the amino acid sequence HNA (see SEQ ID NO: 12);
   an amino acid Y within the amino acid sequence WYL (see SEQ ID NO: 18); and
   an amino acid H within the amino acid sequence VHG (see SEQ ID NO: 21); and (2) one or both of
   an amino acid T within the amino acid sequence ATD (see SEQ ID NO: 27); and
   an amino acid C within the amino acid sequence MCQ (see SEQ ID NO: 33); and (3) one or both of
   an amino acid T within the amino acid sequence PTG (see SEQ ID NO: 36); and
   an amino acid A within the amino acid sequence VAK (see SEQ ID NO: 39); and (4) an amino acid N within the amino acid sequence FNP (see SEQ ID NO: 45); or (b) a North American PRRS virus encoded by said polynucleotide molecule of (a) or, (c) said polynucleotide molecule in the form of a plasmid, or (d) a viral vector comprising said polynucleotide molecule, wherein the PRRS virus is able to elicit an effective immunoprotective response against infection by PRRS virus, in an amount effective to produce immunoprotection against infection, and a carrier suitable for veterinary use, and wherein said vaccine provides early and safe vaccination as early as when the piglet is 1 day of age, and wherein said vaccine provides a duration of immunity for up to 6 months.

2. The vaccine of claim 1 wherein onset of immunity is provided beginning at two weeks after vaccination.

3. A method for vaccinating a porcine animal against infection by a PRRS virus, comprising administering the vaccine of claim 1 to said porcine, wherein said porcine is between about 12 hours after birth and 2 weeks of age and wherein the duration of protective immunity provided is up to 6 months.

4. The method of claim 3 wherein protective immunity arises no later than about 14 days after vaccination.

5. The method of claim 4, wherein protective immunity arises at Day 15 following vaccination on Day 1 of life, Day 21 following vaccination on Day 7 of life, or no later than about Day 28 following vaccination on Day 14 of life.

* * * * *

SEQUENCE LISTING

<160> NUMBER OF SEQ ID NOS: 59

<210> SEQ ID NO 1
<211> LENGTH: 15450
<212> TYPE: DNA
<213> ORGANISM: Artificial Sequence
<220> FEATURE:
<223> OTHER INFORMATION: P129-PK-FL passage 17 complete genome (15,450 nt) full length infectious clone

<400> SEQUENCE: 1

```
atgacgtata ggtgttggct ctatgccacg gcatttgtat tgtcaggagc tgtgaccatt      60
ggcacagccc aaaacttgct gcacggaaaa cgcccttctg tgacagcctt cttcagggga     120
gcttaggggt ctgtccctag caccttgctt ctggagttgc actgctttac ggtctctcca     180
cccctttaac catgtctggg atacttgatc ggtgcacgtg caccccccaat gccagggtgt     240 ttatggcgga gggccaagtc tactgcacac gatgtctcag tgcacggtct ctccttcctc     300
tgaatctcca agttcctgag cttggggtgc tgggcctatt ttataggccc gaagagccac     360
tccggtggac gttgccacgt gcattcccca ctgtcgagtg ctccctgcc ggggcctgct     420 ggctttctgc gatcttccca attgcacgaa tgaccagtgg aaacctgaac tttcaacaaa     480
gaatggtgcg ggttgcagct gagatttaca gagccggcca actcaccct gcagttttga     540 aggctctaca agtttatgaa cggggttgtc gctggtaccc cattgtcgga cctgtccctg     600
gagtggccgt ttacgccaac tccctacatg tgagtgacaa acctttcccg ggagcaactc     660
```

```
atgtgttaac caacctaccg ctcccgcaga ggcccaagcc tgaagacttt tgcccttttg    720
agtgtgctat ggctaacgtc tatgacattg gccataacgc cgtcatgtat gtggccagag    780
ggaaagtctc ctgggcccct cgtggcgggg atgaagtgaa atttgaaacc gtccccgaag    840
agttgaagtt gattgcgaac cgactccaca tctccttccc gccccaccac gcagtggaca    900
tgtctgagtt tgccttcata gcccctggga gtggtgtctc cttgcgggtc gagcaccaac    960
acggctgcct tcccgctgat actgtccctg atgggaactg ctggtggtac ttgtttgact   1020
tgctcccacc ggaagttcag aataaagaaa tcgccgtgc taaccaattt ggctatcaaa   1080
ccaagcatgg tgtccatggc aagtacctac agcggaggct gcaagttaat ggtctccgag   1140
cagtgactga tacagatgga cctattgtcg tacagtactt ctctgttagg gagagttgga   1200
tccgccactt cagattggcg gaagaaccta gcctccctgg gtttgaagac ctcctcagaa   1260
taagggtaga gcctaatacg tcgccattgg gtggcaaggg tgaaaaaatc ttccggtttg   1320
gcagtcacaa gtggtacggt gctggaaaga gagcaaggag agcacgctct ggtgcgactg   1380
ccacggtcgc tcaccgcgct ttgcccgctc gcgaagccca gcaggccaag aagctcgagg   1440
ttgccagcgc caacagggct gagcatctca agtactattc cccgcctgcc gacgggaact   1500
gtggttggca ctgcatttcc gccattacca accggatggt gaattccaaa tttgaaacca   1560
ctcttcccga gagagtgaga ccttcagatg actgggctac tgacgaggat cttgtgaata   1620
ccatccaaat cctcaggctc cccgcggcct tggacaggaa cggtgcttgt gctggcgcca   1680
agtacgtgct caagctggaa ggtgagcact ggaccgtctc tgtgaccccct gggatgaccc   1740 cttctttgct cccccttgaa tgtgttcagg gttgttgtga gcataagagc ggtcttggtt   1800
tcccagacgt ggtcgaagtt tccggatttg accctgcctg tcttgaccga cttgctgaga   1860
taatgcactt gcctagcagt gtcatcccag ctgctctggc cgagatgtcc gacgacttca   1920
atcgtctggc ttccccggcc gccactgtgt ggactgtttc gcaattcttt gcccgccaca   1980
gaggaggaga gcatcctgac caggtgtgct tagggaaaat tatcaaccttt tgtcaggtga   2040 ttgaggaatg ctgctgttcc cggaacaaag ccaaccgggc taccccggaa gaggttgcgg   2100
caaaagttga ccagtacctc cgtggtgcag caagccttgg agaatgcttg gccaagcttg   2160
agagggctcg cccgccgagc gcgacggaca cctcctttga ttggaatgtt gtgcttcctg   2220
gggttgagac ggcgaatcag acaaccaaac agctccatgt caaccagtgc cgcgctctgg   2280
ttcctgtcgt gactcaagag ccttttggaca gagactcggt ccctctgacc gccttctcgc   2340
tgtccaattg ctactaccct gcacaaggtg acgaggtccg tcaccgtgag aggctaaact   2400
ccttgctctc taagttggag ggggttgttc gtgaggaata tgggctcacg ccaactggac   2460
ctggcccgcg accgcactg ccgaacgggc tcgacgagct taaagaccag atggaggagg   2520
atctgctgaa attagtcaac gcccaggcaa cttcagaaat gatggcctgg gcagccgagc   2580
aggttgatct aaaaagcttgg gtcaaaaatt acccacggtg gacaccgcca cccccctccac   2640 caagagttca gcctcgaaaa acgaagtctg tcaagagctt gctagagaac aagcctgtcc   2700
ctgctccgcg caggaaggtc agatctgatt gtggcagccc gatttttgatg ggcgacaatg   2760 ttcctaacgg ttgggaagat tcgactgttg gtggtcccct tgatctttcg gcaccatccg   2820
agccgatgac acctctgagt gagcctgtac ttatttccag gccagtgaca tctttgagtg   2880
tgccggcccc agtcctgca ccgcgtagag ctgtgtcccg accgatgacg ccctcgagtg   2940
agccaatttt tgtgtctgca ctgcgacaca aatttcagca ggtggaaaaa gcaaatctgg   3000
```

```
cggcagcagc gccgatgtgc caggacgaac ccttagattt gtctgcatcc tcacagactg   3060
aatatgaggc ttcccccta acaccaccgc agaacgtggg cattctggag gtaaggggc     3120 aagaagctga ggaagttctg agtgaaatct cggatattct gaatgatacc aaccctgcac   3180
ctgtgtcatc aagcagctcc ctgtcaagtg ttaagatcac acgcccaaaa tactcagctc   3240
aagccattat cgactcgggc gggccctgca gtgggcacct ccaaagggaa aagaagcat    3300 gcctccgcat catgcgtgag gcttgtgatg cggccaagct tagtgaccct gccacgcagg   3360
aatggctttc tcgcatgtgg gataggtgg acatgctgac ttggcgcaac acgtctgctt    3420
accaggcgtt tcgcacctta gatggcaggt ttgggtttct cccaaagatg atactcgaga   3480
cgccgccgcc ctaccgtgt gggtttgtga tgttgcctca cccctgca ccttccgtga      3540 gtgcagagag cgaccttacc attggttcag tcgccactga agatattcca cgcatcctcg   3600
ggaaaataga aataccggt gagatgatca accagggacc cttggcatcc tctgaggaag    3660
aaccggtata caaccaacct gccaaagact cccggatatc gtcgcggggg tctgacgaga   3720
gcacagcagc tccgtccgcg gtacaggtg gcgccggctt atttactgat ttgccaccttt   3780 cagacggcgt agatgcggac ggtgggggc cgttgcagac ggtaagaaag aaagctgaaa   3840
ggctcttcga ccaattgagc cgtcaggttt taacctcgt ctcccatctc cctgttttct    3900
tctcacacct cttcaaatct gacagtggtt attctccggg tgattggggt tttgcagctt    3960
ttactctatt ttgcctcttt ttgtgttaca gctacccatt cttcggtttc gttccctct    4020 tgggtgtatt ttctgggtct tctcggcgtg tgcgcatggg ggtttttgc tgctggctgg    4080 cttttgctgt tggcctgttc aagcctgtgt ccgacccagt cggcactgct gtgagtttg    4140 actcgccaga gtgcaggaac gtccttcatt cttttgagct tctcaaacct tgggaccctg    4200
ttcgcagcct tgttgtgggc cccgtcggtc tcggtcttgc cattcttggc aggttactgg    4260
gcggggcacg ctacatctgg catttttttgc ttaggcttgg cattgttgca gattgtatct    4320
tggctggagc ttatgtgctt tctcaaggta ggtgtaaaaa gtgctgggga tcttgtataa    4380
gaactgctcc taatgaaatc gccttcaacg tgttcccttt tacacgtgcg accaggtcgt    4440
cactcatcga cctgtgcgat cggttttgtg cgccaacagg catggacccc atttcctcg    4500 ccactgggtg gcgtgggtgc tggaccggcc gaagtcccat tgagcaaccc tctgaaaaac    4560
ccatcgcgtt cgcccagttg gatgaaaaga ggattacggc tagaactgtg gtcgctcagc   4620
cttatgatcc taatcaagcc gtgaagtgct tgcgggtgtt acaggcgggt ggggcgatgg   4680
tggccgaggc agtcccaaaa gtggccaaag tttctgctat tccattccga gccccttttt   4740
ttcccaccgg agtgaaagtt gatcccgagt gcaggatcgt ggttgacccc gatactttta    4800
ctacagccct ccggtctggt tactctacca caaacctcgt ccttggtgtg gggactttg    4860 cccagctgaa tggactaaag atcaggcaaa tttccaagcc ttcgggagga gcccacacc   4920 tcattgctgc cctgcatgtt gcctgctcga tggcgttgca catgcttgct ggggtttatg    4980
taacttcagt ggggtcttgc ggtgccggca ccaacgatcc atggtgcact aatccgtttg    5040
ccgttcctgg ctacggacca ggctctctct gcacgtccag attgtgcatc tcccaacatg   5100
gccttaccct gccttgaca gcacttgtgg cgggattcgg tcttcaggaa atcgccttgg   5160
tcgttttgat tttcgtttcc atcggaggca tggctcatag gttgagttgt aaggctgata   5220
tgctgtgcat tttacttgca atcgccagct atgtttgggt accccttacc tggttgcttt   5280
gtgtgtttcc ttgttggttg cgctggttct ctttgcaccc ccttaccatc ctatggttgg    5340
tgtttttctt gatttctgta aatatgcctt cgggaatctt ggccgtggtg ttattggttt    5400
```

```
ctctttggct tttgggacgt tatactaaca ttgctggtct tgtcacccc  tatgatattc   5460
atcattacac cagtggcccc cgcggtgttg ccgccttggc taccgcacca gatggaacct   5520
acttggctgc cgtccgccgc gctgcgttga ctggtcgcac catgctgttc accccgtctc   5580
agcttgggtc ccttcttgag ggcgctttca gaactcgaaa gccctcactg aacaccgtca   5640
atgtggttgg gtcctccatg ggctctggtg gagtgttcac catcgacggg aaaattaggt   5700
gcgtgactgc cgcacatgtc cttacgggta attcggctag ggtttccgga gtcggcttca   5760
atcaaatgct tgactttgat gtgaaagggg acttcgccat agctgattgc ccgaattggc   5820
aaggagctgc tcccaagacc caattctgcg aggacggatg gactggccgt gcctattggc   5880
tgacatcctc tggcgtcgaa cccggtgtta ttgggaatgg attcgccttc tgcttcaccg   5940
cgtgcggcga ttccgggtcc ccagtgatca ccgaagctgg tgagattgtc ggcgttcaca   6000
caggatcaaa taaacaagga ggtggcatcg tcacgcgccc ttcaggccag ttttgtaacg   6060
tggcacccat caagctgagc gaattaagtg aattctttgc tggacccaag gtcccgctcg   6120
gtgatgtgaa ggttggcagc cacataatta agacacgtg cgaagtacct tcagatcttt    6180
gcgccttgct tgctgccaaa cctgaactgg agggaggcct ctccaccgtc caacttctgt   6240
gtgtgttttt cctactgtgg agaatgatgg gacatgcctg gacgcccttg gttgctgtgg   6300
ggttttcat tctgaatgag gttctcccag ctgtcctggt tcggagtgtt ttctccttg     6360
ggatgtttgt gctatcttgg ctcacaccat ggtctgcgca agttctgatg atcaggcttc   6420
taacagcagc tcttaacagg aacagatggt cacttgcctt ttacagcctt ggtgcggtga   6480
ccggttttgt cgcagatctt gcggtaactc aagggcaccc gttgcaggca gtaatgaatt   6540
tgagcaccta tgccttcctg cctcggatga tggttgtgac ctcaccagtc ccagtgattg   6600
cgtgtggtgt tgtgcaccta cttgccatca ttttgtactt gttcaagtac cgcggcctgc   6660
acaatgttct tgttggtgat ggagcgtttt ctgcagcttt cttcttgcga tactttgccg   6720
agggaaagtt gagggaaggg gtgtcgcaat cctgcggaat gaatcatgag tcattgactg   6780
gtgccctcgc tatgagactc aatgacgagg acttggactt ccttacgaaa tggactgatt   6840
ttaagtgctt tgtttctgcg tccaacatga ggaatgcagc aggccaattc atcgaggctg   6900
cctatgcaaa agcacttaga attgaacttg cccagttggt gcaggttgat aaggttcgag   6960
gtactttggc caagcttgag gcttttgctg ataccgtggc accccaactc tcgcccggtg   7020
acattgttgt tgctcttggc catacgcctg ttggcagcat cttcgaccta aaggttggtg   7080
gtaccaagca tactctccaa gtcattgaga ccagagtcct tgccgggtcc aaaatgaccg   7140
tggcgcgcgt cgttgaccca accccacgc cccacccgc accgtgccc atcccctcc       7200
caccgaaagt tctagagaat ggtcccaacg cctggggga tggggaccgt ttgaataaga   7260
agaagaggcg taggatggaa accgtcggca tctttgtcat gggtgggaag aagtaccaga   7320
aattttggga caagaattcc ggtgatgtgt tttacgagga ggtccatgac aacacagatg   7380
cgtgggagtg cctcagagtt ggtgaccctg ccgactttaa ccctgagaag ggaactctgt   7440
gtgggcatac tactattgaa gataaggatt acaaagtcta cgcctcccca tctggcaaga   7500
agttcctggt ccccgtcaac ccagagagcg gaagagccca tgggaagct gcaaagcttt    7560
ccgtggagca ggcccttggc atgatgaatg tcgacggtga actgacggcc aaagaagtgg   7620
agaaactgaa aagaataatt gacaaacttc agggcctgac taaggagcag tgttttaaact  7680
gctagccgcc agcggcttga cccgctgtgg tcgcggcggc ttggttgtta ctgagacagc   7740
```

```
ggtaaaaata gtcaaatttc acaaccggac tttcacccta gggcctgtga atttaaaagt      7800
ggccagtgag gttgagctga aagacgcggt cgagcacaac caacacccgg ttgcaagacc      7860
ggttgacggt ggtgttgtgc tcctgcgttc cgcagttcct tcgcttatag atgtcctgat      7920
ctccggtgct gacgcatctc ctaagttact cgctcgtcac gggccgggga acactgggat      7980
cgatggcacg ctttgggact tgaggccga ggccaccaaa gaggaaattg cgctcagtgc      8040
gcaaataata caggcttgtg acattaggcg cggtgacgca cctgaaattg gtctccctta      8100
caagctgtac cctgttaggg gcaaccctga gcgggtaaaa ggagttttac agaatacaag      8160
gtttggagac ataccttaca aaaccccccag tgacactggg agcccagtgc acgcggctgc      8220
ctgcctcacg cccaatgcca ctccggtgac tgatgggcgc tccgtcttgg ctactaccat      8280
gccctccggt tttgaattgt atgtaccgac cattccagcg tctgtccttg attatcttga      8340
ctctaggcct gactgcccca aacagttgac agagcacggc tgtgaggatg ccgcattgag      8400
agacctctcc aagtatgact tgtccaccca aggctttgtt ttacctgggg ttcttcgcct      8460
tgtgcgtaag tacctgtttg cccacgtggg taagtgcccg cccgttcatc ggccttccac      8520
ttaccctgcc aagaattcta tggctggaat aaatgggaac aggtttccaa ccaaggacat      8580
tcagagcgtc cccgaaatcg acgttctgtg cgcacaggcc gtgcgagaaa actggcaaac      8640
tgttacccct tgtaccctca agaaacagta ttgtgggaag aagaagacta ggacaatact      8700
cggcaccaat aatttcattg cgttggccca ccgggcagcg ttgagtggtg tcacccaggg      8760
cttcatgaaa aaggcgttta actcgcccat cgccctcggg aaaaacaaat ttaaggagct      8820
acagactccg atcttaggca ggtgccttga agctgatctt gcatcctgtg atcgatccac      8880
acctgcaatt gtccgctggt ttgccgccaa ccttctttat gaacttgcct gtgctgaaga      8940
gcacctaccg tcgtacgtgc tgaactgctg ccatgaccta ttggtcacgc agtccggcgc      9000
agtgactaag aggggtggcc tgtcgtctgg cgacccgatc acttctgtgt ctaacaccat      9060
ttacagcttg gtgatatatg cacagcacat ggtgcttagt tactttaaaa gtggtcaccc      9120
tcatggcctt ctgttcctac aagaccagct gaagttcgag gacatgctca agtccaacc      9180 cctgatcgtc tattcggacg acctcgtgct gtatgccgaa tctccccacca tgccgaacta      9240 ccactggtgg gtcgaacatc tgaatttgat gctgggtttt cagacggacc caaagaagac      9300
agccataacg gactcgccat catttctagg ctgtaggata taaatggac gccagctagt      9360 ccccaaccgt gacaggatcc tcgcggccct cgcttaccat atgaaggcaa gcaatgtttc      9420
tgaatactac gccgcggcgg ctgcaatact catggacagc tgtgcttgtt tagagtatga      9480
tcctgaatgg tttgaagagc ttgtggttgg gatagcgcag tgcgcccgca aggacggcta      9540
cagctttccc ggcccgccgt tcttcttgtc catgtgggaa aaactcagat ccaatcatga      9600
ggggaagaag tccagaatgt gcgggtattg cggggccccg gctccgtacg ccactgcctg      9660
tggcctcgac gtctgtattt accacaccca cttccaccag cattgtccag tcacaatctg      9720
gtgtggccac ccggctggtt ctggttcttg tagtgagtgc aaacccccc tagggaaagg      9780 cacaagccct ctagatgagg tgttagaaca agtcccgtat aagcctccac ggactgtaat      9840
catgcatgtg gagcagggtc tcacccctct tgacccaggc agataccaga ctcgccgcgg      9900
attagtctcc gttaggcgtg gcatcagagg aaatgaagtt gacctaccag acggtgatta      9960
tgctagcacc gccctactcc ccacttgtaa agagatcaac atggtcgctg tcgcctctaa     10020
tgtgttgcgc agcaggttca tcatcggtcc gcccggtgct gggaaaacat actggctcct     10080
tcagcaggtc caggatggtg atgtcattta cacaccgact caccagacca tgctcgacat     10140
```

```
gattagggct tggggacgt gccggttcaa cgtcccagca ggtacaacgc tgcaattccc   10200 tgcccctcc cgtaccggcc cgtgggttcg catcctagcc ggcggttggt gtcctggtaa   10260
gaattccttc ttggatgaag cagcgtattg taatcacctt gatgtcttga ggctccttag   10320
caaaaccacc ctcacctgtc tgggagactt caaacaactc cacccagtgg gttttgattc   10380
tcattgctat gttttgaca tcatgcctca gacccagttg aagaccatct ggagattcgg   10440
acagaacatc tgtgatgcca tccaaccaga ttacagggac aaacttgtgt ccatggtcaa   10500
cacaacccgt gtaacctacg tggaaaaacc tgtcaagtat gggcaagtcc tcaccccta   10560 ccacagggac cgagaggacg cgccatcac aattgactcc agtcaaggcg ccacatttga   10620
tgtggtcaca ctgcatttgc ccactaaaga ttcactcaac aggcaaagag cccttgttgc   10680
tatcaccagg gcaagacatg ctatctttgt gtatgaccca cacaggcaat tgcagagcat   10740
gtttgatctt cctgcgaagg gcacacccgt caacctcgca gtgcaccgtg atgagcagct   10800
gatcgtactg gatagaaata ataaagaatg cacagttgct caggctctag caacggaga   10860 taaatttagg gccaccgaca agcgcgttgt agattctctc cgcgccattt gtgctgatct   10920
ggaagggtcg agctctccgc tccccaaggt cgcacacaac ttgggatttt atttctcacc   10980
tgatttgaca cagtttgcta actcccggt agaccttgca ccccactggc ccgtggtgac   11040
aacccagaac aatgaaaagt ggccggatcg gctggttgcc agccttcgcc ctgtccataa   11100
gtatagccgt gcgtgcattg tgccggcta tatggtgggc ccctcggtgt ttctaggcac   11160
ccctggggtc gtgtcatact acctcacaaa atttgtcaag ggcgaggctc aagtgcttcc   11220
ggagacagtc ttcagcaccg gccgaattga ggtggattgc cgggagtatc ttgatgacag   11280
ggagcgagaa gttgctgagt ccctcccaca tgccttcatt ggcgacgtca aaggcaccac   11340
cgttggggga tgtcatcatg tcacctccaa ataccttccg cgcttccttc ccaaggaatc   11400
agtcgcggta gtcggggttt cgagcccgg gaaagccgca aaagcagtgt gcacattgac   11460
ggatgtgtac ctcccagacc ttgaggccta cctccaccca gagactcagt ccaagtgctg   11520
gaaagttatg ttggacttca aggaagttcg actgatggtc tggaaagaca agacggccta   11580
tttccaactt gaaggccgct atttcacctg gtatcagctt gcaagctacg cctcgtacat   11640
ccgtgttcct gtcaactcca cggtgtatct ggaccctgc atgggccctg ccctttgcaa   11700
cagaagagtt gtcgggtcca cccattgggg agctgacctc gcagtcaccc cttatgatta   11760
cggtgctaaa atcatcttgt ctagcgctta ccatggtgaa atgcctcctg gatacaagat   11820
tctggcgtgc gcggagttct cgctcgacga cccagtcaag tacaaacaca cctgggtt   11880 tgaatcggat acagcgtatc tgtatgagtt caccggaaac ggtgaggact gggaggatta   11940
caatgatgcg tttcgtgcgc gccagaaagg gaaaatttat aaggccactg ctaccagcat   12000
gaagttttat tttccccccgg gccccgtcat tgaaccaact ttaggcctga attgaaatga   12060 aatgggtct atacaaagcc tcttcgacaa aattggccag ctttttgtgg atgctttcac   12120 ggaattttg gtgtccattg ttgatatcat catattttg gccattttgt ttggcttcac   12180
catcgccggt tggctggtgg tcttttgcat cagattggtt tgctccgcgg tattccgtgc   12240
gcgccctgcc attcaccctg agcaattaca gaagatccta tgaggccttt ctttctcagt   12300
gccgggtgga cattcccacc tgggggtaa acacccttt ggggatgttt tggcaccata   12360
aggtgtcaac cctgattgat gaatggtgt cgcgtcgaat gtaccgcatc atggaaaaag   12420
cagggcaagc tgcctggaaa caggtggtga gcgaggctac gctgtctcgc attagtagtt   12480
```

```
tggatgtggt ggctcatttt caacatcttg ccgccattga agccgagacc tgtaaatatt   12540
tggcttctcg actgcccatg ctacacaacc tgcgcatgac agggtcaaat gtaaccatag   12600
tgtataatag cactttaaat caggtgtttg ctatttttcc aaccccctggt tcccggccaa   12660 agcttcatga ttttcagcaa tggctaatag ctgtacattc ctccatattt tcctctgttg   12720
cagcttcttg tactcttttt gttgtgctgt ggttgcgggt tccaatgcta cgtactgttt   12780
ttggtttccg ctggttaggg gcaatttttc tttcgaactc atggtgaatt acacggtgtg   12840
tccaccttgc ctcacccgac aagcagccgc tgaggtcctt gaacccggta ggtctctttg   12900
gtgcaggata gggcatgacc gatgtgggga ggacgatcac gacgaactgg ggttcatggt   12960
tccgcctggc ctctccagcg aaagccactt gaccagtgtt tacgcctggt tggcgttcct   13020
gtccttcagc tacacggccc agttccatcc cgagatattt gggatagggga acgtgagtga   13080 agtttatgtt gacatcaagc accaattcat ctgcgccgtt catgacgggc agaacaccac   13140
cttgcctcgc catgacaata tttcagccgt atttcagacc tactatcaac atcaggtcga   13200
cggcggcaat tggtttcacc tagaatggct gcgtcccttc ttttcctctt ggttggtttt   13260
aaatgtttcg tggtttctca ggcgttcgcc tgcaagccat gtttcagttc gagtctttca   13320
gacatcaaaa ccaacactac cgcagcatca ggctttgttg tcctccagga catcagctgc   13380
cttaggcatg cgactcgtc ctttccgacg attcgcaaaa gctctcaatg ccgcacggcg   13440 ataggggacac ctgtgtatat caccatcaca gccaatgtga cagatgagaa ttacttacat   13500
tcttctgatc tcctcatgct ttcttcttgc cttttctatg cttctgagat gagtgaaaag   13560
ggattcaagg tggtatttgg caatgtgtca ggcatcgtgg ctgtgtgtgt caactttacc   13620
agctacgtcc aacatgtcaa agagtttacc caacgctcct tggtggtcga tcatgtgcgg   13680
ctgcttcatt tcatgacacc tgagaccatg aggtgggcaa ccgttttagc ctgtcttttt   13740
gccatcctac tggcaatttg aatgttcaag tatgttgggg aaatgcttga ccgcgggctg   13800
ttgctcgcga ttgctttctt tgtggtgtat cgtgccgttc tggtttgctg tgctcggcaa   13860
cgccaacagc agcagcagct ctcatttca gttgatttat aacttgacgc tatgtgagct   13920
gaatggcaca gattggctgg cagaaaaatt tgattgggca gtggagactt ttgtcatctt   13980
tcccgtgttg actcacattg tttcctatgg tgcactcacc accagccatt tccttgacac   14040
agttggtctg gttactgtgt ccaccgccgg gttttatcac gggcggtatg tcttgagtag   14100
catctacgcg gtctgtgctc tggctgcgtt gatttgcttc gttattaggc ttgcgaagaa   14160
ctgcatgtcc tggcgctact cttgtaccag atataccaac ttccttctgg acactaaggg   14220
cagactctat cgttggcggt cgcccgttat catagaaaaa gggggtaagg ttgaggtcga   14280
aggtcatctg atcgacctca aaagagttgt gcttgatggt tccgtggcaa cccctttaac   14340
cagagtttca gcggaacaat ggggtcgtct ctagacgact tttgccatga tagcacggct   14400
ccacaaaagg tgcttttggc gttttccatt acctacgcgc cagtaatgat atatgctcta   14460
aaggtaagtc gcggccgact gctagggctt ctgcacccttt tgatctttct gaattgtgct   14520
tttaccttcg ggtacatgac attcgcgcac tttcagagca caaatagggt cgcgctcgct   14580
atgggagcag tagttgcact tctttgggggg gtgtactcag ccatagaaac ctggaaattc   14640
atcacctcca gatgccgttt gtgcttgcta ggccgcaagt acattctggc ccctgcccac   14700
cacgtcgaaa gtgccgcggg ctttcatccg attgcggcaa atgataacca cgcatttgtc   14760
gtccggcgtc ccggctccat tacgcgttaac ggcacattgg tgcccgggtt gaaaagcctc   14820
gtgttgggtg gcagaaaagc tgttaaacag ggagtggtaa accttgtcaa atatgccaaa   14880
```

```
taacaacggc aagcagcaaa agaaaaagaa ggggaatggc cagccagtca accagctgtg  14940
ccagatgctg ggtaaaatca tcgcccagca aaaccagtcc agaggcaagg gaccgggcaa  15000
gaaaagtaag aagaaaaacc cggagaagcc ccattttcct ctagcgaccg aagatgacgt  15060
caggcatcac ttcacccctg gtgagcggca attgtgtctg tcgtcgatcc agactgcctt  15120
taaccagggc gctggaactt gtaccctgtc agattcaggg aggataagtt acactgtgga  15180
gtttagtttg ccgacgcatc atactgtgcg cctgatccgc gtcacagcat caccctcagc  15240
atgatgggct ggcattcttt aggcacctca gtgtcagaat tggaagaatg tgtggtggat  15300
ggcactgatt gacattgtgc ctctaagtca cctattcaat tagggcgacc gtgtgggggt  15360
aaaatttaat tggcgagaac catgcggccg caattaaaaa aaaaaaaaaa aaaaaaaaaa  15420
aaaaaaaaaa aaaaaaaaaa aaaaaaaaaa                                    15450
```

<210> SEQ ID NO 2
<211> LENGTH: 15444
<212> TYPE: DNA
<213> ORGANISM: Artificial Sequence
<220> FEATURE:
<223> OTHER INFORMATION: P129-PK-d43/44 passage 17 complete genome
(15,444 nt) 2 aa deleted infectious clone

<400> SEQUENCE: 2

```
atgacgtata ggtgttggct ctatgccacg gcatttgtat tgtcaggagc tgtgaccatt     60
ggcacagccc aaaacttgct gcacggaaaa cgcccttctg tgacagcctt cttcagggga    120
gcttaggggt ctgtccctag caccttgctt ctggagttgc actgctttac ggtctctcca    180 ccccttttaac catgtctggg atacttgatc ggtgcacgtg cacccccaat gccagggtgt    240
ttatggcgga gggccaagtc tactgcacac gatgtctcag tgcacggtct ctccttcctc    300
tgaatctcca agttcctgag cttggggtgc tgggcctatt ttataggccc gaagagccac    360
tccggtggac gttgccacgt gcattcccca ctgtcgagtg ctcccctgcc ggggcctgct    420
ggctttctgc gatctttcca attgcacgaa tgaccagtgg aaacctgaac tttcaacaaa    480
gaatggtgcg ggttgcagct gagatttaca gagccggcca actcacccct gcagttttga    540
aggctctaca agtttatgaa cggggttgtc gctggtaccc cattgtcgga cctgtccctg    600
gagtggccgt ttacgccaac tccctacatg tgagtgacaa acctttcccg ggagcaactc    660
atgtgttaac caacctaccg ctcccgcaga ggcccaagcc tgaagacttt tgcccttttg    720
agtgtgctat ggctaacgtc tatgacattg gccataacgc cgtcatgtat gtggccagag    780
ggaaagtctc ctgggcccct cgtggcgggg atgaagtgaa atttgaaacc gtccccgaag    840
agttgaagtt gattgcgaac cgactccaca tctccttccc gccccaccac gcagtggaca    900
tgtctgagtt tgccttcata gcccctggga gtggtgtctc cttgcgggtc gagcaccaac    960
acggctgcct tcccgctgat actgtccctg atgggaactg ctggtggtac ttgtttgact   1020
tgctcccacc ggaagttcag aataaagaaa ttcgccgtgc taaccaattt ggctatcaaa   1080
ccaagcatgg tgtccatggc aagtacctac agcggaggct gcaagttaat ggtctccgag   1140
cagtgactga tacagatgga cctattgtcg tacagtactt ctctgttagg gagagttgga   1200
tccgccactt cagattggcg gaagaaccta gcctccctgg gtttgaagac ctcctcagaa   1260
taagggtaga gcctaatacg tcgccattgg gtggcaaggg tgaaaaaatc ttccggtttg   1320
gcagtcacaa gtggtacggt gctggaaaga gagcaaggag agcacgctct ggtgcgactg   1380
ccacggtcgc tcaccgcgct ttgcccgctc gcgaagccca gcaggccaag aagctcgagg   1440
```

```
ttgccagcgc caacagggct gagcatctca agtactattc cccgcctgcc gacgggaact   1500
gtggttggca ctgcatttcc gccattacca accggatggt gaattccaaa tttgaaacca   1560
ctcttcccga gagagtgaga ccttcagatg actgggctac tgacgaggat cttgtgaata   1620
ccatccaaat cctcaggctc cccgcggcct tggacaggaa cggtgcttgt gctggcgcca   1680
agtacgtgct caagctggaa ggtgagcact ggaccgtctc tgtgacccct gggatgaccc   1740
cttctttgct cccccttgaa tgtgttcagg gttgttgtga gcataagagc ggtcttggtt   1800
tcccagacgt ggtcgaagtt ccggatttg accctgcctg tcttgaccga cttgctgaga   1860
taatgcactt gcctagcagt gtcatcccag ctgtctggc cgagatgtcc gacgacttca   1920
atcgtctggc ttccccggcc gccactgtgt ggactgtttc gcaattcttt gcccgccaca   1980
gaggaggaga gcatcctgac caggtgtgct tagggaaaat tatcaacctt tgtcaggtga   2040
ttgaggaatg ctgctgttcc cggaacaaag ccaaccgggc taccccggaa gaggttgcgg   2100
caaaagttga ccagtacctc cgtggtgcag caagccttgg agaatgcttg ccaagcttg   2160 agagggctcg cccgccgagc gcgacggaca cctcctttga ttggaatgtt gtgcttcctg   2220
gggttgagac ggcgaatcag acaaccaaac agctccatgt caaccagtgc cgcgctctgg   2280
ttcctgtcgt gactcaagag cctttggaca gagactcggt ccctctgacc gccttctcgc   2340
tgtccaattg ctactaccct gcacaaggtg acgaggtccg tcaccgtgag aggctaaact   2400
ccttgctctc taagttggag ggggttgttc gtgaggaata tgggctcacg ccaactggac   2460
ctggcccgcg accgcactg ccgaacgggc tcgacgagct taaagaccag atggaggagg   2520
atctgctgaa attagtcaac gcccaggcaa cttcagaaat gatggcctgg gcagccgagc   2580
aggttgatct aaaagcttgg gtcaaaaatt acccacggtg gacaccgcca ccccctccac   2640
caagagttca gcctcgaaaa acgaagtctg tcaagagctt gctagagaac aagcctgtcc   2700
ctgctccgcg caggaaggtc agatctgatt gtggcagccc gattttgatg ggcgacaatg   2760
ttcctaacgg ttgggaagat tcgactgttg gtggtccct tgatctttcg gcaccatccg   2820
agccgatgac acctctgagt gagcctgtac ttatttccag gccagtgaca tctttgagtg   2880
tgccggcccc agttcctgca ccgcgtagag ctgtgtcccg accgatgacg ccctcgagtg   2940
agccaatttt tgtgtctgca ctgcgacaca aatttcagca ggtggaaaaa gcaaatctgg   3000
cggcagcagc gccgatgtgc caggacgaac ccttagattt gtctgcatcc tcacagactg   3060
aatatgaggc ttccccccta acaccaccgc agaacgtggg cattctggag gtaaggggc   3120 aagaagctga ggaagttctg agtgaaatct cggatattct gaatgatacc aaccctgcac   3180
ctgtgtcatc aagcagctcc ctgtcaagtg ttaagatcac acgcccaaaa tactcagctc   3240
aagccattat cgactcgggc gggccctgca gtgggcaccc ccaaagggaa aaagaagcat   3300
gcctccgcat catgcgtgag gcttgtgatg cggccaagct tagtgaccct gccacgcagg   3360
aatggctttc tcgcatgtgg gatagggtgg acatgtgac ttggcgcaac acgtctgctt   3420
accaggcgtt tcgcacctta gatggcaggt ttgggtttct cccaaagatg atactcgaga   3480
cgccgccgcc ctaccgtgt gggttttgtga tgttgcctca cacccctgca ccttccgtga   3540
gtgcagagag cgaccttacc attggttcag tcgccactga agatattcca cgcatcctcg   3600 ggaaaatga aaataccggt gagatgatca accagggacc cttggcatcc tctgaggaag   3660
aaccggtata caaccaacct gccaaagact cccggatatc gtcgcggggg tctgacgaga   3720
gcacagcagc tccgtccgcg ggtacaggtg gcgccggctt atttactgat ttgccacctt   3780
```

```
cagacggcgt agatgcggac ggtgggtggc cgttgcagac ggtaagaaag aaagctgaaa    3840
ggctcttcga ccaattgagc cgtcaggttt ttaacctcgt ctcccatctc cctgttttct    3900
tctcacacct cttcaaatct gacagtggtt attctccggg tgattggggt tttgcagctt    3960
ttactctatt ttgcctcttt ttgtgttaca gctacccatt cttcggtttc gttccctct     4020
tgggtgtatt ttctgggtct tctcggcgtg tgcgcatggg ggtttttggc tgctggctgg    4080
cttttgctgt tggcctgttc aagcctgtgt ccgacccagt cggcactgct tgtgagtttg    4140
actcgccaga gtgcaggaac gtccttcatt cttttgagct tctcaaacct tgggaccctg    4200
ttcgcagcct tgttgtgggc cccgtcggtc tcggtcttgc cattcttggc aggttactgg    4260
gcggggcacg ctacatctgg cattttttgc ttaggcttgg cattgttgca gattgtatct    4320
tggctggagc ttatgtgctt tctcaaggta ggtgtaaaaa gtgctgggga tcttgtataa    4380
gaactgctcc taatgaaatc gccttcaacg tgttcccttt tacacgtgcg accaggtcgt    4440
cactcatcga cctgtgcgat cggttttgtg cgccaacagg catggacccc attttcctcg    4500
ccactgggtg gcgtgggtgc tggaccggcc gaagtcccat tgagcaaccc tctgaaaaac    4560
ccatcgcgtt cgcccagttg gatgaaaaga ggattacggc tagaactgtg gtcgctcagc    4620
cttatgatcc taatcaagcc gtgaagtgct tgcgggtgtt acaggcgggt ggggcgatgg    4680
tggccgaggc agtcccaaaa gtggccaaag tttctgctat tccattccga gcccctttt     4740
ttcccaccgg agtgaaagtt gatcccgagt gcaggatcgt ggttgacccc gatactttta    4800
ctacagccct ccggtctggt tactctacca caaacctcgt ccttggtgtg gggactttg     4860
cccagctgaa tggactaaag atcaggcaaa tttccaagcc ttcgggagga ggcccacacc    4920
tcattgctgc cctgcatgtt gcctgctcga tggcgttgca catgcttgct ggggtttatg    4980
taacttcagt ggggtcttgc ggtgccggca ccaacgatcc atggtgcact aatccgtttg    5040
ccgttcctgg ctacggacca ggctctctct gcacgtccag attgtgcatc tcccaacatg    5100
gccttaccct gcccttgaca gcacttgtgg cgggattcgg tcttcaggaa atcgccttgg    5160
tcgttttgat tttcgtttcc atcggaggca tggctcatag gttgagttgt aaggctgata    5220
tgctgtgcat tttacttgca atcgccagct atgtttgggt accccttacc tggttgcttt    5280
gtgtgtttcc ttgttggttg cgctggttct cttttgcaccc ccttaccatc ctatggttgg    5340
tgtttttctt gatttctgta aatatgcctt cgggaatctt ggccgtggtg ttattggttt    5400
ctctttggct tttgggacgt tatactaaca ttgctggtct tgtcaccccc tatgatattc    5460
atcattacac cagtggcccc cgcggtgttg ccgccttggc taccgcacca gatggaacct    5520
acttggctgc cgtccgccgc gctgcgttga ctggtcgcac catgctgttc accccgtctc    5580
agcttgggtc ccttcttgag ggcgctttca gaactcgaaa gccctcactg aacaccgtca    5640
atgtggttgg gtcctccatg ggctctggtg gagtgttcac catcgacggg aaaattaggt    5700
gcgtgactgc cgcacatgtc cttacgggta attcggctag ggtttccgga gtcggcttca    5760
atcaaatgct tgactttgat gtgaaagggg acttcgccat agctgattgc ccgaattggc    5820
aaggagctgc tcccaagacc caattctgcg aggacggatg gactggccgt gcctattggc    5880
tgacatcctc tggcgtcgaa cccggtgtta ttgggaatgg attcgccttc tgcttcaccg    5940
cgtgcggcga ttccgggtcc ccagtgatca ccgaagctgg tgagattgtc ggcgttcaca    6000
caggatcaaa taacaagga ggtggcatcg tcacgcgccc ttcaggccag ttttgtaacg    6060
tggcacccat caagctgagc gaattaagtg aattctttgc tggacccaag gtcccgctcg    6120
gtgatgtgaa ggttggcagc cacataatta agacacgtg cgaagtacct tcagatcttt    6180
```

```
gcgccttgct tgctgccaaa cctgaactgg agggaggcct ctccaccgtc caacttctgt    6240
gtgtgttttt cctactgtgg agaatgatgg gacatgcctg gacgcccttg gttgctgtgg    6300 ggttttt cat tctgaatgag gttctcccag ctgtcctggt tcggagtgtt ttctcctttg    6360 ggatgttgt gctatcttgg ctcacaccat ggtctgcgca agttctgatg atcaggcttc      6420
taacagcagc tcttaacagg aacagatggt cacttgcctt ttacagcctt ggtgcggtga    6480
ccggttttgt cgcagatctt gcggtaactc aagggcaccc gttgcaggca gtaatgaatt    6540
tgagcaccta tgccttcctg cctcggatga tggttgtgac ctcaccagtc ccagtgattg    6600
cgtgtggtgt tgtgcaccta cttgccatca ttttgtactt gttcaagtac cgcggcctgc    6660
acaatgttct tgttggtgat ggagcgtttt ctgcagcttt cttcttgcga tactttgccg    6720
agggaaagtt gagggaaggg gtgtcgcaat cctgcggaat gaatcatgag tcattgactg    6780
gtgccctcgc tatgagactc aatgacgagg acttggactt ccttacgaaa tggactgatt    6840
ttaagtgctt tgtttctgcg tccaacatga ggaatgcagc aggccaattc atcgaggctg    6900
cctatgcaaa agcacttaga attgaacttg cccagttggt gcaggttgat aaggttcgag    6960
gtactttggc caagcttgag gcttttgctg ataccgtggc accccaactc tcgcccggtg    7020
acattgttgt tgctcttggc catacgcctg ttggcagcat cttcgaccta aaggttggtg    7080
gtaccaagca tactctccaa gtcattgaga ccagagtcct tgccgggtcc aaaatgaccg    7140
tggcgcgcgt cgttgaccca accccacgc ccccacccgc accgtgccc atccccctcc      7200 caccgaaagt tctagagaat ggtcccaacg cctggggga tggggaccgt ttgaataaga    7260
agaagaggcg taggatggaa accgtcggca tctttgtcat gggtgggaag aagtaccaga    7320
aattttggga caagaattcc ggtgatgtgt tttacgagga ggtccatgac aacacagatg    7380
cgtgggagtg cctcagagtt ggtgaccctg ccgactttaa ccctgagaag ggaactctgt    7440
gtgggcatac tactattgaa gataaggatt acaaagtcta cgcctcccca tctggcaaga    7500
agttcctggt ccccgtcaac ccagagagcg gaagagccca atgggaagct gcaaagcttt    7560
ccgtggagca ggcccttggc atgatgaatg tcgacggtga actgacggcc aaagaagtgg    7620
agaaactgaa aagaataatt gacaaacttc agggcctgac taaggagcag tgtttaaact    7680
gctagccgcc agcggcttga cccgctgtgg tcgcggcggc ttggttgtta ctgagacagc    7740
ggtaaaaata gtcaaatttc acaaccggac tttcaccta gggcctgtga atttaaaagt    7800
ggccagtgag gttgagctga aagacgcggt cgagcacaac caacacccgg ttgcaagacc    7860
ggttgacggt ggtgttgtgc tcctgcgttc cgcagttcct tcgcttatag atgtcctgat    7920
ctccggtgct gacgcatctc ctaagttact cgctcgtcac gggccgggga acactgggat    7980
cgatggcacg ctttgggact ttgaggccga ggccaccaaa gaggaaattg cgctcagtgc    8040
gcaaataata caggcttgtg acattaggcg cggtgacgca cctgaaattg gtctccctta    8100
caagctgtac cctgttaggg caaccctga gcggtaaaa ggagttttac agaatacaag     8160
gtttggagac ataccttaca aaccccccag tgacactggg agcccagtgc acgcggctgc    8220
ctgcctcacg cccaatgcca ctccggtgac tgatgggcgc tccgtcttgg ctactaccat    8280
gccctccggt tttgaattgt atgtaccgac cattccagcg tctgtccttg attatcttga    8340
ctctaggcct gactgcccca aacagttgac agagcacggc tgtgaggatg ccgcattgag    8400
agacctctcc aagtatgact tgtccaccca aggctttgtt ttacctgggg ttcttcgcct    8460
tgtgcgtaag tacctgtttg cccacgtggg taagtgcccg cccgttcatc ggccttccac    8520
```

```
ttaccctgcc aagaattcta tggctggaat aaatgggaac aggtttccaa ccaaggacat    8580
tcagagcgtc cccgaaatcg acgttctgtg cgcacaggcc gtgcgagaaa actggcaaac    8640 tgttaccct tgtaccctca agaaacagta ttgtgggaag aagaagacta ggacaatact    8700
cggcaccaat aatttcattg cgttggccca ccgggcagcg ttgagtggtg tcacccaggg    8760
cttcatgaaa aaggcgttta actcgcccat cgccctcggg aaaaacaaat ttaaggagct    8820
acagactccg atcttaggca ggtgccttga agctgatctt gcatcctgtg atcgatccac    8880
acctgcaatt gtccgctggt ttgccgccaa ccttctttat gaacttgcct gtgctgaaga    8940
gcacctaccg tcgtacgtgc tgaactgctg ccatgaccta ttggtcacgc agtccggcgc    9000
agtgactaag aggggtggcc tgtcgtctgg cgacccgatc acttctgtgt ctaacaccat    9060
ttacagcttg gtgatatatg cacagcacat ggtgcttagt tactttaaaa gtggtcaccc    9120
tcatggcctt ctgttcctac aagaccagct gaagttcgag acatgctca aagtccaacc    9180 cctgatcgtc tattcggacg acctcgtgct gtatgccgaa tctcccacca tgccgaacta    9240
ccactggtgg gtcgaacatc tgaatttgat gctgggtttt cagacggacc caaagaagac    9300
agccataacg gactcgccat catttctagg ctgtaggata taaatggac gccagctagt    9360 ccccaaccgt gacaggatcc tcgcggccct cgcttaccat atgaaggcaa gcaatgtttc    9420
tgaatactac gccgcggcgg ctgcaatact catggacagc tgtgcttgtt tagagtatga    9480
tcctgaatgg tttgaagagc ttgtggttgg atagcgcag tgcgcccgca aggacggcta    9540
cagctttccc ggcccgccgt tcttcttgtc catgtgggaa aaactcagat ccaatcatga    9600
ggggaagaag tccagaatgt gcgggtattg cggggccccg ctccgtacg ccactgcctg    9660 tggcctcgac gtctgtattt accacaccca cttccaccag cattgtccag tcacaatctg    9720
gtgtggccac ccggctggtt ctggttcttg tagtgagtgc aaaccccccc tagggaaagg    9780
cacaagccct ctagatgagg tgttagaaca agtcccgtat aagcctccac ggactgtaat    9840
catgcatgtg gagcagggtc tcaccctct gacccaggc agataccaga ctcgccgcgg    9900
attagtctcc gttaggcgtg gcatcagagg aaatgaagtt gacctaccag acggtgatta    9960
tgctagcacc gccctactcc ccacttgtaa agagatcaac atggtcgctg tcgcctctaa   10020
tgtgttgcgc agcaggttca tcatcggtcc gcccggtgct gggaaaacat actggctcct   10080
tcagcaggtc caggatggtg atgtcattta cacaccgact caccagacca tgctcgacat   10140
gattagggct ttggggacgt gccggttcaa cgtcccagca ggtacaacgc tgcaattccc   10200
tgccccctcc cgtaccggcc cgtgggttcg catcctagcc ggcggttggt gtcctggtaa   10260
gaattccttc ttggatgaag cagcgtattg taatcaccct gatgtcttga ggctccttag   10320
caaaaccacc ctcacctgtc tgggagactt caaacaactc cacccagtgg gtttgattc   10380 tcattgctat gttttgaca tcatgcctca gacccagttg aagaccatct ggagattcgg   10440
acagaacatc tgtgatgcca tccaaccaga ttacagggac aaacttgtgt ccatggtcaa   10500
cacaacccgt gtaacctacg tggaaaaacc tgtcaagtat gggcaagtcc tcacccctta   10560
ccacagggac cgagaggacg gcgccatcac aattgactcc agtcaaggcg ccacatttga   10620
tgtggtcaca ctgcatttgc ccactaaaga ttcactcaac aggcaaagag cccttgttgc   10680
tatcaccagg gcaagacatg ctatctttgt gtatgaccca cacaggcaat tgcagagcat   10740
gtttgatctt cctgcgaagg gcacacccgt caacctcgca gtgcaccgtg atgagcagct   10800
gatcgtactg gatagaaata taaagaatg cacagttgct caggctctag caacggaga   10860 taaatttagg gccaccgaca agcgcgttgt agattctctc cgcgccattt gtgctgatct   10920
```

```
ggaagggtcg agctctccgc tccccaaggt cgcacacaac ttgggatttt atttctcacc    10980
tgatttgaca cagtttgcta aactcccggt agaccttgca ccccactggc ccgtggtgac    11040
aacccagaac aatgaaaagt ggccggatcg gctggttgcc agccttcgcc ctgtccataa    11100
gtatagccgt gcgtgcattg gtgccggcta tatggtgggc ccctcggtgt ttctaggcac    11160
ccctggggtc gtgtcatact acctcacaaa atttgtcaag gcgaggctc aagtgcttcc     11220 ggagacagtc ttcagcaccg gccgaattga ggtggattgc cggagtatc ttgatgacag     11280 ggagcgagaa gttgctgagt ccctcccaca tgccttcatt ggcgacgtca aaggcaccac    11340
cgttggggga tgtcatcatg tcacctccaa atacctccg cgcttcctc ccaaggaatc      11400 agtcgcggta gtcggggttt cgagcccgg gaaagccgca aaagcagtgt gcacattgac     11460
ggatgtgtac ctcccagacc ttgaggccta cctccaccca gagactcagt ccaagtgctg    11520
gaaagttatg ttggacttca aggaagttcg actgatggtc tggaaagaca agacggccta    11580
tttccaactt gaaggccgct atttcacctg gtatcagctt gcaagctacg cctcgtacat    11640
ccgtgttcct gtcaactcca cggtgtatct ggaccctgc atgggccctg ccctttgcaa     11700
cagaagagtt gtcgggtcca cccattgggg agctgacctc gcagtcaccc cttatgatta    11760
cggtgctaaa atcatcttgt ctagcgctta ccatggtgaa atgcctcctg gatacaagat    11820
tctggcgtgc gcggagttct cgctcgacga cccagtcaag tacaaacaca cctgggggttt   11880 tgaatcggat acagcgtatc tgtatgagtt caccggaaac ggtgaggact gggaggatta    11940
caatgatgcg tttcgtgcgc gccagaaagg gaaaatttat aaggccactg ctaccagcat    12000
gaagttttat tttcccccgg gccccgtcat tgaaccaact ttaggcctga attgaaatga    12060
aatggggtct atacaaagcc tcttcgacaa aattggccag cttttttgtgg atgctttcac   12120 ggaattttg gtgtccattg ttgatatcat catatttttg gccatttgt ttggcttcac      12180 catcgccgt tggctggtgg tcttttgcat cagattggtt tgctccgcgg tattccgtgc     12240
gcgccctgcc attcaccctg agcaattaca gaagatccta tgaggccttt ctttctcagt    12300
gccgggtgga cattcccacc tgggggtaa acacccttt ggggatgttt tggcaccata      12360
aggtgtcaac cctgattgat gaaatggtgt cgcgtcgaat gtaccgcatc atggaaaaag    12420
cagggcaagc tgcctggaaa caggtggtga gcgaggctac gctgtctcgc attagtagtt    12480
tggatgtggt ggctcatttt caacatcttg ccgccattga agccgagacc tgtaaatatt    12540
tggcttctcg actgcccatg ctacacaacc tgcgcatgac agggtcaaat gtaaccatag    12600
tgtataatag cactttaaat caggtgtttg ctatttttcc aacccctggt tcccggccaa    12660
agcttcatga ttttcagcaa tggctaatag ctgtacattc ctccatattt tcctctgttg    12720
cagcttcttg tactctttt gttgtgctgt ggttgcgggt tccaatgcta cgtactgttt     12780
ttggtttccg ctggttaggg gcaattttc tttcgaactc atggtgaatt acacggtgtg    12840
tccaccttgc ctcacccgac aagcagccgc tgaggtcctt gaacccggta ggtctctttg    12900
gtgcaggata gggcatgacc gatgtgggga ggacgatcac gacgaactgg ggttcatggt    12960
tccgcctggc ctctccagcg aaagccactt gaccagtgtt tacgcctggt tggcgttcct    13020
gtccttcagc tacacggccc agttccatcc cgagatattt gggataggga acgtgagtga    13080
agtttatgtt gacatcaagc accaattcat ctgcgccgtt catgacgggc agaacaccac    13140
cttgcctcgc catgacaaata tttcagccgt atttcagacc tactatcaac atcaggtcga    13200
cggcggcaat tggtttcacc tagaatggct gcgtcccttc ttttcctctt ggttggtttt    13260
```

-continued

```
aaatgtttcg tggtttctca ggcgttcgcc tgcaagccat gtttcagttc gagtctttca    13320
gacatcaaaa ccaacactac cgcagcatca ggctttgttg tcctccagga catcagctgc    13380
cttaggcatg gcgactcgtc ctttccgacg attcgcaaaa gctctcaatg ccgcacggcg    13440
atagggacac ctgtgtatat caccatcaca gccaatgtga cagatgagaa ttacttacat    13500
tcttctgatc tcctcatgct ttcttcttgc cttttctatg cttctgagat gagtgaaaag    13560
ggattcaagg tggtatttgg caatgtgtca ggcatcgtgg ctgtgtgtgt caactttacc    13620
agctacgtcc aacatgtcaa agagtttacc caacgctcct tggtggtcga tcatgtgcgg    13680
ctgcttcatt tcatgacacc tgagaccatg aggtgggcaa ccgttttagc ctgtcttttt    13740
gccatcctac tggcaatttg aatgttcaag tatgttgggg aaatgcttga ccgcgggctg    13800
ttgctcgcga ttgctttctt tgtggtgtat cgtgccgttc tggtttgctg tgctcggcaa    13860
cgccaacagc agcagcagct ctcatttcca gttgatttat aacttgacgc tatgtgagct    13920
gaatggcaca gattggctgg cagaaaaatt tgattgggca gtggagactt ttgtcatctt    13980
tcccgtgttg actcacattg tttcctatgg tgcactcacc accagccatt tccttgacac    14040
agttggtctg gttactgtgt ccaccgccgg gttttatcac gggcggtatg tcttgagtag    14100
catctacgcg gtctgtgctc tggctgcgtt gatttgcttc gttattaggc ttgcgaagaa    14160
ctgcatgtcc tggcgctact cttgtaccag atataccaac ttccttctgg acactaaggg    14220
cagactctat cgttggcggt cgcccgttat catagaaaaa gggggtaagg ttgaggtcga    14280
aggtcatctg atcgacctca aaagagttgt gcttgatggt tccgtggcaa cccctttaac    14340
cagagtttca gcggaacaat ggggtcgtct ctagacgact tttgccatga tagcacggct    14400
ccacaaaagg tgcttttggc gttttccatt acctacacgc cagtaatgat atatgctcta    14460
aaggtaagtc gcggccgact gctagggctt ctgcacccttt tgatctttct gaattgtgct    14520
tttaccttcg ggtacatgac attcgcgcac tttcagagca caaatagggt cgcgctcgct    14580
atgggagcag tagttgcact tctttggggg gtgtactcag ccatagaaac ctggaaattc    14640
atcacctcca gatgccgttt gtgcttgcta ggccgcaagt acattctggc ccctgcccac    14700
cacgtcgaaa gtgccgcggg cttcatccg attgcggcaa atgataacca cgcatttgtc    14760
gtccggcgtc ccggctccat tacggttaac ggcacattgg tgcccgggtt gaaaagcctc    14820
gtgttgggtg gcagaaaagc tgttaaacag ggagtggtaa accttgtcaa atatgccaaa    14880
taacaacggc aagcagcaaa agaaaaagaa ggggaatggc cagccagtca accagctgtg    14940
ccagatgctg ggtaaaatca tcgcccagca aaaccagtcc agaggcaagg gaccgggctc    15000
taagaagaaa tccccggaga agccccattt tcctctagcg accgaagatg acgtcaggca    15060
tcacttcacc cctggtgagc ggcaattgtg tctgtcgtcg atccagactg cctttaacca    15120
gggcgctgga acttgtaccc tgtcagattc agggaggata agttacactg tggagtttag    15180
tttgccgacg catcatactg tgcgcctgat ccgcgtcaca gcatcaccct cagcatgatg    15240
ggctggcatt ctttaggcac ctcagtgtca gaattggaag aatgtgtggt ggatggcact    15300
gattgacatt gtgcctctaa gtcacctatt caattagggc gaccgtgtgg gggtaaaatt    15360
taattggcga gaaccatgcg gccgcaatta aaaaaaaaaa aaaaaaaaaa aaaaaaaaaa    15420
aaaaaaaaaa aaaaaaaaaa aaaa                                          15444
```

<210> SEQ ID NO 3
<211> LENGTH: 15450
<212> TYPE: DNA
<213> ORGANISM: Artificial Sequence
<220> FEATURE:
<223> OTHER INFORMATION: P129-PK-FL passage 24 complete genome (15,450 nt) full length vaccine

<400> SEQUENCE: 3

```
atgacgtata ggtgttggct ctatgccacg gcatttgtat tgtcaggagc tgtgaccatt      60
ggcacagccc aaaacttgct gcacggaaaa cgcccttctg tgacagcctt cttcagggga     120
gcttaggggt ctgtccctag caccttgctt ctggagttgc actgctttac ggtctctcca     180
cccctttaac catgtctggg atacttgatc ggtgcacgtg cacccccaat gccagggtgt     240
ttatggcgga gggccaagtc tactgcacac gatgtctcag tgcacggtct ctccttcctc     300
tgaatctcca agttcctgag cttggggtgc tgggcctatt ttataggccc gaagagccac     360
tccggtggac gttgccacgt gcattcccca ctgtcgagtg ctcccctgcc ggggcctgct     420
ggctttctgc gatctttcca attgcacgaa tgaccagtgg aaacctgaac tttcaacaaa     480
gaatggtgcg ggttgcagct gagatttaca gagccggcca actcacccct gcagttttga     540
aggctctaca agtttatgaa cggggttgtc gctggtaccc cattgtcgga cctgtccctg     600
gagtggccgt ttacgccaac tccctacatg tgagtgacaa cctttcccg ggagcaactc     660
atgtgttaac caacctaccg ctcccgcaga ggcccaagcc tgaagacttt tgccctttg      720
agtgtgctat ggctaacgtc tatgacattg ccataacgc cgtcatgtat gtggccagag      780
ggaaagtctc ctgggcccct cgtggcgggg atgaagtgaa atttgaaacc gtccccgaag     840
agttgaagtt gattgcgaac cgactccaca tctccttccc gccccaccac gcagtggaca     900
tgtctgagtt tgccttcata gcccctggga gtggtgtctc cttgcgggtc gagcaccaac     960
acggctgcct tcccgctgat actgtccctg atgggaactg ctggtggtac ttgtttgact    1020
tgctcccacc ggaagttcag aataaagaaa ttcgccgtgc taaccaattt ggctatcaaa    1080
ccaagcatgg tgtccatggc aagtacctac agcggaggct gcaagttaat ggtctccgag    1140
cagtgactga tacagatgga cctattgtcg tacagtactc tctgttagg gagagttgga    1200
tccgccactt cagactggcg gaagaaccta gcctccctgg gtttgaagac tcctcagaa     1260
taagggtaga gcctaatacg tcgccaatgg gtggcaaggg tgaaaaaatc ttccggttg     1320
gcagtcacaa gtggtacggt gctggaaaga gagcaaggag agcacgctct ggtgcgactg    1380
ccacggtcgc tcaccgcgct ttgccccgctc gcgaagccca gcaggccaag aagctcgagg    1440
ttgccagcgc caacagggct gagcatctca gtactattc cccgcctgcc gacgggaact    1500
gtggttggca ctgcatttcc gccattacca accggatggt gaattccaaa tttgaaacca    1560
ctcttcccga gagagtgaga ccttcagatg actgggctac tgacgaggat cttgtgaata    1620
ccatccaaat cctcaggctc cccgcggcct tggacaggaa cggtgcttgt gctggcgcca    1680
agtacgtgct caagctggaa ggtgagcact ggaccgtctc tgtgacccct gggatgaccc    1740
cttctttgct ccccctttgaa tgtgttcagg gttgttgtga gcataagagc ggtcttggtt    1800
tcccagacgt ggtcgaagtt tccggatttg accctgcctg tcttgaccga cttgctgaga    1860
taatgcactt gcctagcagt gtcatcccag ctgctctggc cgagatgtcc gacgacttca    1920
atcgtctggc ttccccggcc gccactgtgt ggactgtttc gcaattcttt gcccgccaca    1980
gaggaggaga gcatcctgac caggtgtgct tagggaaaat tatcaacctt gtcaggtga    2040
ttgaggaatg ctgctgttcc cggaacaaag ccaaccgggc tacccgggaa gaggttgcgg    2100
caaaagttga ccagtacctc cgtggtgcag caagccttgg agaatgcttg gccaagcttg    2160
agagggctcg cccgccgagc gcgacggaca cctccttga ttggaatgtt gtgcttcctg     2220
```

```
gggttgagac ggcgaatcag acaaccaaac agctccatgt caaccagtgc cgcgctctgg    2280
ttcctgtcgt gactcaagag cctttggaca gagactcggt ccctctgacc gccttctcgc    2340
tgtccaattg ctactaccct gcacaaggtg acgaggtccg tcaccgtgag aggctaaact    2400
ccttgctctc taagttggag ggggttgttc gtgaggaata tgggctcacg ccaactggac    2460
ctggcccgcg acccgcactg ccgaacgggc tcgacgagct taaagaccag atggaggagg    2520
atctgctgaa attagtcaac gcccaggcaa cttcagaaat gatggcctgg gcagccgagc    2580
aggttgatct aaaagcttgg gtcaaaaatt acccacggtg gacaccgcca cccctccac     2640
caagagttca gcctcgaaaa acgaagtctg tcaagagctt gctagagaac aagcctgtcc    2700
ctgctccgcg caggaaggtc agatctgatt gtggcagccc gattttgatg ggcgacaatg    2760
ttcctaacgg ttgggaagat tcgactgttg gtggtcccct tgatctttcg gcaccatccg    2820
agccgatgac acctctgagt gagcctgtac ttatttccag gccagtgaca tctttgagtg    2880
tgccggcccc agttcctgca ccgcgtagag ctgtgtcccg accgatgacg ccctcgagtg    2940
agccaatttt tgtgtctgca ctgcgacaca aatttcagca ggtggaaaaa gcaaatctgg    3000
cggcagcagc gccgatgtgc caggacgaac ccttagattt gtctgcatcc tcacagactg    3060
aatatgaggc ttcccccctA acaccaccgc agaacgtggg cattctggag gtaaggggcc    3120
aagaagctga ggaagttctg agtgaaatct cggatattct gaatgatacc aaccctgcac    3180
ctgtgtcatc aagcagctcc ctgtcaagtg ttaagatcac acgcccaaaa tactcagctc    3240
aagccattat cgactcgggc gggccctgca gtgggcacct ccaaagggaa aaagaagcat    3300
gcctccgcat catgcgtgag gcttgtgatg cggccaagct tagtgaccct gccacgcagg    3360
aatggctttc tcgcatgtgg gatagggtgg acatgctgac ttggcgcaac acgtctgctt    3420
accaggcgtt tcgcacctta gatggcaggt ttgggtttct cccaaagatg atactcgaga    3480
cgccgccgcc ctaccgtgt gggttttgtga tgttgcctca cacccctgca ccttccgtga    3540
gtgcagagag cgaccttacc attggttcag tcgccactga agatattcca cgcatcctcg    3600
ggaaaataga aaataccggt gagatgatca accaggacc cttggcatcc tctgaggaag    3660
aaccggtata caaccaacct gccaaagact cccggatatc gtcgcggggg tctgacgaga    3720
gcacagcagc tccgtccgcg ggtacaggtg gcgccggctt atttactgat ttgccacctt    3780
cagacggcgt agatgcggac ggtgggggc cgttgcagac ggtaagaaag aaagctgaaa    3840
ggctcttcga ccaattgagc cgtcaggttt ttaacctcgt ctcccatctc cctgttttct    3900
tctcacacct cttcaaatct gacagtggtt attctccggg tgattggggt tttgcagctt    3960
ttactctatt ttgcctcttt ttgtgttaca gctacccatt cttcggtttc gttcccctct    4020
tgggtgtatt ttctgggtct tctcggccgt gcgcatggg ggttttggc tgctggctgg     4080
cttttgctgt tggcctgttc aagcctgtgt ccgacccagt cggcactgct tgtgagtttg    4140
actcgccaga gtgcaggaac gtccttcatt cttttgagct tctcaaacct tgggaccctg    4200
ttcgcagcct tgttgtgggc cccgtcggtc tcggtcttgc cattcttggc aggttactgg    4260
gcggggcacg ctacatctgg cattttttgc ttaggcttgg cattgttgca gattgtatct    4320
tggctggagc ttatgtgctt tctcaaggta ggtgtaaaaa gtgctgggga tcttgtataa    4380
gaactgctcc taatgaaatc gccttcaacg tgttcccttt tacacgtgcg accaggtcgt    4440
cactcatcga cctgtgcgat cggttttgtg cgccaacagg catggacccc attttcctcg    4500
ccactgggtg gcgtgggtgc tggaccggcc gaagtcccat tgagcaaccc tctgaaaaac    4560
```

```
ccatcgcgtt cgcccagttg gatgaaaaga ggattacggc tagaactgtg gtcgctcagc    4620
cttatgatcc taatcaagcc gtgaagtgct tgcgggtgtt acaggcgggt ggggcgatgg    4680
tggccgaggc agtcccaaaa gtggccaaag tttctgctat tccattccga gccccttttt    4740
ttcccaccgg agtgaaagtt gatcccgagt gcaggatcgt ggttgacccc gatactttta    4800
ctacagccct ccggtctggt tactctacca caaacctcgt ccttggtgtg ggggactttg    4860
cccagctgaa tggactaaag atcaggcaaa tttccaagcc ttcgggagga ggcccacacc    4920
tcattgctgc cctgcatgtt gcctgctcga tggcgttgca catgcttgct ggggtttatg    4980
taacttcagt ggggtcttgc ggtgccggca ccaacgatcc atggtgcact aatccgtttg    5040
ccgttcctgg ctacggacca ggctctctct gcacgtccag attgtgcatc tcccaacatg    5100
gccttaccct gcccttgaca gcacttgtgg cgggattcgg tcttcaggaa atcgccttgg    5160
tcgttttgat tttcgtttcc atcggaggca tggctcatag gttgagttgt aaggctgata    5220
tgctgtgcat tttacttgca atcgccagct atgtttgggt acccctacc tggttgcttt    5280 gtgtgtttcc ttgttggttg cgctggttct ctttgcaccc ccttaccatc ctatggttgg    5340 tgttttctt gatttctgta aatatgcctt cgggaatctt ggccgtggtg ttattggttt    5400
ctctttggct tttgggacgt tatactaaca ttgctggtct tgtcaccccc tatgatattc    5460
atcattacac cagtggcccc cgcggtgttg ccgccttggc taccgcacca gatggaacct    5520
acttggctgc cgtccgccgc gctgcgttga ctggtcgcac catgctgttc acccccgtctc    5580 agcttgggtc ccttcttgag ggcgctttca gaactcgaaa gccctcactg aacaccgtca    5640
atgtggttgg gtcctccatg ggctctggtg gagtgttcac catcgacggg aaaattaggt    5700
gcgtgactgc cgcacatgtc cttacgagta attcggctag ggtttccgga gtcggcttca    5760
atcaaatgct tgactttgat gtgaaagggg acttcgccat agctgattgc ccgaattggc    5820
aaggagctgc tcccaagacc caattctgcg aggacggatg gactggccgt gcctattggc    5880
tgacatcctc tggcgtcgaa cccgtgttat tgggaatgg attcgccttc tgcttcaccg    5940
cgtgcggcga ttccgggtcc ccagtgatca ccgaagctgg tgagattgtc ggcgttcaca    6000
caggatcaaa taacaagga ggtggcatcg tcacgcgccc ttcaggccag ttttgtaacg    6060
tggcacccat caagctgagc gaattaagtg aattctttgc tggacccaag gtcccgctcg    6120
gtgatgtgaa ggttggcagc cacataatta agacacgtg cgaagtacct tcagatcttt    6180
gcgccttgct tgctgccaaa cctgaactgg agggaggcct ctccaccgtc caacttctgt    6240
gtgtgttttt cctactgtgg agaatgatgg gacatgcctg gacgcccttg gttgctgtgg    6300 ggttttttcat tctgaatgag gttctcccag ctgtcctggt tcggagtgtt ttctcctttg    6360
ggatgtttgt gctatcttgg ctcacaccat ggtctgcgca gttctgatg atcaggcttc    6420 taacagcagc tcttaacagg aacagatggt cacttgcctt ttacagcctt ggtgcggtga    6480 ccggtttgt cgcagatctt gcggtaactc aagggcaccc gttgcaggca gtaatgaatt    6540
tgagcaccta tgccttcctg cctcggatga tggttgtgac ctcaccagtc ccagtgattg    6600
cgtgtggtgt tgtgcaccta cttgccatca ttttgtactt gttcaagtac cgcggcctgc    6660
acaatgttct tgttggtgat ggagcgtttt ctgcagcttt cttcttgcga tactttgccg    6720
agggaaagtt gagggaaggg gtgtcgcaat cctgcggaat gaatcatgag tcattgactg    6780
gtgccctcgc tatgagactc aatgacgagg acttggactt ccttacgaaa tggactgatt    6840
ttaagtgctt tgtttctgcg tccaacatga ggaatgcagc aggccaattc atcgaggctg    6900
cctatgcaaa agcacttaga attgaacttg cccagttggt gcaggttgat aaggttcgag    6960
```

```
gtactttggc caagcttgag gcttttgctg ataccgtggc accccaactc tcgcccggtg   7020
acattgttgt tgctcttggc catacgcctg ttggcagcat cttcgaccta aaggttggtg   7080
gtaccaagca tactctccaa gtcattgaga ccagagtcct tgccgggtcc aaaatgaccg   7140
tggcgcgcgt cgttgaccca accccacgc ccccacccgc accgtgccc atccccctcc    7200 caccgaaagt tctagagaat ggtcccaacg cctgggggga tggggaccgt ttgaataaga   7260
agaagaggcg taggatggaa accgtcggca tctttgtcat gggtgggaag aagtaccaga   7320
aattttggga caagaattcc ggtgatgtgt tttacgagga ggtccatgac aacacagatg   7380
cgtgggagtg cctcagagtt ggtgaccctg ccgactttaa ccctgagaag gaactctgt    7440 gtgggcatac tactattgaa gataaggatt acaaagtcta cgcctcccca tctggcaaga   7500
agttcctggt ccccgtcaac ccagagagcg gaagagccca tgggaagct gcaaagcttt    7560 ccgtggagca ggcccttggc atgatgaatg tcgacggtga actgacggcc aagaagtgg    7620 agaaactgaa aagaataatt gacaaacttc agggcctgac taaggagcag tgtttaaact   7680
gctagccgcc agcggcttga cccgctgtgg tcgcggcggc ttggttgtta ctgagacagc   7740
ggtaaaaata gtcaaatttc acaaccggac tttcaccctg gggcctgtga atttaaaagt   7800
ggccagtgag gttgagctga aagacgcggt cgagcacaac caacacccgg ttgcaagacc   7860
ggttgacggt ggtgttgtgc tcctgcgttc cgcagttcct tcgcttatag atgtcctgat   7920
ctccggtgct gacgcatctc ctaagttact cgctcgtcac gggccgggga acactgggat   7980
cgatggcacg ctttgggact ttgaggccga ggccaccaaa gaggaaattg cgctcagtgc   8040
gcaaataata caggcttgtg acattaggcg cggtgacgca cctgaaattg gtctcccta    8100 caagctgtac cctgttaggg gcaaccctga gcgggtaaaa ggagttttac agaatacaag   8160
gtttggagac ataccttaca aaaccccag tgacactggg agcccagtgc acgcggctgc    8220
ctgcctcacg cccaatgcca ctccggtgac tgatgggcgc tccgtcttgg ctactaccat   8280
gccctccggt tttgaattgt atgtaccgac cattccagcg tctgtccttg attatcttga   8340
ctctaggcct gactgcccca aacagttgac agagcacggc tgtgaggatg ccgcattgag   8400
agacctctcc aagtatgact tgtccaccca aggctttgtt ttacctgggg ttcttcgcct   8460
tgtgcgtaag tacctgtttg cccacgtggg taagtgcccg cccgttcatc ggccttccac   8520
ttaccctgcc aagaattcta tggctggaat aaatgggaac aggtttccaa ccaaggacat   8580
tcagagcgtc cccgaaatcg acgttctgtg cgcacaggcc gtgcgagaaa actggcaaac   8640
tgttacccct tgtaccctca agaaacagta ttgtgggaag aagaagacta ggacaatact   8700
cggcaccaat aatttcattg cgttggccca ccgggcagcg ttgagtggtg tcacccaggg   8760
cttcatgaaa aaggcgttta actcgcccat cgccctcggg aaaaacaaat ttaaggagct   8820
acagactccg atcttaggca ggtgccttga agctgatctt gcatcctgtg atcgatccac   8880
acctgcaatt gtccgctggt ttgccgccaa ccttctttat gaacttgcct gtgctgaaga   8940
gcacctaccg tcgtacgtgc tgaactgctg ccatgaccta ttggtcacgc agtccggcgc   9000
agtgactaag aggggtggcc tgtcgtctgg cgacccgatc acttctgtgt ctaacaccat   9060
ttacagcttg gtgatatatg cacagcacat ggtgcttagt tactttaaaa gtggtcaccc   9120
tcatggcctt ctgttcctac aagaccagct gaagttcgag gacatgctca agtccaacc    9180 cctgatcgtc tattcggacg acctcgtgct gtatgccgaa tctcccacca tgccgaacta   9240
ccactggtgg gtcgaacatc tgaatttgat gctgggtttt cagacggacc caagaagac   9300
```

-continued

```
agccataacg gactcgccat catttctagg ctgtaggata taaatggac gccagctagt    9360
ccccaaccgt gacaggatcc tcgcggccct cgcttaccat atgaaggcaa gcaatgtttc   9420
tgaatactac gccgcggcgg ctgcaatact catggacagc tgtgcttgtt tagagtatga   9480
tcctgaatgg tttgaagagc ttgtggttgg gatagcgcag tgcgcccgca aggacggcta   9540
cagctttccc ggcccgccgt tcttcttgtc catgtgggaa aaactcagat ccaatcatga   9600
ggggaagaag tccagaatgt gcgggtattg cggggccccg gctccgtacg ccactgcctg   9660
tggcctcgac gtctgtattt accacaccca cttccaccag cattgtccag tcacaatctg   9720
gtgtggccac ccggctggtt ctggttcttg tagtgagtgc aaaccccccc tagggaaagg   9780
cacaagccct ctagatgagg tgttagaaca agtcccgtat aagcctccac ggactgtaat   9840
catgcatgtg gagcagggtc tcaccccctct tgacccaggc agataccaga ctcgccgcgg   9900
attagtctcc gttaggcgtg gcatcagagg aaatgaagtt gacctaccag acggtgatta   9960
tgctagcacc gccctactcc ccacttgtaa agagatcaac atggtcgctg tcgcctctaa  10020
tgtgttgcgc agcaggttca tcatcggtcc gcccggtgct gggaaaacat actggctcct  10080
tcagcaggtc caggatggtg atgtcattta cacaccgact caccagacca tgctcgacat  10140
gattagggct ttggggacgt gccggttcaa cgtcccagca ggtacaacgc tgcaattccc  10200
tgcccccctcc cgtaccggcc cgtgggttcg catcctagcc ggcggttggt gtcctggtaa  10260
gaattccttc ttggatgaag cagcgtattg taatcacctt gatgtcttga ggctccttag  10320
caaaaccacc ctcacctgtc tgggagactt caaacaactc cacccagtgg gttttgattc  10380
tcattgctat gttttttgaca tcatgcctca gacccagttg aagaccatct ggagattcgg  10440
acagaacatc tgtgatgcca tccaaccaga ttacagggac aaacttgtgt ccatggtcaa  10500
cacaacccgt gtaacctacg tggaaaaacc tgtcaagtat gggcaagtcc tcacccctta  10560
ccacagggac cgagaggacg gcgccatcac aattgactcc agtcaaggcg ccacatttga  10620
tgtggtcaca ctgcatttgc ccactaaaga ttcactcaac aggcaaagag cccttgttgc  10680
tatcaccagg gcaagacatg ctatctttgt gtatgaccca cacaggcaat gcagagcat   10740
gtttgatctt cctgcgaagg gcacacccgt caacctcgca gtgcaccgtg atgagcagct  10800
gatcgtactg gatagaaata taaagaatg cacagttgct caggctctag caacggaga   10860
taaatttagg gccaccgaca agcgcgttgt agattctctc cgcgccattt gtgctgatct  10920
ggaagggtcg agctctccgc tccccaaggt cgcacacaac ttgggatttt atttctcacc  10980
tgatttgaca cagtttgcta aactcccggt agaccttgca ccccactggc ccgtggtgac  11040
aacccagaac aatgaaaagt ggccggatcg gctggttgcc agccttcgcc ctgtccataa  11100
gtatagccgt gcgtgcattg gtgccggcta tatggtgggc cctcggtgt ttctaggcac   11160
ccctggggtc gtgtcatact acctcacaaa atttgtcaag ggcgaggctc aagtgcttcc  11220
ggagacagtc ttcagcaccg gccgaattga ggtggattgc cggagtatc ttgatgacag   11280
ggagcgagaa gttgctgagt ccctcccaca tgccttcatt ggcgacgtca aaggcaccac  11340
cgttggggga tgtcatcatg tcacctccaa ataccttccg cgcttccttc caaggaatc   11400
agtcgcggta tcgggggttt cgagcccggg gaaagccgca aaagcagtgt gcacattgac  11460
ggatgtgtac ctcccagacc ttgaggccta cctccaccca gagactcagt ccaagtgctg  11520
gaaagttatg tttggacttca aggaagttcg actgatggtc tggaaagaca agacggccta  11580
tttccaactt gaaggccgct atttcacctg gtatcagctt gcaagctacg cctcgtacat  11640
ccgtgttcct gtcaactcca cggtgtatct ggacccctgc atgggccctg ccctttgcaa  11700
```

```
cagaagagtt gtcgggtcca cccattgggg agctgacctc gcagtcaccc cttatgatta   11760
cggtgctaaa atcatcttgt ctagcgctta ccatggtgaa atgcctcctg gatacaagat   11820
tctggcgtgc gcggagttct cgctcgacga cccagtcaag tacaaacaca cctggggttt   11880
tgaatcggat acagcgtatc tgtatgagtt caccggaaac ggtgaggact gggaggatta   11940
caatgatgcg tttcgtgcgc gccagaaagg gaaaatttat aaggccactg ctaccagcat   12000
gaagttttat tttcccccgg gccccgtcat tgaaccaact ttaggcctga attgaaatga   12060
aatggggtct atacaaagcc tcttcgacaa aattggccag cttttttgtgg atgctttcac   12120 ggaattttttg gtgtccattg ttgatatcat catattttttg gccatttttgt ttggcttcac   12180 catcgccggt tggctggtgg tcttttgcat cagattggtt tgctccgcgg tattccgtgc   12240
gcgccctgcc attcaccctg agcaattaca gaagatccta tgaggccttt ctttctcagt   12300
gccgggtgga cattcccacc tgggggtaa acaccccttt ggggatgttt tggcaccata   12360
aggtgtcaac cctgattgat gaaatggtgt cgcgtcgaat gtaccgcatc atggaaaaag   12420
cagggcaagc tgcctggaaa caggtggtga gcgaggctac gctgtctcgc attagtagtt   12480
tggatgtggt ggctcatttt caacatcttg ccgccattga agccgagacc tgtaaatatt   12540
tggcttctcg actgcccatg ctacacaacc tgcgcatgac agggtcaaat gtaaccatag   12600
tgtataatag cactttaaat caggtgtttg ctatttttcc aacccctggt tcccggccaa   12660
agcttcatga ttttcagcaa tggctaatag ctgtacattc ctccatattt tcctctgttg   12720
cagcttcttg tactcttttt gttgtgctgt ggttgcgggt tccaatgcta cgtactgttt   12780
ttggtttccg ctggttaggg gcaatttttc tttcgaactc atggtgaatt acacggtgtg   12840
tccaccttgc ctcacccgac aagcagccgc tgaggtcctt gaacccggta ggtctctttg   12900
gtgcaggata gggcatgacc gatgtgggga ggacgatcac gacgaactgg ggttcatggt   12960
tccgcctggc ctctccagcg aaagccactt gaccagtgtt tacgcctggt tggcgttcct   13020
gtccttcagc tacacggccc agttccatcc cgagatattt gggataggga acgtgagtga   13080
agtttatgtt gacatcaagc accaattcat ctgcgccgtt catgacgggc agaacaccac   13140
cttgcctcgc catgacaata tttcagccgt atttcagacc tactatcaac atcaggtcga   13200
cggcggcaat tggtttcacc tagaatggct gcgtcccttc ttttcctctt ggttggtttt   13260
aaatgtttcg tggtttctca ggcgttcgcc tgcaagccat gtttcagttc gagtcttttca   13320 gacatcaaaa ccaacactac cgcagcatca ggctttgttg tcctccagga catcagctgc   13380
cttaggcatg gcgactcgtc cttttccgacg attcgcaaaa gctctcaatg ccgcacggcg   13440
atagggacac ctgtgtatat caccatcaca gccaatgtga cagatgagaa ttacttacat   13500
tcttctgatc tcctcatgct ttcttcttgc cttttctatg cttctgagat gagtgaaaag   13560
ggattcaagg tggtatttgg caatgtgtca ggcatcgtgg ctgtgtgtgt caactttacc   13620
agctacgtcc aacatgtcaa agagtttacc caacgctcct tggtggtcga tcatgtgcgg   13680
ctgcttcatt tcatgacacc tgagaccatg aggtgggcaa ccgtttttagc ctgtcttttt   13740 gccatcctac tggcaatttg aatgttcaag tatgttgggg aaatgcttga ccgcgggctg   13800
ttgctcgcga ttgcttttctt tgtggtgtat cgtgccgttc tggtttgctg tgctcggcaa   13860
cgccaacagc agcagcagct ctcatttttca gttgatttat aacttgacgc tatgtgagct   13920
gaatggcaca gattggctgg cagaaaaatt tgattgggca gtggagactt ttgtcatctt   13980
tcccgtgttg actcacattg tttcctatgg tgcactcacc accagccatt tccttgacac   14040
```

```
agttggtctg ttactgtgt ccaccgccgg gttttatcac gggcggtatg tcttgagtag   14100
catctacgcg gtctgtgctc tggctgcgtt gatttgcttc gttattaggc ttgcgaagaa   14160
ctgcatgtcc tggcgctact cttgtaccag atataccaac ttccttctgg acactaaggg   14220
cagactctat cgttggcggt cgcccgttat catagaaaaa gggggtaagg ttgaggtcga   14280
aggtcatctg atcgacctca aaagagttgt gcttgatggt tccgtggcaa cccctttaac   14340
cagagtttca gcggaacaat ggggtcgtct ctagacgact tttgccatga tagcacggct   14400
ccacaaaagg tgcttttggc gttttccatt acctacacgc cagtaatgat atatgctcta   14460
aaggtaagtc gcggccgact gctagggctt ctgcaccttt tgatcttcct gaattgtgct   14520
tttaccttcg ggtacatgac attcgcgcac tttcagagca caaatagggt cgcgctcgct   14580
atgggagcag tagttgcact tctttggggg gtgtactcag ccatagaaac ctggaaattc   14640
atcacctcca gatgccgttt gtgcttgcta ggccgcaagt acattctggc ccctgcccac   14700
cacgtcgaaa gtgccgcggg ctttcatccg attgcggcaa atgataacca cgcatttgtc   14760
gtccggcgtc ccggctccat tacgcttaac ggcacattgg tgcccgggtt gaaaagcctc   14820
gtgttgggtg gcagaaaagc tgttaaacag ggagtggtaa accttgtcaa atatgccaaa   14880
taacaacggc aagcagcaaa agaaaaagaa ggggaatggc cagccagtca accagctgtg   14940
ccagatgctg ggtaaaatca tcgcccagca aaaccagtcc agaggcaagg gaccgggcaa   15000
gaaaagtaag aagaaaaacc cggagaagcc ccatttttcct ctagcgaccg aagatgacgt   15060
caggcatcac ttcaccctg gtgagcggca attgtgtctg tcgtcgatcc agactgcctt   15120
taaccagggc gctggaactt gtaccctgtc agattcaggg aggataagtt acactgtgga   15180
gtttagtttg ccgacgcatc atactgtgcg cctgatccgc gtcacagcat caccctcagc   15240
atgatgggct ggcattcttt aggcacctca gtgtcagaat tggaagaatg tgtggtggat   15300
ggcactgatt gacattgtgc ctctaagtca cctattcaat tagggcgacc gtgtgggggt   15360
aaaatttaat tggcgagaac catgcggccg caattaaaaa aaaaaaaaaa aaaaaaaaa   15420 aaaaaaaaaa aaaaaaaaa aaaaaaaaa                                     15450
```

<210> SEQ ID NO 4
<211> LENGTH: 15444
<212> TYPE: DNA
<213> ORGANISM: Artificial Sequence
<220> FEATURE:
<223> OTHER INFORMATION: P129-PK-d43/44 passage 34 complete genome
      (15,444 nt) 2 aa deleted vaccine

<400> SEQUENCE: 4

```
atgacgtata ggtgttggct ctatgccacg gcatttgtat tgtcaggagc tgtgaccatt    60
ggcacagccc aaaacttgct gcacggaaaa cgcccttctg tgacagcctt cttcagggga   120
gcttaggggt ctgtccctag caccttgctt ctggagttgc actgctttac ggtctctcca   180 ccccttttaac catgtctggg atacttgatc ggtgcacgtg caccccccaat gccagggtgt   240 ttatggcgga gggccaagtc tactgcacac gatgtctcag tgcacggtct ctccttcctc   300
tgaatctcca agttcctgag cttggggtgc tgggcctatt ttataggccc gaagagccac   360
tccggtggac gttgccacgt gcattcccca ctgtcgagtc ctcccctgcc ggggcctgct   420
ggctttctgc gatctttcca attgcacgaa tgaccagtgg aaacctgaac tttcaacaaa   480
gaatggtgcg ggttgcagct gagatttaca gagccggcca actcacccct gcagttttga   540
aggctctaca agtttatgaa cggggttgtc gctggtaccc cattgtcgga cctgtccctg   600
```

```
gagtggccgt ttacgccaac tccctacatg tgagtgacaa acctttcccg ggagcaactc    660
atgtgttaac caacctaccg ctcccgcaga ggcccaagcc tgaagacttt tgcccttttg    720
agtgtgctat ggctaacgtc tatgacattg ccataacgc cgtcatgtat gtggccagaa    780
ggaaagtctc ctgggcccct cgtggcgggg atgaagtgaa atttgaaacc gtccccgaag    840
agttgaagtt gattgcgaac cgactccaca tctccttccc gccccaccac gcagtggaca    900
tgtctgagtt tgccttcata gcccctggga gtggtgtctc cttgcgggtc gagcaccaac    960
acggctgcct tcccgctgat actgtccctg atgggaactg ctggtggtac ttgtttgact   1020
tgctcccacc ggaagttcag aataaagaaa ttcgccgtgc taaccaattt ggctatcaaa   1080
ccaagcatgg tgtccatggc aagtacctac agcggaggct gcaagttaat ggtctccgag   1140
cagtgactga tacagatgga cctattgtcg tacagtactt ctctgttagg gagagttgga   1200
tccgccactt cagactggcg gaagaaccta gcctccctgg gtttgaagac ctcctcagaa   1260
taagggtaga gcctaatacg tcgccaatgg gtggcaaggg tgaaaaaatc ttccggtttg   1320
gcagtcacaa gtggtacggt gctggaaaga gagcaaggag agcacgctct ggtgcgactg   1380
ccacggtcgc tcaccgcgct ttgcccgctc gcgaagccca gcaggccaag aagctcgagg   1440
ttgccagcgc caacagggct gagcatctca agtactattc cccgcctgcc gacgggaact   1500
gtggttggca ctgcatttcc gccattacca accggatggt gaattccaaa tttgaaacca   1560
ctcttcccga gagagtgaga ccttcagatg actgggctac tgacgaggat cttgtgaata   1620
ccatccaaat cctcaggctc cccgcggcct tggacaggaa cggtgcttgt gctggcgcca   1680
agtacgtgct caagctggaa ggtgagcact ggaccgtctc tgtgacccct gggatgaccc   1740
cttctttgct cccccttgaa tgtgttcagg ttgttgtga gcataagagc ggtcttggtt   1800
tcccagacgt ggtcgaagtt tccggatttg accctgcctg tcttgaccga cttgctgaga   1860
taatgcactt gcctagcagt gtcatcccag ctgctctggc cgagatgtcc gacgacttca   1920
atcgtctggc ttccccggcc gccactgtgt ggactgtttc gcaattcttt gcccgccaca   1980
gaggaggaga gcatcctgac caggtgtgct tagggaaaat tatcaacctt tgtcaggtga   2040
ttgaggaatg ctgctgttcc cggaacaaag ccaaccgggc tacccccgaa gaggttgcgg   2100
caaaagttga ccagtacctc cgtggtgcag caagccttgg agaatgcttg ccaagcttg    2160
agagggctcg cccgccgagc gcgacggaca cctcctttga ttggaatgtt gtgcttcctg   2220
gggttgagac ggcgaatcag acaaccaaac agctccatgt caaccagtgc cgcgctctgg   2280
ttcctgtcgt gactcaagag cctttggaca gagactcggt ccctctgacc gccttctcgc   2340
tgtccaattg ctactaccct gcacaaggtg acgaggtccg tcaccgtgag aggctaaact   2400
ccttgctctc taagttggag ggggttgttc gtgaggaata tgggctcacg ccaactggac   2460
ctggcccgcg accgcactg ccgaacgggc tcgacgagct taaagaccag atggaggagg    2520
atctgctgaa attagtcaac gcccaggcaa cttcagaaat gatggcctgg gcagccgagc   2580
aggttgatct aaaagcttgg gtcaaaaatt acccacggtg gacaccgcca cccctcccac   2640
caagagttca gcctcgaaaa acgaagtctg tcaagagctt gctagagaac aagcctgtcc   2700
ctgctccgcg caggaaggtc agatctgatt gtggcagccc gattttgatg ggcgacaatg   2760
ttcctaacgg ttgggaagat tcgactgttg gtggtcccct tgatctttcg gcaccatccg   2820
agccgatgac acctctgagt gagcctgtac ttatttccag gccagtgaca tctttgagtg   2880
tgccggccca agtcctgca ccgcgtagag ctgtgtcccg accgatgacg ccctcgagtg    2940
agccaatttt tgtgtctgca ctgcgacaca aatttcagca ggtggaaaaa gcaaatctgg   3000
```

```
cggcagcagc gccgatgtgc caggacgaac ccttagattt gtctgcatcc tcacagactg   3060
aatatgaggc ttccccccta acaccaccgc agaacgtggg cattctggag gtaagggggc   3120
aagaagctga ggaagttctg agtgaaatct cggatattct gaatgatacc aaccctgcac   3180
ctgtgtcatc aagcagctcc ctgtcaagtg ttaagatcac acgcccaaaa tactcagctc   3240
aagccattat cgactcgggc gggccctgca gtgggcacct ccaaagggaa aagaagcat   3300 gcctccgcat catgcgtgag gcttgtgatg cggccaagct tagtgaccct gccacgcagg   3360
aatggctttc tcgcatgtgg datagggtgg acatgctgac ttggcgcaac acgtctgctt   3420
accaggcgtt tcgcacctta gatggcaggt ttgggtttct cccaaagatg atactcgaga   3480
cgccgccgcc ctacccgtgt gggtttgtga tgttgcctca caccctgca ccttccgtga   3540 gtgcagagag cgaccttacc attggttcag tcgccactga agatattcca cgcgtcctcg   3600
ggaaaataga aaataccggt gagatgatca accagggacc cttggcatcc tctgaggaag   3660
aaccggtata caaccaacct gccaaagact cccggatatc gtcgcggggg tctgacgaga   3720
gcacagcagc cccgtccgcg ggtacaggtg cgccggctt atttactgat ttgccacctt   3780
cagacggcgt agatgcggac ggtgggggc cgttgcagac ggtaagaaag aaagctgaaa   3840
ggctcttcga ccaattgagc cgtcaggttt ttaacctcgt ctcccatctc cctgttttct   3900
tctcacacct cttcaaatct gacagtggtt attctccggg tgattggggt tttgcagctt   3960
ttactctatt ttgcctcttt ttgtgttaca gctacccatt cttcggtttc gttccctct   4020 tgggtgtatt ttctgggtct tctcggcgtg tgcgcatggg ggtttttggc tgctggctgg   4080
cttttgctgt tggcctgttc aagcctgtgt ccgacccagt cggcactgct tgtgagtttg   4140
actcgccaga gtgcaggaac gtccttcatt cttttgagct tctcaaacct tgggaccctg   4200
ttcgcagcct tgttgtgggc cccgtcggtc tcggtcttgc cattcttggc aggttactgg   4260
gcggggcacg ctacatctgg catttttgc ttaggcttgg cattgttgca gattgtatct   4320
tggctggagc ttatgtgctt tctcaaggta ggtgtaaaaa gtgctgggga tcttgtataa   4380
gaactgctcc taatgaaatc gccttcaacg tgttcccttt tacacgtgcg accaggtcgt   4440
cactcatcga cctgtgcgat cggttttgtg cgccaacagg catggacccc attttcctcg   4500
ccactgggtg gcgtgggtgc tggaccggcc gaagtcccat tgagcaaccc tctgaaaaac   4560
ccatcgcgtt cgcccagttg gatgaaaaga ggattacggc tagaactgtg gtcgctcagc   4620
cttatgatcc taatcaagcc gtgaagtgct tgcgggtgtt acaggcgggt ggggcgatgg   4680 tggccgagc agtcccaaaa gtggccaaag tttctgctat tccattccga gccccttttt   4740
ttcccaccgg agtgaaagtt gatcccgagt gcaggatcgt ggttgacccc gatactttta   4800
ctacagccct ccgtctggt tactctacca caaacctcgt ccttggtgtg gggactttg   4860 cccagctgaa tggactaaag atcaggcaaa tttccaagcc ttcgggagga ggcccacacc   4920
tcattgctgc cctgcatgtt gcctgctcga tggcgttgca catgcttgct ggggtttatg   4980
taacttcagt ggggtcttgc ggtgccggca ccaacgatcc atggtgcact aatccgtttg   5040
ccgttcctgg ctacggacca ggctctctct gcacgtccag attgtgcatc tcccaacatg   5100 gccttacct gcccttgaca gcacttgtgg cgggattcgg tcttcaggaa atcgccttgg   5160 tcgtttttgat tttcgtttcc atcggaggca tggctcatag gttgagttgt aaggctgata   5220
tgctgtgcat tttacttgca atcgccagct atgtttgggt acccttacc tggttgcttt   5280 gtgtgtttcc ttgttggttg cgctggttct ctttgcaccc ccttaccatc ctatggttgg   5340
```

```
tgttttctt  gatttctgta  aatatgcctt  cgggaatctt  ggccgtggtg  ttattggttt    5400
ctctttggct  tttgggacgt  tatactaaca  ttgctggtct  tgtcacccc   tatgatattc    5460 atcattacac  cagtggcccc  cgcggtgttg  ccgccttggc  taccgcacca  gatggaacct    5520
acttggctgc  cgtccgccgc  gctgcgttga  ctggtcgcac  catgctgttc  accccgtctc    5580
agcttgggtc  ccttcttgag  ggcgctttca  gaactcgaaa  gccctcactg  aacaccgtca    5640
atgtggttgg  gtcctccatg  ggctctggtg  gagtgttcac  catcgacggg  aaaattaggt    5700
gcgtgactgc  cgcacatgtc  cttacgagta  attcggctag  ggtttccgga  gtcggcttca    5760
atcaaatgct  tgactttgat  gtgaaagggg  acttcgccat  agctgattgc  ccgaattggc    5820
aaggagctgc  tcccaagacc  caattctgcg  aggacggatg  gactggccgt  gcctattggc    5880
tgacatcctc  tggcgtcgaa  cccgtgtta   ttgggaatgg  attcgccttc  tgcttcaccg    5940
cgtgcggcga  ttccgggtcc  ccagtgatca  ccgaagctgg  tgagattgtc  ggcgttcaca    6000
caggatcaaa  taaacaagga  ggtggcatcg  tcacgcgccc  ttcaggccag  ttttgtaacg    6060
tggcacccat  caagctgagc  gaattaagtg  aattctttgc  tggacccaag  gtcccgctcg    6120
gtgatgtgaa  ggttggcagc  cacataatta  agacacgtg   cgaagtacct  tcagatcttt    6180
gcgccttgct  tgctgccaaa  cctgaactgg  agggaggcct  ctccaccgtc  caacttctgt    6240
gtgtgttttt  cctactgtgg  agaatgatgg  gacatgcctg  gacgcccttg  gttgctgtgg    6300 ggttttcat   tctgaatgag  gttctcccag  ctgtcctggt  tcggagtgtt  ttctcctttg    6360
ggatgtttgt  gctatcttgg  ctcacaccat  ggtctgcgca  agttctgatg  atcaggcttc    6420
taacagcagc  tcttaacagg  aacagatggt  cacttgcctt  ttacagcctt  ggtgcggtga    6480
ccggttttgt  cgcagatctt  gcggtaactc  aagggcaccc  gttgcaggca  gtgatgaatt    6540
tgagcaccta  tgccttcctg  cctcggatga  tggttgtgac  ctcaccagtc  ccagtgattg    6600
cgtgtggtgt  tgtgcaccta  cttgccatca  ttttgtactt  gttcaagtac  cgcggcctgc    6660
acaatgttct  tgttggtgat  ggagcgtttt  ctgcagcttt  cttcttgcga  tactttgccg    6720
agggaaagtt  gagggaaggg  gtgtcgcaat  cctgcggaat  gaatcatgag  tcattaactg    6780
gtgccctcgc  tatgggactc  aatgacgagg  acttggactt  ccttacgaaa  tggactgatt    6840
ttaagtgctt  tgtttctgcg  tccaacatga  ggaatgcagc  aggccaattc  atcgaggctg    6900
cctatgcaaa  agcacttaga  attgaacttg  cccagttggt  gcaggttgat  aaggttcgag    6960
gtactttggc  caagcttgag  gcttttgctg  ataccgtggc  accccaactc  tcgcccggtg    7020
acattgttgt  tgctcttggc  cacacgcctg  ttggcagcat  cttcgaccta  aaggttggtg    7080
gtaccaagca  tactctccaa  gtcattgaga  ccagagtcct  tgccgggtcc  aaaatgaccg    7140
tggcgcgcgt  cgttgaccca  accccacgc   ccccacccgc  accgtgccc   atccccctcc    7200 caccgaaagt  tctagagaat  ggtcccaacg  cctgggggga  tggggaccgt  ttgaataaga    7260
agaagaggcg  taggatggaa  accgtcggca  tctttgtcat  gggtgggaag  aagtaccaga    7320
aattttggga  caagaattcc  ggtgatgtgt  tttacgagga  ggtccatgac  aacacagatg    7380
cgtgggagtg  cctcagagtt  ggtgaccctg  ccgactttaa  ccctgagaag  ggaactctgt    7440
gtgggcatac  tactattgaa  gataaggatt  acaaagtcta  cgcctcccca  tctggcaaga    7500
agttcctggt  ccccgtcaac  ccagagagcg  aagagccca   atgggaagct  gcaaagcttt    7560
ccgtggagca  ggcccttggc  atgatgaatg  tcgacggtga  actgacggcc  aaagaagtgg    7620
agaaactgaa  aagaataatt  gacaaacttc  agggcctgac  taaggagcag  tgtttaaact    7680
gctagccgcc  agcggcttga  cccgctgtgg  tcgcggcggc  ttggttgtta  ctgagacagc    7740
```

```
ggtaaaaata gtcaaatttc acaaccggac tttcacccta gggcctgtga atttaaaagt    7800
ggccagtgag gttgagctga aagacgcggt cgagcacaac caacacccgg ttgcaagacc    7860
ggttgacggt ggtgttgtgc tcctgcgttc cgcagttcct tcgcttatag atgtcctgat    7920
ctccggtgct gacgcatctc ctaagttact cgctcgtcac gggccgggga acactgggat    7980
cgatggcacg ctttgggact ttgaggccga ggccaccaaa gaggaaattg cgctcagtgc    8040
gcaaataata caggcttgtg acattaggcg cggtgacgca cctgaaattg gtctccctta    8100
caagctgtac cctgttaggg gcaaccctga gcgggtaaaa ggagttttac agaatacaag    8160
gtttggagac ataccttaca aaaccccccag tgacactggg agcccagtgc acgcggctgc    8220
ctgcctcacg cccaatgcca ctccggtgac tgatgggcgc tccgtcttgg ctactaccat    8280
gccctccggt tttgaattgt atgtaccgac cattccagcg tctgtccttg attatcttga    8340
ctctaggcct gactgcccca aacagttgac agagcacggc tgtgaggatg ccgcattgag    8400
agacctctcc aagtatgact tgtccaccca aggctttgtt ttacctgggg ttcttcgcct    8460
tgtgcgtaag tacctgtttg cccacgtggg taagtgcccg cccgttcatc ggccttccac    8520
ttaccctgcc aagaattcta tggctggaat aaatgggaac aggtttccaa ccaaggacat    8580
tcagagcgtc cccgaaatcg acgttctgtg cgcacaggcc gtgcgagaaa actggcaaac    8640
tgttacccct tgtaccctca agaaacagta ttgtgggaag aagaagacta ggacaatact    8700
cggcaccaat aatttcattg cgttggccca ccgggcagcg ttgagtggtg tcacccaggg    8760
cttcatgaaa aaggcgtttta actcgcccat cgccctcggg aaaaacaaat ttaaggagct    8820
acagactccg atcttaggca ggtgccttga agctgatctt gcatcctgtg atcgatccac    8880
acctgcaatt gtccgctggt ttgccgccaa ccttctttat gaacttgcct gtgctgaaga    8940
gcacctaccg tcgtacgtgc tgaactgctg ccatgaccta ttggtcacgc agtccggcgc    9000
agtgactaag aggggtggcc tgtcgtctgg cgacccgatc acttctgtgt ctaacaccat    9060
ttacagcttg gtgatatatg cacagcacat ggtgcttagt tactttaaaa gtggtcaccc    9120
tcatggcctt ctgttcctac aagaccagct gaagttcgag gacatgctca agtccaacc    9180 cctgatcgtc tattcggacg acctcgtgct gtatgccgaa tctcccacca tgccgaacta    9240
ccactggtgg gtcgaacatc tgaatttgat gctgggtttt cagacggacc caaagaagac    9300
agccataacg gactcgccat catttctagg ctgtaggata taaatggac gccagctagt    9360 ccccaaccgt gacaggatcc tcgcggccct cgcttaccat atgaaggcaa gcaatgtttc    9420
tgaatactac gccgcggcgg ctgcaatact catggacagc tgtgcttgtt tagagtatga    9480
tcctgaatgg tttgaagagc ttgtggttgg gatagcgcag tgcgcccgca aggacggcta    9540
cagctttccc ggcccgccgt tcttcttgtc catgtgggaa aaactcagat ccaatcatga    9600
ggggaagaag tccagaatgt gcgggtattg cggggccccg ctccgtacg ccactgcctg    9660 tggcctcgac gtctgtattt accacaccca cttccaccag cattgtccag tcacaatctg    9720
gtgtggccac ccggctggtt ctggttcttg tagtgagtgc aaacccccc tagggaaagg    9780 cacaagccct ctagatgagg tgttagaaca agtcccgtat aagcctccac ggactgtaat    9840
catgcatgtg gagcagggtc tcacccctct tgacccagga agataccaga ctcgcgcgg    9900 attagtctcc gttaggcgtg gcatcagagg aaatgaagtt gacctaccag acggtgatta    9960
tgctagcacc gccctactcc ccacttgtaa agagatcaac atggtcgctg tcgcctctaa   10020
tgtgttgcgc agcaggttca tcatcggtcc gcccggtgct gggaaaacat actggctcct   10080
```

```
tcagcaggtc caggatggtg atgtcattta cacaccgact caccagacca tgctcgacat   10140
gattagggct tgggacgt gccggttcaa cgtcccagca ggtacaacgc tgcaattccc    10200 tgcccctcc cgtaccggcc cgtgggttcg catcctagcc ggcggttggt gtcctggtaa    10260
gaattccttc ctgatgaag cagcgtattg taatcacctt gatgtcttga ggctccttag    10320
caaaaccacc ctcacctgtc tgggagactt caaacaactc cacccagtgg ttttgattc    10380 tcattgctat gttttgaca tcatgcctca gacccagttg aagaccatct ggagattcgg    10440
acagaacatc tgtgatgcca tccaaccaga ttacagggac aaacttgtgt ccatggtcaa    10500
cacaacccgt gtaacctacg tggaaaaacc tgtcaagtat gggcaagtcc tcaccccta    10560 ccacagggac cgagaggacg gcgccatcac aattgactcc agtcaaggcg ccacatttga    10620
tgtggtcaca ctgcatttgc ccactaaaga ttcactcaac aggcaaagag cccttgttgc    10680
tatcaccagg gcaagacatg ctatctttgt gtatgaccca cacaggcaat tgcagagcat    10740
gtttgatctt cctgcgaagg gcacaccccgt caacctcgca gtgcaccgtg atgagcagct    10800
gatcgtactg gatagaaata taaagaatg cacagttgct caggctctag caacggaga    10860 taaatttagg gccaccgaca agcgcgttgt agattctctc cgcgccattt gtgctgatct    10920
ggaagggtcg agctctccgc tccccaaggt cgcacacaac ttgggatttt atttctcacc    10980
tgatttgaca cagtttgcta aactcccggt agaccttgca ccccactggc ccgtggtgac    11040
aacccagaac aatgaaaagt ggccggatcg gctggttgcc agccttcgcc ctgtccataa    11100
gtatagccgt gcgtgcattg gtgccggcta tatggtgggc ccctcggtgt ttctaggcac    11160 ccctgggtc gtgtcatact acctcacaaa atttgtcaag gcgaggctc aagtgcttcc    11220 ggagacagtc ttcagcaccg gccgaattga ggtggattgc cgggagtatc ttgatgacag    11280
ggagcgagaa gttgctgagt ccctcccaca tgccttcatt ggcgacgtca aaggcaccac    11340
cgttggggga tgtcatcatg tcacctccaa ataccttccg cgcttccttc caaggaatc    11400 agtcgcggta gtcggggttt cgagccccgg gaaagccgca aaagcagtgt gcacattgac    11460
ggatgtgtac ctcccagacc ttgaggccta cctccaccca gagactcagt ccaagtgctg    11520
gaaagttatg ttggacttca aggaagttcg actgatggtc tggaaagaca agacggccta    11580
tttccaactt gaaggccgct atttcacctg gtatcagctt gcaagctacg cctcgtacat    11640
ccgtgttcct gtcaactcca cggtgtatct ggacccctgc atgggccctg ccctttgcaa    11700
cagaagagtt gtcgggtcca cccattgggg agctgacctc gcagtcaccc cttatgatta    11760
cggtgctaaa atcatcttgt ctagcgctta ccatggtgaa atgcctcctg gatacaagat    11820
tctggcgtgc gcggagttct cgctcgacga cccagtcaag tacaaacaca cctggggttt    11880
tgaatcggat acagcgtatc tgtatagagtt caccggaaac ggtgaggact gggaggatta    11940
caatgatgcg tttcgtgcgc gccagaaagg gaaaatttat aaggccactg ctaccagcat    12000
gaagttttat tttcccccgg gccccgtcat tgaaccaact ttaggcctga attgaaatga    12060 aatgggtct atacaaagcc tcttcgacaa aattggccag cttttgtgg atgctttcac    12120 ggaattttg gtgtccattg ttgatatcat catatttttg gccattttgt ttggcttcac    12180
catcgccggt tggctggtgg tcttttgcat cagattggtt tgctccgcgg tattccgtgc    12240
gcgccctgcc attcaccctg agcaattaca gaagatccta tgaggccttt ctttctcagt    12300
gccgggtgga cattcccacc tgggggtaa aacacccttt ggggatgttt tggcaccata    12360
aggtgtcaac cctgattgat gaatggtgt cgcgtcgaat gtaccgcatc atggaaaaag    12420
cagggcaagc tgcctggaaa caggtggtga gcgaggctac gctgtctcgc attagtagtt    12480
```

```
tggatgtggt ggctcatttt caacatcttg ccgccattga agccgagacc tgtaaatatt   12540
tggcttctcg actgcccatg ctacacaacc tgcgcatgac agggtcaaat gtaaccatag   12600
tgtataatag cactttaaat caggtgtttg ctattttttcc aaccctggt tcccggccaa    12660 agcttcatga ttttcagcaa tggctaatag ctgtacattc ctccatattt tcctctgttg   12720
cagcttcttg tactcttttt gttgtgctgt ggttgcgggt tccaatgcta cgtactgttt   12780
ttggtttccg ctggttaggg gcaattttttc tttcgaactc atggtgaatt acacggtgtg   12840
tccaccttgc ctcacccgac aagcagccgc tgaggtcctt gaacccggta ggtctctttg   12900
gtgcaggata gggcatgacc gatgtgggga ggacgatcac gacgaactgg ggttcatggt   12960
tccgcctggc ctctccagcg aaagccactt gaccagtgtt tacgcctggt tggcgttcct   13020
gtccttcagc tacacggccc agttccatcc cgagatattt gggataggga acgtgagtga   13080
agtttatgtt gacatcaagc accaattcat ctgcgccgtt catgacgggc agaacaccac   13140
cttgcctcgc catgacaata tttcagccgt atttcagacc tactatcaac atcaggtcga   13200
cggcggcaat tggtttcacc tagaatggct gcgtcccttc ttttcctctt ggttggtttt   13260
aaatgtttcg tggtttctca ggcgttcgcc tgcaagccat gtttcagttc gagtctttca   13320
gacatcaaaa ccaacactac cgcagcatca ggctttgttg tcctccagga catcagctgc   13380
cttaggcatg gcgactcgtc cttttccgacg attcgcaaaa gctctcaatg ccgcacggcg   13440
atagggacac ctgtgtatat caccatcaca gccaatgtga cagatgagaa ttacttacat   13500
tcttctgatc tcctcatgct ttcttcttgc cttttctatg cttctgagat gagtgaaaag   13560
ggattcaagg tggtatttgg caatgtgtca ggcatcgtgg ctgtgtgtgt caactttacc   13620
agctacgtcc aacatgtcaa agagtttacc caacgctcct tggtggtcga tcatgtgcgg   13680
ctgcttcatt tcatgacacc tgagaccatg aggtgggcaa ccgttttagc ctgtctttttt   13740 gccatcctac tggcaatttg aatgttcaag tatgttgggg aaatgcttga ccgcgggctg   13800
ttgctcgcga ttgctttctt tgtggtgtat cgtgccgttc tggtttgctg tgctcggcaa   13860
cgccaacagc agcagcagct ctcattttca gttgatttat aacttgacgc tatgtgagct   13920
gaatggcaca gattggctgg caggaaaatt tgattgggca gtggagactt ttgtcatctt   13980
tcccgtgttg actcacattg tttcctatgg tgcactcacc accagccatt tccttgacac   14040
agttggtctg gttactgtgt ccaccgccgg gttttatcac gggcggtatg tcttgagtag   14100
catctacgcg gtctgtgctc tggctgcgtt gatttgcttc gttattaggc ttgcgaagaa   14160
ctgcatgtcc tggcgctact cttgtaccag atataccaac ttccttctgg acactaaggg   14220
cagactctat cgttggcggt cgcccgttat catagaaaaa gggggtaagg ttgaggtcga   14280
aggtcatctg atcgacctca aaagagttgt gcttgatggt tccgtggcaa cccctttaac   14340
cagagtttca gcggaacaat ggggtcgtct ctagacgact tttgccatga tagcacggct   14400
ccacaaaagg tgcttttggc gttttccatt acctacacgc cagtaatgat atatgctcta   14460
aaggtaagtc gcggccgact gctagggctt ctgcacccttt tgatctttct gaattgtgct   14520
tttaccttcg ggtacatgac attcgcgcac tttcagagca caaatagggt cgcgctcgct   14580
atgggagcag tagttgcact tctttggggg gtgtactcag ccatagaaac ctggaaattc   14640
atcacctcca gatgccgttt gtgcttgcta ggccgcaagt acattctggc ccctgcccac   14700
cacgtcgaaa gtgccgcggg ctttcatccg attgcggcaa atgataacca cgcatttgtc   14760
gtccggcgtc ccggctccat tacggttaac ggcacattgg tgcccgggtt gaaaagcctc   14820
```

| | |
|---|---|
| gtgttgggtg cagaaaagc tgttaaacgg ggagtggtaa accttgtcaa atatgccaaa | 14880 |
| taacaacggc aagcagcaaa agaaaaagaa ggggaatggc cagccagtca accagctgtg | 14940 |
| ccagatgctg ggtaaaatca tcgcccagca aaaccagtcc agaggcaagg gaccgggctc | 15000 |
| taagaagaaa tccccggaga agccccattt tcctctagcg accgaagatg acgtcaggca | 15060 |
| tcacttcacc cctggtgagc ggcaattgtg tctgtcgtcg atccagactg cctttaacca | 15120 |
| gggcgctgga acttgtaccc tgtcagattc agggaggata agttacactg tggagtttag | 15180 |
| tttgccgacg catcatactg tgcgcctgat ccgcgtcaca gcatcaccct cagcatgatg | 15240 |
| ggctggcatt ctttaggcac ctcagtgtca gaattggaag aatgtgtggt ggatggcact | 15300 |
| gattgacatt gtgcctctaa gtcacctatt caattagggc gaccgtgtgg gggtaaaatt | 15360 |
| taattggcga gaaccatgcg gccgcaatta aaaaaaaaaa aaaaaaaaaa aaaaaaaaa | 15420 |
| aaaaaaaaaa aaaaaaaaaa aaaa | 15444 |

<210> SEQ ID NO 5
<211> LENGTH: 15450
<212> TYPE: DNA
<213> ORGANISM: Artificial Sequence
<220> FEATURE:
<223> OTHER INFORMATION: P129 passage 0 complete genome (15,450 nt) full length parental virus

<400> SEQUENCE: 5

| | |
|---|---|
| atgacgtata ggtgttggct ctatgccacg gcatttgtat tgtcaggagc tgtgaccatt | 60 |
| ggcacagccc aaaacttgct gcacggaaaa cgcccttctg tgacagcctt cttcagggga | 120 |
| gcttagggt ctgtccctag caccttgctt ctggagttgc actgctttac ggtctctcca | 180 |
| cccctttaac catgtctggg atacttgatc ggtgcacgtg cacccccaat gccagggtgt | 240 |
| ttatggcgga gggccaagtc tactgcacac gatgtctcag tgcacggtct ctccttcctc | 300 |
| tgaatctcca agttcctgag cttggggtgc tgggcctatt ttataggccc gaagagccac | 360 |
| tccggtggac gttgccacgt gcattcccca ctgtcgagtg ctcccccgcc ggggcctgct | 420 |
| ggctttctgc gatctttcca attgcacgaa tgaccagtgg aaacctgaac tttcaacaaa | 480 |
| gaatggtgcg ggttgcagct gagatttaca gagccggcca actcaccccct gcagttttga | 540 |
| aggctctaca agtttatgaa cggggttgtc gctggtaccc cattgtcgga cctgtccctg | 600 |
| gagtggccgt tcacgccaac tccctacatg tgagtgacaa acctttcccg ggagcaactc | 660 |
| atgtgttaac caacctaccg ctcccgcaga ggcccaagcc tgaagacttt gcccttttg | 720 |
| agtgtgctat ggctgacgtc tatgacatta gccatgacgc cgtcatgtat gtggccagag | 780 |
| ggaaagtctc ctgggcccct cgtggcgggg atgaagtgaa atttgaaacc gtccccgaag | 840 |
| agttgaagtt gattgcgaac cgactccaca tctccttccc gccccaccac gcagtggaca | 900 |
| tgtctgagtt tgccttcata gcccctggga gtggtgtctc cttgcgggtc gagcaccaac | 960 |
| acggctgcct tccgctgat actgtccctg aagggaactg ctggtggtgc ttgtttgact | 1020 |
| tgctcccacc ggaagttcag aataaagaaa ttcgccgtgc taaccaattt ggctatcaaa | 1080 |
| ccaagcatgg tgtccctggc aagtacctac agcggaggct gcaagttaat ggtctccgag | 1140 |
| cagtgactga tacagatgga cctattgtcg tacagtactg tctctgttag agagttgga | 1200 |
| tccgccactt cagactggcg gaagaaccta gcctccctgg gtttgaagac ctcctcagaa | 1260 |
| taagggtaga gcctaatacg tcgcattgg gtggcaaggg tgaaaaaatc ttccggtttg | 1320 |
| gcagtcacaa gtggtacggt gctggaaaga gagcaaggag agcacgctct ggtgcgactg | 1380 |

-continued

```
ccacggtcgc tcaccgcgct tgcccgctc gcgaagccca gcaggccaag aagctcgagg    1440
ttgccagcgc caacagggct gagcatctca agtactattc cccgcctgcc gacgggaact    1500
gtggttggca ctgcatttcc gccattacca accggatggt gaattccaaa tttgaaacca    1560
ctcttcccga gagagtgaga ccttcagatg actgggctac tgacgaggat cttgtgaatg    1620
ccatccaaat cctcaggctc cccgcggcct tggacaggaa cggtgcttgt gctggcgcca    1680
agtacgtgct caagctggaa ggtgagcact ggaccgtctc tgtgacccct gggatgaccc    1740
cttctttgct ccccccttgaa tgtgttcagg gttgttgtga gcatacgagc ggccttggtt    1800
tcccagatgt ggtcgaagtt tccggatttg accctgcctg ccttgaccga cttgctgaga    1860
taatgcactt gcctagcagt gtcatcccag ctgctctggc cgagatgtcc gacgacttca    1920
atcgtctggc ttccccggcc gccactgtgt ggactgtttc gcaattcttt gcccgccaca    1980
gaggaggaga gcatcctgac caggtgtgct tagggaaaat tatcaaccttt tgtcaggtga    2040 ttgaggaatg ctgctgttcc cggaacaaag ccaaccgggc tacccccgaa gaggttgcgg    2100
caaaaattga ccagtacctc cgtggtgcag caagccttgg agaatgcttg ccaagcttg    2160 agatggctcg cccgccgagc gcgatggaca cctcctttga ttggaatgtt gtgcttcctg    2220
gggttgagac ggcgaatcag acaaccaaac agctccatgt caaccagtgc cgcgctctgg    2280
ttcctgtcgt gactcaagag ccttttggaca gagactcagt ccctctgacc gccttctcgc    2340
tgtccaattg ctactaccct gcacaaggtg acgaggtccg tcaccgtgag aggctaaact    2400
ccgtgctctc taagttggag ggggttgttc gtgaggaata tgggctcacg ccaactggac    2460
ctggcccgcg acccgcactg ccgaacgggc tcgacgagct taaagaccag atggaggagg    2520
atctgctgaa attagtcaac gcccaggcaa cttcagaaat gatggcctgg gcagccgagc    2580
aggttgatct gaaagcttgg gtcaaaaatt acccacggtg gacaccgcca cccccctccac    2640 caagagttca gcctcgaaaa acgaagtctg tcaagagctt gctagagaac aagcctgtcc    2700
ctgctccgcg caggaaggtc agatctgatt gtggcagccc gattttgatg ggcgacaatg    2760
ttcctaacgg ttgggaagat tcgactgttg gtggtcccct tgacctttcg gcaccatccg    2820
agccgatgac acctctgagt gagcctgtac ttatttccag gccagtgaca tctttgagtg    2880
tgccggcccc agttcctgca ccgcgtagag ctgtgtcccg accgatgacg ccctcgagtg    2940
agccaatttt tgtgtctgca ctgcgacaca aatttcagca ggtggaaaaa gcaaatctgg    3000
cggcagcagc gccgatgtac caggacgaac ccttagattt gtctgcatcc tcacagactg    3060
aatatgagcc ttctcccccta acaccaccgc agaacgtggg cattctggag gtaaggggc    3120 aagaagctga ggaagttctg agtgaaatct cggatattct gaatgacacc aaccctgcac    3180
ctgtgtcatc aagcagctcc ctgtcaagtg ttaggatcac acgcccaaaa tactcagctc    3240
aagccattat cgactcgggc gggccctgca gtgggcacct ccaaagggaa aagaagcat    3300 gcctccgcat catgcgtgag gcttgtgatg cggccaagct tagtgaccct gccacgcagg    3360
aatggctttc tcgcatgtgg gatagggtgg acatgctgac ttggcgcaac acgtctgctt    3420
accaggcgtt tcgcacctta gatggcaggt ttgggtttct cccaaagatg atactcgaga    3480
cgccgccgcc ctaccgtgt gggttttgtga tgttgcctca cacccctgca ccttccgtga    3540
gtgcagagag cgaccttacc atcggttcag tcgccactga agatattcca cgcatcctcg    3600
ggaaaataga aaataccggt gagatgatca accagggacc cttggcatcc tctgaggaag    3660
aaccggtata caaccaacct gccaaagact cccggatatc gtcgcggggg tctgacgaga    3720
gcacagcagc tccgtccgca ggtacaggtg gcgccggctt atttactgat ttgccacctt    3780
```

```
cagacggcgt agatgcggac ggtgggggc cgttgcagac ggtaagaaag aaagctgaaa    3840
ggctcttcga ccaattgagc cgtcaggttt ttaacctcgt ctcccatctc cctgttttct    3900
tctcacacct cttcaaatct gacagtggtt attctccggg tgattggggt tttgcagctt    3960
ttactctatt ttgcctcttt ttgtgttaca gctacccatt cttcggtttc gttccctct    4020
tgggtgtatt ttctgggtct tctcggcgtg tgcgcatggg ggttttggc tgctggctgg    4080
cttttgctgt tggcctgttc aagcctgtgt ccgacccagt cggcactgct tgtgagtttg    4140
actcgccaga gtgtaggaac gtccttcatt cttttgagct tctcaaacct gggaccctg    4200
ttcgcagcct tgttgtgggc cccgtcggtc tcggtcttgc cattcttggc aggttactgg    4260
gcggggcacg ctacatctgg catttttgc ttaggcttgg cattgttgca gattgtatct    4320
tggctggagc ttatgtgctt tctcaaggta ggtgtaaaaa gtgctgggga tcttgtataa    4380
gaactgctcc taatgaaatc gccttcaacg tgttcccttt tacacgtgcg accaggtcgt    4440
cactcatcga cctgtgcgat cggttttgtg cgccaaaagg catggacccc attttcctcg    4500
ccactgggtg gcgtgggtgc tggaccggcc gaagtcccat tgagcaaccc tctgaaaaac    4560
ccatcgcgtt cgcccagttg gatgaaaaga ggattacggc tagaactgtg gtcgctcagc    4620
cttatgatcc taatcaagcc gtaaagtgct tgcgggtgtt acaggcgggt ggggcgatgg    4680
tggccgaggc agtcccaaaa gtggtcaaag tttctgctat tccattccga gccccctttt    4740
ttcccaccgg agtgaaagtt gatcccgagt gcaggatcgt ggttgacccc gatacttta    4800
ctacagccct ccggtctggt tactctacca caaacctcgt ccttggtgtg ggggactttg    4860
cccagctgaa tggactaaag atcaggcaaa tttccaagcc ttcggagga ggcccacacc    4920
tcattgctgc cctgcatgtt gcctgctcga tggcgttgca catgcttgct ggggtttatg    4980
taacttcagt ggggtcttgc ggtgccggca ccaacgatcc atggtgcact aatccgtttg    5040
ccgttcctgg ctacggacca ggctctctct gcacgtccag attgtgcatc tcccaacatg    5100
gccttaccct gcccttgaca gcacttgtgg cgggattcgg tcttcaggaa atcgccttgg    5160
tcgttttgat tttcgtttcc atcggaggca tggctcatag gttgagttgt aaggctgata    5220
tgctgtgcat cttacttgca atcgccagct atgtttgggt accccttacc tggttgcttt    5280
gtgtgttttcc ttgttggttg cgctggttct ctttgcaccc cctcaccatc ctatggttgg    5340
tgttttctt gatttctgta aatatgcctt cgggaatctt ggccgtggtg ttgttggttt    5400
ctctttggct tttgggacgt tatactaaca ttgctggtct tgtcaccccc tatgatattc    5460
atcattacac cagtggcccc cgcggtgttg ccgccttagc taccgcacca gatggaacct    5520
acttggctgc cgtccgccgc gctgcgttga ctggtcgcac catgctgttc accccgtctc    5580
agcttgggtc ccttcttgag ggcgctttca gaactcgaaa gccctcactg aacaccgtca    5640
atgtggttgg gtcctccatg ggctctggtg gagtgttcac catcgacggg aaaattaggt    5700
gcgtgactgc cgcacatgtc cttacgggta attcggctag ggtttccgga gtcggcttca    5760
atcaaatgct tgactttgat gtgaaagggg acttcgccat agctgattgc ccgaattggc    5820
aaggagctgc tcccaagacc caattctgcg cggatggatg gactggccgt gcctattggc    5880
tgacatcctc tggcgtcgaa cccggtgtca ttgggagtgg attcgccttc tgcttcaccg    5940
cgtgcggcga ttccgggtcc ccagtgatca ccgaagctgg tgagcttgtc ggcgttcaca    6000
caggatcaaa taacaagga ggtggcatcg tcacgcgccc ttcaggccag ttttgtaacg    6060
tggcacccat caagctgagc gaattaagtg aattctttgc tggacccaag gtcccgctcg    6120
```

```
gtgatgtgaa ggttggcagc cacataatta aagacacgtg cgaagtacct tcagatcttt    6180
gcgccttgct tgctgccaaa cctgaactgg agggaggcct ctccaccgtc caacttctgt    6240
gtgtgttttt cctactgtgg agaatgatgg gacatgcctg gacgcccttg gttgctgtgg    6300 ggttttcat tctgaatgag gttctcccag ctgtcctggt tcggagtgtt ttctcctttg    6360
ggatgtttgt gctatcttgg ctcacaccat ggtctgcgca agttctgatg atcaggcttc    6420
taacagcagc tcttaacagg aacagatggt cacttgcctt ttacagcctt ggtgcggtga    6480
ccggttttgt cgcagatctt gcggcaactc aagggcaccc gttgcaggca gtaatgaatt    6540
tgagcaccta tgccttcctg cctcggatga tggttgtgac ctcaccagtc ccagtgattg    6600
cgtgtggtgt tgtgcaccta cttgccatca ttttgtactt gtttaagtac cgtggcctgc    6660
acaatgttct tgttggtgat ggagcgtttt ctgcagcttt cttcttgcga tactttgccg    6720
agggaaagtt gagggaaggg gtgtcgcaat cctgcggaat gaatcatgag tcattgactg    6780
gtgccctcgc tatgagactc aatgacgagg acttggactt ccttacgaaa tggactgatt    6840
ttaagtgctt tgtttctgcg tccaacatga ggaatgcagc aggccaattc atcgaggctg    6900
cctatgcaaa agcacttaga attgaacttg cccagttggt gcaggttgat aaggttcgag    6960
gtactttggc caagcttgag gcttttgctg ataccgtggc accccaactc tcgcccggtg    7020
acattgttgt tgctcttggc catacgcctg ttggcagcat cttcgaccta aaggttggtg    7080
gtaccaagca tactctccaa gtcattgaga ccagagtcct tgccgggtcc aaaatgaccg    7140
tggcgcgcgt cgttgaccca accccccacgc ccccacccgc accgtgcccc atcccccctcc    7200 caccgaaagt tctagagaat ggtcccaacg cctgggggga tggggaccgt ttgaataaga    7260
agaagaggcg taggatggaa accgtcggca tctttgtcat gggtgggaag aagtaccaga    7320
aattttggga caagaattcc ggtgatgtgt tttacgagga ggtccatgac aacacagatg    7380
cgtgggagtg cctcagagtt ggtgaccctg ccgactttga ccctgagaag ggaactctgt    7440
gtgggcatac tactattgaa gataaggatt acaaagtcta cgcctcccca tctggcaaga    7500
agttcctggt ccccgtcaac ccagagagcg gaagagccca atgggaagct gcaaagcttt    7560
ccgtggagca ggcccttggc atgatgaatg tcgacggtga actgacggcc aaagaagtgg    7620
agaaactgaa aagaataatt gacaaacttc agggcctgac taaggagcag tgtttaaact    7680
gctagccgcc agcggcttga cccgctgtgg tcgcggcggc ttggttgtta ctgagacagc    7740
ggtaaaaata gtcaaatttc acaaccggac tttcacccta gggcctgtga atttaaaagt    7800
ggccagtgag gttgagctga aagacgcggt cgagcacaac caacacccgg ttgcaagacc    7860
ggttgacggt ggtgttgtgc tcctgcgttc cgcagttcct tcgcttatag atgtcctgat    7920
ctccggtgct gacgcatctc ctaagttact cgctcgtcac gggccgggga acactgggat    7980
cgatggcacg ctttgggact tgaggccga ggccaccaaa gaggaaattg cactcagtgc    8040
gcaaataata caggcttgtg acattaggcg cggcgacgca cctgaaattg gtctccctta    8100
caagctgtac cctgttaggg caaccctga gcgggtaaaa ggagttttac agaatacaag    8160
gtttggagac ataccttaca aaaccccccag tgacactgga agcccagtgc acgcggctgc    8220
ctgcctcacg cccaatgcca ctccggtgac tgatgggcgc tccgtcttgg ctactaccat    8280
gccctccggt tttgaattgt atgtaccgac cattccagcg tctgtccttg attatcttga    8340
ctctaggcct gactgcccca aacagttgac agagcacggc tgtgaggatg ccgcattgag    8400
agacctctcc aagtatgact tgtccaccca aggctttgtt ttacctgggg ttcttcgcct    8460
tgtgcgtaag tacctgtttg cccacgtggg taagtgcccg cccgttcatc ggccttccac    8520
```

```
ttaccctgcc aagaattcta tggctggaat aaatgggaac aggtttccaa ccaaggacat   8580
tcagagcgtc cctgaaatcg acgttctgtg cgcacaggcc gtgcgagaaa actggcaaac   8640
tgttacccct tgtaccctca agaaacagta ttgtgggaag aagaagacta ggacaatact   8700
cggcaccaat aatttcattg cgttggccca ccgggcagcg ttgagtggtg tcacccaggg   8760
cttcatgaaa aaggcgttta actcgcccat cgccctcggg aaaaacaaat ttaaggagct   8820
acagactccg gtcttaggca ggtgccttga agctgatctt gcatcctgtg atcgatccac   8880
acctgcaatt gtccgctggt ttgccgccaa tcttctttat gaacttgcct gtgctgaaga   8940
gcacctaccg tcgtacgtgc tgaactgctg ccatgaccta ttggtcacgc agtccggcgc   9000
agtgactaag aggggtggcc tgtcgtctgg cgacccgatc acttctgtgt ctaacaccat   9060
ttacagcttg gtgatatatg cacagcacat ggtgcttagt tactttaaaa gtggtcaccc   9120
tcatggcctt ctgttcctac aagaccagct gaagttcgaa gacatgctca agtccaacc    9180
cctgatcgtc tattcggacg acctcgtgct gtatgccgaa tctcccacca tgccgaacta   9240
ccactggtgg gtcgaacatc tgaatttgat gctgggtttt cagacggacc caaagaagac   9300
agccataacg gactcgccat catttctagg ctgtaggata taaatggac gccagctagt    9360
ccccaaccgt gacaggatcc tcgcggccct cgcttaccat atgaaggcaa gcaatgtttc   9420
tgaatactac gccgcggcgg ctgcaatact catggacagc tgtgcttgtt tagagtatga   9480
tcctgaatgg tttgaagagc ttgtggttgg gatagcgcag tgcgcccgca aggacggcta   9540
cagctttccc ggcccgccgt tcttcttatc catgtgggaa aaactcagat ccaatcatga   9600
ggggaagaag tccagaatgt gcgggtattg cggggccccg gctccgtacg ccactgcctg   9660
tggcctcgac gtctgtattt accacaccca cttccaccag cattgtccag tcataatctg   9720
gtgtggccac ccggctggtt ctggttcttg tagtgagtgc aaaccccccc tagggaaagg   9780
cacaagccct ctagatgagg tgttagaaca agtcccgtat aagcctccac ggactgtaat   9840
catgcatgtg gagcagggtc tcacccctct tgacccaggc agataccaga ctcgccgcgg   9900
attagtctcc gttaggcgtg gcatcagagg aaatgaagtt gacctaccag acggtgatta   9960
tgctagcacc gccctactcc ccacttgtaa agagatcaac atggtcgctg tcgcctctaa  10020
tgtgttgcgc agcaggttca tcatcggtcc gcccggtgct gggaaaacat actggctcct  10080
tcagcaggtc caggatggtg atgtcattta cacaccgact caccagacca tgctcgacat  10140
gattagggct ttggggacgt gccggttcaa cgtcccagca ggtacaacgc tgcaattccc  10200
tgcccctcc cgtaccggcc cgtgggttcg catcctagcc ggcggttggt gtcctggtaa   10260
gaattccttc ctggatgaag cagcgtattg taatcacctt gatgtcttga ggctccttag  10320
caaaaccacc ctcacctgtc tgggagactt caaacaactc cacccagtgg gttttgattc  10380
tcattgctat gtttttgaca tcatgcctca gacccagttg aagaccatct ggagattcgg  10440
acagaacatc tgtgatgcca tccaaccaga ttacagggac aaacttgtgt ccatggtcaa  10500
cacaacccgt gtaacctacg tggaaaaacc tgtcaagtat gggcaagtcc tcacccctta  10560
ccacagggac cgagaggacg gcgccatcac aattgactcc agtcaaggcg ccacatttga  10620
tgtggttaca ctgcatttgc ccactaaaga ttcactcaac aggcaaagag cccttgttgc  10680
tatcaccagg gcaagacatg ctatctttgt gtatgaccca cacaggcaat tgcagagcat  10740
gtttgatctt cctgcgaagg gcacacccgt caacctcgca gtgcaccgtg atgagcagct  10800
gatcgtactg gatagaaata taaagaatg cacagttgct caggctctag gcaacggaga   10860
```

```
taaatttagg gccaccgaca agcgcgttgt agattctctc cgcgccattt gtgctgatct   10920
ggaagggtcg agctctccgc tccccaaggt cgcacacaac ttgggatttt atttctcacc   10980
tgatttgaca cagtttgcta aactcccggt agaccttgca ccccactggc ccgtggtgac   11040
aacccagaac aatgaaaagt ggccggatcg gctggttgcc agccttcgcc ctgtccataa   11100
gtatagccgt gcgtgcattg gtgccggcta tatggtgggc ccctcggtgt ttctaggcac   11160
ccctggggtc gtgtcatact acctcacaaa atttgtcaag ggcgaggctc aagtgcttcc   11220
ggagacagtc ttcagcaccg gccgaattga ggtggattgc cgggggtatc ttgatgacag   11280
ggagcgagaa gttgctgagt ccctcccaca tgccttcatt ggcgacgtca aaggcaccac   11340
cgttggggga tgtcatcatg tcacctccaa ataccttccg cgcttccttc ccaaggaatc   11400
agtcgcggta gtcggggttt cgagcccccgg gaaagccgca aaagcagtgt gcacattgac   11460
ggatgtgtac ctcccagacc ttgaggccta cctccaccca gagactcagt ctaagtgctg   11520
gaaagttatg ttggacttca aggaagttcg actgatggtc tggaaagaca agacggccta   11580
tttccaactt gaaggccgct atttcacctg gtatcagctt gcaagctacg cctcgtacat   11640
ccgtgttcct gtcaactcca cggtgtatct ggacccctgc atgggccctg ccctttgcaa   11700
cagaagagtt gtcgggtcca cccattgggg agctgacctc gcagtcaccc cttatgatta   11760
cggtgctaaa atcatcttgt ctagcgctta ccatggtgaa atgcctcctg gatacaagat   11820
tctggcgtgc gcggagttct cgctcgacga cccagtcaag tacaaacaca cctgggggttt   11880 tgaatcggat acagcgtatc tgtatgagtt catcggaaac ggtgaggact gggaggatta   11940
caatgatgcg tttcgtgcgc gccagaaagg gaaaatttat aaggccactg ctaccagcat   12000
gaagttttat tttcccccgg gccccgtcat tgaaccaact ttaggcctga attgaaatga   12060 aatgggtct atacaaagcc tcttcgacaa aattggccag cttttttgtgg atgctttcac   12120 ggaattttttg gtgtccattg ttgatatcat catatttttg gccattttgt ttggcttcac   12180
catcgccggt tggctggtgg tcttttgcat cagattggtt tgctccgcgg tattccgtgc   12240
gcgccctgcc attcaccctg agcaattaca gaagatccta tgaggccttt ctttctcagt   12300
gccgggtgga cattcccacc tggggggtaa acaccccttt ggggatgttt tggcaccata   12360
aggtgtcaac cctgattgat gaaatggtgt cgcgtcgaat gtaccgcatc atggaaaaag   12420
cagggcaagc tgcctggaaa caggtggtga gcgaggctac gctgtctcgc attagtagtt   12480
tggatgaggt ggctcatttt caacatcttg ccgccattga agccgagacc tgtaaatatt   12540
tggcttctcg actgcccatg ctacacaacc tgcgcatgac agggtcaaat gtaaccatag   12600
tgtataatag cactttaaat caggtgtttg ctattttttcc aacccctggt tcccggccaa   12660
agcttcatga ttttcagcaa tggctaatag ctgtacattc ctccatattt tcctctgttg   12720
cagcttcttg tactcttttt gttgtgctgt ggttgcgggt tccaatgcta cgtactgttt   12780
ttggtttccg ctggttaggg gcaattttttc tttcgaactc atggtgaatt acacggtgtg   12840
tccaccttgc ctcacccgac aagcagccgc tgaggccctt gaacccggta ggtctctttg   12900
gtgcaggata gggcatgacc gatgtgggga ggacgatcac gacgaactag ggttcatggt   12960
tccgcctggc ctctccagcg aaagccactt gaccagtgtt tacgcctggt ggcgttcct   13020 gtccttcagc tacacggccc agttccatcc cgagatattt gggataggga acgtgagtga   13080
agtttatgtt gacatcaagc accaattcat ctgcgccgtt catgacgggc agaacaccac   13140
cttgcctcgc catgacaata tttcagccgt atttcagacc tactatcaac atcaggtcga   13200
cggcggcaat tggtttcacc tagaatggct gcgtcccttc ttttcctctt ggttggtttt   13260
```

```
aaatgtttcg tggtttctca ggcgttcgcc tgcaagccat gtttcagttc gagtctttca    13320
gacatcaaaa ccaacactac cgcagcatca ggctttgttg tcctccagga catcagctgc    13380
cttaggcatg gcgactcgtc ctttccgacg attcgcaaaa gctctcaatg ccgcacggcg    13440
atagggacac ctgtgtatat caccatcaca gccaatgtga cagatgagaa ttacttacat    13500
tcttctgatc tcctcatgct ttcttcttgc cttttctatg cttctgagat gagtgaaaag    13560
ggattcaagg tggtgtttgg caatgtgtca ggcatcgtgg ctgtgtgtgt caactttacc    13620
agctacgtcc aacatgtcaa agagtttacc caacgctcct tggtggtcga tcatgtgcgg    13680
ctgcttcatt tcatgacacc tgagaccatg aggtgggcaa ccgttttagc ctgtctttt    13740 gccatcctac tggcaatttg aatgttcaag tatgttgggg aaatgcttga ccgcgggctg    13800
ttgctcgcga ttgctttctt tgtggtgtat cgtgccgttc tggtttgctg tgctcgtcaa    13860
cgccaacaac accagcagct ctcatttca gttgatttat aacttgacgc tatgtgagct    13920
gaatggcaca gattgctggc agaaaaatt tgattgggca gtggagactt ttgtcatctt    13980
tcccgtgttg actcacattg tttcctatgg tgcactcacc accagccatt ccttgacac    14040 agttggtctg gttactgtgt ccaccgccgg gttttatcac gggcggtatg tcttgagtag    14100
cgtctacgcg gtctgtgctc tggctgcgtt gatttgcttc gtcattaggc ttgcgaagaa    14160
ctgcatgtcc tggcgctact cttgtaccag ataccaaac ttccttctgg acactaaggg    14220
cagactctat cgttggcggt cgcccgttat catagagaaa ggggtaagg ttgaggtcga    14280 aggtcacctg atcgacctca aaagagttgt gcttgatggt tccgtggcaa cccctttaac    14340
cagagtttca gcggaacaat ggggtcgtct ctagacgatt tttgccatga tagcacggct    14400
ccacaaaagg tgcttttggc gttttccatt acctacacgc cagtaatgat atatgctcta    14460
aaggtaagtc gcggccgact gctagggctt ctgcacctt tgatcttct gaattgtgct    14520 tttaccttcg ggtacatgac attcgtgcac tttcagagca caaatagggt cgcgctcact    14580
atgggagcag tagttgcact tctttggggg gtgtactcag ccatagaaac ctggaaattc    14640
atcacctcca gatgccgttt gtgcttgcta ggccgcaagt acattctggc ccctgcccac    14700
cacgtcgaaa gtgccgcggg ctttcatccg attgcggcaa atgataacca cgcatttgtc    14760
gtccggcgtc ccggctccac tacggttaac ggcacattgg tgcccgggtt gaaaagcctc    14820
gtgttgggtg gcagaaaagc tgttaaacag ggagtggtaa accttgtcaa atatgccaaa    14880
taacaacggc aagcagcaaa agaaaaagaa ggggaatggc cagccagtca atcagctgtg    14940
ccagatgctg ggtaaaatca tcgcccagca aagccagtcc agaggcaagg gaccgggcaa    15000
gaaaagtaag aagaaaaacc cggagaagcc ccatttcct ctagcgaccg aagatgacgt    15060
caggcatcac ttcacccctg tgagcggca attgtgtctg tcgtcgatcc agactgcctt    15120
taatcagggc gctggaactt gtaccctgtc agattcaggg aggataagtt acactgtgga    15180
gtttagtttg ccgacgcatc atactgtgcg cctgatccgc gtcacagcat cccctcagc    15240 atgatgggct ggcattcttt aggcacctca gtgtcagaat tggaagagtg tgtggtggat    15300
ggcactgatt gacattgtgc ctctaagtca cctattcaat tagggcgacc gtgtgggggt    15360
aaaatttaat tggcgagaac catgcggccg caattaaaaa aaaaaaaaa aaaaaaaaa    15420 aaaaaaaaa aaaaaaaaa aaaaaaaaa                                      15450

<210> SEQ ID NO 6
<211> LENGTH: 15450
<212> TYPE: DNA
```

<213> ORGANISM: Artificial Sequence
<220> FEATURE:
<223> OTHER INFORMATION: P129-PKC12-FL passage 52 complete genome
      (15,450 nt) full length vaccine virus

<400> SEQUENCE: 6

```
atgacgtata ggtgttggct ctatgccacg gcatttgtat tgtcaggagc tgtggccatt      60
ggcacagccc aaaacttgct gcacggaaaa cgcccttctg tgacagcctt cttcagggga     120
gcttaggggt ctgtccctag caccttgctt ctggagttgc actgctttac ggtctctcca     180
cccctttaac catgtctggg atacttgatc ggtgcacgtg cacccccaat gccagggtgt     240
ttatggcgga gggccaagtc tactgcacac gatgtctcag tgcacggtct ctccttcctc     300
tgaatctcca agttcctgag cttggggtgc tgggcctatt ttataggccc gaagagccac     360
tccggtggac gttgccacgt gcattcccca ctgtcgagtg ctcccctgcc ggggcctgct     420
ggctttctgc gatctttcca attgcacgaa tgaccagtgg aaacctgaac tttcaacaaa     480
gaatggtgcg ggttgcagct gagatttaca gagccggcca actcacccct gcagttttga     540
aggctctaca agtttatgaa cggggttgtc gctggtaccc cattgtcgga cctgtccctg     600
gagtggccgt ttacgccaac tccctacatg tgagtgacaa acctttcccg ggagcaactc     660
atgtgttaac caacctaccg ctcccgcaga ggcccaagcc tgaagacttt tgcccttttg     720
agtgtgctat ggctaacgtc tatgacattg ccataacgc cgtcatgtat gtggccagag     780
ggaaagtctc ctgggcccct cgtggcgggg atgaagtgaa atttgaaacc gtccccgaag     840
agttgaagtt gattgcgaac cgactccaca tctccttccc gccccaccac gcagtggaca     900
tgtctgagtt tgccttcata gcccctggga gtggtgtctc cttgcgggtc gagcaccaac     960
acggctgcct tcccgctgat actgtccctg atgggaactg ctggtggtac ttgtttgact    1020
tgctcccacc ggaagttcag aataaagaaa ttcgccgtgc taaccaattt ggctatcaaa    1080
ccaagcatgg tgtccatggc aagtacctac agcggaggct gcaagttaat ggtctccgag    1140
cagtgactga tacagatgga cctattgtcg tacagtactt ctctgttagg gagagttgga    1200
tccgccactt cagactggcg gaagaaccta gcctccctgg gtttgaagac ctcctcagaa    1260
taagggtaga gcctaatacg tcgccaatgg gtggcaaggg tgaaaaaatc ttccggtttg    1320
gcagtcacaa gtggtacggt gctggaaaga gagcaaggag agcacgctct ggtgcgactg    1380
ccacggtcgc tcaccgcgct tgcccgctc gcgaagccca gcaggccaag aagctcgagg    1440
ttgccagcgc aacagggct gagcatctca gtactattc cccgcctgcc gacgggaact    1500
gtggttggca ctgcatttcc gccattacca accggatggt gaattccaaa tttgaaacca    1560
ctcttcccga gagagtgaga ccttcagatg actgggctac tgacgaggat cttgtgaata    1620
ccatccaaat cctcaggctc cccgcggcct tggacaggaa cggtgcttgt gctgcgcca    1680
agtacgtgct caagctggaa ggtgagcact ggaccgtctc tgtgacccct gggatgaccc    1740
cttctttgct ccccccttgaa tgtgttcagg ttgttgtga gcataagagc ggtcttggtt    1800
tcccagacgt ggtcgaagtt tccggatttg accctgcctg tcttgaccga cttgctgaga    1860
taatgcactt gcctagcagt gtcatcccag ctgctctggc cgagatgtcc gacgacttca    1920
atcgtctggc ttccccggcc gccactgtgt ggactgtttc gcaattcttt gcccgccaca    1980
gaggaggaga gcatcctgac caggtgtgct tagggaaaat tatcaacctt gtcaggtga    2040
ttgaggaatg ctgctgttcc cggaacaaag ccaaccgggc taccccggaa gaggttgcgg    2100
caaaagttga ccagtacctc cgtggtgcag caagccttgg agaatgcttg gccaagcttg    2160
```

```
agagggctcg cccgccgagc gcgacggaca cctcctttga ttggaatgtt gtgcttcctg    2220
gggttgagac ggcgaatcag acaaccaaac agctccatgt caaccagtgc cgcgctctgg    2280
ttcctgtcgt gactcaagag ccttttggaca gagactcggt ccctctgacc gccttctcgc   2340
tgtccaattg ctactaccct gcacaaggtg acgaggtccg tcaccgtgag aggctaaact    2400
ccttgctctc taagttggag ggggttgttc gtgaggaata tgggctcacg ccaactggac    2460
ctggcccgcg acccgcactg ccgaacgggc tcgacgagct taaagaccag atggaggagg   2520
atctgctgaa attagtcaac gcccaggcaa cttcagaaat gatggcctgg gcagccgagc   2580
aggttgatct aaaagcttgg gtcaaaaatt acccacggtg gacaccgcca cccctccac    2640
caagagttca gcctcgaaaa acgaagtctg tcaagagctt gctagagaac aagcctgtcc   2700
ctgctccgcg caggaaggtc agatctgatt gtggcagccc gattttgatg ggcgacaatg   2760
ttcctaacgg ttgggaagat tcgactgttg gtggtcccct tgatctttcg gcaccatccg   2820
agccgatgac acctctgagt gagcctgtac ttatttccag gccagtgaca tctttgagtg   2880
tgccggcccc agttcctgca ccgcgtagag ctgtgtcccg accgatgacg ccctcgagtg   2940
agccaatttt tgtgtctgca ctgcgacaca aatttcagca ggtggaaaaa gcaaatctgg   3000
cggcagcagc gccgatgtgc caggacgaac ccttagattt gtctgcatcc tcacagactg   3060
aatatgaggc ttcccccctta acaccaccgc agaacgtggg cattctggag gtaagggggc   3120
aagaagctga ggaagttctg agtgaaatct cggatattct gaatgatacc aaccctgcac   3180
ctgtgtcatc aagcagctcc ctgtcaagtg ttaagatcac acgcccaaaa tactcagctc   3240
aagccattat cgactcgggc gggccctgca gtgggcacct ccaaagggaa aaagaagcat   3300
gcctccgcat catgcgtgaa gcttgtgatg cggccaagct tagtgaccct gccacgcagg   3360
aatggctttc tcgcatgtgg gatagggtgg acatgctgac ttggcgcaac acgtctgctt   3420
accaggcgtt tcgcacctta gatggcaggt ttgggtttct cccaaagatg atactcgaga   3480
cgccgccgcc ctaccgtgt gggttgtga tgttgcctca cacccctgca ccttccgtga    3540
gtgcagagag cgaccttacc attggttcag tcgccactga agatattcca cgcatcctcg   3600
ggaaaataga aaataccggt gagatgatca accaggacc cttggcatcc tctgaggaag    3660
aaccggtata caaccaacct gccaaagact cccggatatc gtcgcggggg tctgacgaga   3720
gcacagcagc tccgtccgcg ggtacaggtg gcgccggctt atttactgat ttgccaccttt   3780
cagacggcgt agatgcggac ggtgggggc cgttgcagac ggtaagaaag aaagctgaaa   3840
ggctcttcga ccaattgagc cgtcaggttt ttaacctcgt ctcccatctc cctgttttct   3900
tctcacacct cttcaaatct gacagtggtt attctccggg tgattggggt tttgcagctt   3960
ttactctatt ttgcctcttt ttgtgttaca gctacccatt cttcggtttc gttccctct   4020
tgggtgtatt ttctgggtct tctcggcgtg tgcgcatggg ggttttggc tgctggctgg    4080
cttttgctgt tggcctgttc aagcctgtgt ccgaccagt cggcactgct tgtgagtttg   4140
actcgccaga gtgcaggaac gtccttcatt cttttgagct tctcaaacct tgggaccctg   4200
ttcgcagcct tgttgtgggc cccgtcggtc tcggtcttgc cattcttggc aagttactgg   4260
gcggggcacg ctacatctgg cattttttgc ttaggcttgg cattgttgca gattgtatct   4320
tggctggagc ttatgtgctt tctcaaggta ggtgtaaaaa gtgctgggga tcttgtataa   4380
gaactgctcc taatgaaatc gccttcaacg tgttcccttt tacacgtgcg accaggtcgt   4440
cactcatcga cctgtgcgat cggttttgtg cgccaacagg catggacccc attttcctcg   4500
ccactgggtg gcgtgggtgc tggaccggcc gaagtcccat tgagcaaccc tctgaaaaac   4560
```

| | |
|---|---|
| ccatcgcgtt cgcccagttg gatgaaaaga ggattacggc tagaactgtg gtcgctcagc | 4620 |
| cttatgatcc taatcaagcc gtgaagtgct tgcgggtgtt acaggcgggt ggggcgatgg | 4680 |
| tggcccgaggc agtcccaaaa gtggccaaag tttctgctat tccattccga gccccttttt | 4740 |
| ttcccaccgg agtgaaagtt gatcccgagt gcaggatcgt ggttgacccc gatacttta | 4800 |
| ctacagccct ccggtctggt tactctacca caaacctcgt ccttggtgtg ggggactttg | 4860 |
| cccagctgaa tggactaaag atcaggcaaa tttccaagcc ttcgggagga ggcccacacc | 4920 |
| tcattgctgc cctgcatgtt gcctgctcga tggcgttgca catgcttgct ggggtttatg | 4980 |
| taacttcagt ggggtcttgc ggtgccggca ccaacgatcc atggtgcact aatccgtttg | 5040 |
| ccgttcctgg ctacggacca ggctctctct gcacgtccag attgtgcatc tcccaacatg | 5100 |
| gccttaccct gcccttgaca gcacttgtgg cgggattcgg tcttcaggaa atcgccttgg | 5160 |
| tcgttttgat tttcgtttcc atcggaggca tggctcatag gttgagttgt aaggctgata | 5220 |
| tgctgtgcat tttacttgca atcgccagct atgtttgggt acccctacc tggttgcttt | 5280 |
| gtgtgtttcc ttgttggttg cgctggttct cttttgcaccc ccttaccatc ctatggttgg | 5340 |
| tgttttctt gatttctgta aatatgcctt cgggaatctt ggccgtggtg ttattggttt | 5400 |
| ctctttggct tttgggacgt tatactaaca ttgctggtct tgtcaccccc tatgatattc | 5460 |
| atcattacac cagtggcccc cgcggtgttg ccgccttggc taccgcacca gatgggaacct | 5520 |
| acttggctgc cgtccgccgc gctgcgttga ctggtcgcac catgctgttc accccgtctc | 5580 |
| agcttgggtc ccttcttgag ggcgctttca gaactcgaaa gccctcactg aacaccgtca | 5640 |
| atgtggttgg gtcctccatg ggctctggtg gagtgttcac catcgacggg aaaattaggt | 5700 |
| gcgtgactgc cgcacatgtc cttacgggta attcggctag ggtttccgga gtcggcttca | 5760 |
| atcaaatgct tgactttgat gtgaaagggg acttcgccat agctgattgc ccgaattggc | 5820 |
| aaggagctgc tcccaagacc caattctgcg aggacggatg gactggccgt gcctattggc | 5880 |
| tgacatcctc tggcgtcgaa cccggtgtta ttgggaatgg attcgccttc tgcttcaccg | 5940 |
| cgtgcggcga ttccgggtcc ccagtgatca ccgaagctgg tgagattgtc ggcgttcaca | 6000 |
| caggatcaaa taaacaagga ggtggcatcg tcacgcgccc ttcaggccag ttttgtaacg | 6060 |
| tggcacccat caagctgagc gaattaagtg aattctttgc tggacccaag gtcccgctcg | 6120 |
| gtgatgtgaa ggttggcagc cacataatta agacacgtg cgaagtacct tcagatcttt | 6180 |
| gcgccttgct tgctgccaaa cctgaactgg agggaggcct ctccaccgtc caacttctgt | 6240 |
| gtgtgttttt cctactgtgg agaatgatgg gacatgcctg gacgcccttg gttgctgtgg | 6300 |
| ggttttttcat tctgaatgag gttctcccag ctgtcctggt tcggagtgtt ttctcctttg | 6360 |
| ggatgtttgt gctatcttgg ctcacaccat ggtctgcgca agttctgatg atcaggcttc | 6420 |
| taacagcagc tcttaacagg aacagatggt cacttgcctt ttacagcctt ggtgcggtga | 6480 |
| ccggttttgt cgcagatctt gcggtaactc aagggcaccc gttgcaggca gtaatgaatt | 6540 |
| tgagcaccta tgccttcctg cctcggatga tggttgtgac ctcaccagtc ccagtgattg | 6600 |
| cgtgtggtgt tgtgcacccta cttgccatca ttttgtactt gttcaagtac cgcggcctgc | 6660 |
| acaatgttct tgttggtgat ggagcgtttt ctgcagcttt cttcttgcga tactttgccg | 6720 |
| agggaaagtt gagggaaggg gtgtcgcaat cctgcggaat gaatcatgag tcattgactg | 6780 |
| gtgccctcgc tatgagactc aatgacgagg acttggactt cctacgaaa tggactgatt | 6840 |
| ttaagtgctt tgtttctgcg tccaacatga ggaatgcagc aggccaattc atcgaggctg | 6900 |

```
cctatgcaaa agcacttaga attgaacttg cccagttggt gcaggttgat aaggttcgag    6960
gtactttggc caagcttgag gcttttgctg ataccgtggc accccaactc tcgcccggtg    7020
acattgttgt tgctcttggc catacgcctg ttggcagcat cttcgaccta aaggttggtg    7080
gtaccaagca tactctccaa gtcattgaga ccagagtcct tgccgggtcc aaaatgaccg    7140
tggcgcgcgt cgttgaccca accccacgc ccccacccgc accgtgccc atcccctcc       7200
caccgaaagt tctagagaat ggtcccaacg cctgggggga tggggaccgt ttgaataaga    7260
agaagaggcg taggatggaa accgtcggca tctttgtcat gggtgggaag aagtaccaga    7320
aattttggga caagaattcc ggtgatgtgt tttacgagga ggtccatgac aacacagatg    7380
cgtgggagtg cctcagagtt ggtgaccctg ccgactttaa ccctgagaag ggaactctgt    7440
gtgggcatac tactattgaa gataaggatt acaaagtcta cgcctcccca tctggcaaga    7500
agttcctggt ccccgtcaac ccagagagcg gaagagccca tgggaagct gcaaagcttt     7560
ccgtggagca ggcccttggc atgatgaatg tcgacggtga actgacggcc aaagaagtgg    7620
agaaactgaa aagaataatt gacaaacttc agggccttac taaggagcag tgtttaaact    7680
gctagccgcc agcggcttga cccgctgtgg tcgcggcggc ttggttgtta ctgagacagc    7740
ggtaaaaata gtcaaatttc acaaccggac tttcacccta gggcctgtga atttaaaagt    7800
ggccagtgag gttgagctga aagacgcggt cgagcacaac caacacccgg ttgcaagacc    7860
ggttgacggt ggtgttgtgc tcctgcgttc cgcagttcct tcgcttatag atgtcctgat    7920
ctccggtgct gacgcatctc ctaagttact cgctcgtcac gggccgggga acactgggat    7980
cgatggcacg ctttgggact ttgaggccga ggccaccaaa gaggaaattg cgctcagtgc    8040
gcaaataata caggcttgtg acattaggcg cggtgacgca cctgaaattg gtctcccta    8100
caagctgtac cctgttaggg gcaacccga gcgggtaaaa ggagttttac agaatacaag    8160
gtttggagac ataccttaca aaaccccag tgacactggg agcccagtgc acgcggctgc    8220
ctgcctcacg cccaatgcca ctccggtgac tgatgggcgc tccgtcttgg ctactaccat    8280
gccctccggt tttgaattgt atgtaccgac cattccagcg tctgtccttg attatcttga    8340
ctctaggcct gactgcccca aacagttgac agagcacggc tgtgaggatg ccgcattgag    8400
agacctctcc aagtatgact tgtccaccca aggctttgtt ttacctgggg ttcttcgcct    8460
tgtgcgtaag tacctgtttg cccacgtggg taagtgcccg cccgttcatc ggccttccac    8520
ttaccctgcc aagaattcta tggctggaat aaatgggaac aggtttccaa ccaaggacat    8580
tcagagcgtc cccgaaatcg acgttctgtg cgcacaggcc gtgcgagaaa actggcaaac    8640
tgttacccct tgtaccctca agaaacagta ttgtgggaag aagaagacta ggacaatact    8700
cggcaccaat aatttcattg cgttggccca ccggcagcg ttgagtggtg tcacccaggg    8760
cttcatgaaa aaggcgttta actcgcccat cgccctcggg aaaaacaaat ttaaggagct    8820
acagactccg atcttaggca ggtgccttga agctgatctt gcatcctgtg atcgatccac    8880
acctgcaatt gtccgctggt ttgccgccaa ccttctttat gaacttgcct gtgctgaaga    8940
gcacctaccg tcgtacgtgc tgaactgctg ccatgaccta ttggtcacgc agtccggcgc    9000
agtgactaag aggggtggcc tgtcgtctgg cgacccgatc acttctgtgt ctaacaccat    9060
ttacagcttg gtgatatatg cacagcacat ggtgcttagt tactttaaaa gtggtcaccc    9120
tcatggcctt ctgttcctac aagaccagct gaagttcgag gacatgctca agtccaacc    9180
cctgatcgtc tattcggacg acctcgtgct gtatgccgaa tctcccacca tgccgaacta    9240
ccactggtgg gtcgaacatc tgaatttgat gctgggtttt cagacggacc caaagaagac    9300
```

```
agccataacg gactcgccat catttctagg ctgtaggata ataaatggac gccagctagt    9360
ccccaaccgt gacaggatcc tcgcggccct cgcttaccat atgaaggcaa acaatgtttc    9420
tgaatactac gccgcggcgg ctgcaatact catggacagc tgtgcttgtt tagagtatga    9480
tcctgaatgg tttgaagagc ttgtggttgg gatagcgcat tgcgcccgca aggacggcta    9540
cagctttccc ggcccgccgt tcttcttgtc catgtgggaa aaactcagat ccaatcatga    9600
ggggaagaag tccagaatgt gcgggtattg cggggccctg gctccgtacg ccactgcctg    9660
tggcctcgac gtctgtattt accacaccca cttccaccag cattgtccag tcacaatctg    9720
gtgtggccac ccggctggtt ctggttcttg tagtgagtgc aaaccccccc tagggaaagg    9780
cacaagccct ctagatgagg tgttagaaca agtcccgtat aagcctccac ggactgtaat    9840
catgcatgtg gagcagggtc tcacccctct tgacccaggc agataccaga ctcgccgcgg    9900
attagtctcc gttaggcgtg gcatcagagg aaatgaagtt gacctaccag acggtgatta    9960
tgctagcacc gccctactcc ccacttgtaa agagatcaac atggtcgctg tcgcctctaa   10020
tgtgttgcgc agcaggttca tcatcggtcc gcccggtgct gggaaaacat actggctcct   10080
tcagcaggtc caggatggtg atgtcattta cacaccgact caccagacca tgctcgacat   10140
gattagggct ttggggacgt gccggttcaa cgtcccagca ggtgcaacgc tgcaattccc   10200 tgcccctcc cgtaccggcc cgtgggttcg catcctagcc ggcggttggt gtcctggtaa   10260
gaattccttc ttggatgaag cagcgtattg taatcacctt gatgtcttga ggctccttag   10320
caaaaccacc ctcacctgtc tgggagactt caaacaactc cacccagtgg gttttgattc   10380
tcattgctat gtttttgaca tcatgcctca gacccagttg aagaccatct ggagattcgg   10440
acagaacatc tgtgatgcca tccaaccaga ttacagggac aaacttgtgt ccatggtcaa   10500
cacaacccgt gtaacccacg tggaaaaacc tgtcaagtat gggcaagtcc tcaccccta   10560 ccacagggac cgagaggacg gcgccatcac aattgactcc agtcaaggcg ccacatttga   10620
tgtggtcaca ctgcatttgc ccactaaaga ttcactcaac aggcaaagag cccttgttgc   10680
tatcaccagg gcaagacatg ctatctttgt gtatgaccca cacagcaat tgcagagcat   10740 gtttgatctt cctgcgaagg gcacacccgt caacctcgca gtgcaccgtg atgagcagct   10800
gatcgtactg gatagaaata ataaagaatg cacagttgct caggctctag caacggaga   10860 taaatttagg gccaccgaca agcgcgttgt agattctctc cgcgccattt gtgctgatct   10920
ggaagggtcg agctctccgc tccccaaggt cgcacacaac ttgggatttt atttctcacc   10980
tgatttgaca cagtttgcta aactcccggt agaccttgca ccccactggc ccgtggtgac   11040
aacccagaac aatgaaaagt ggccggatcg gctggttgcc agccttcgcc ctgtccataa   11100
gtatagccgt gcgtgcattg gtgccggcta tatggtgggc cctcggtgt ttctaggcac   11160 ccctggggtc gtgtcatact acctcacaaa atttgtcaag gcgaggctc aagtgcttcc   11220 ggagacagtc ttcagcaccg gccgaattga gtggattgc cggagtatc ttgatgacag   11280 ggagcgagaa gttgctgagt ccctcccaca tgccttcatt ggcgacgtca aaggcaccac   11340 cgttgggga tgtcatcatg tcacctccaa ataccttccg cgcttccttc ccaaggaatc   11400
agtcgcggta gtcgggggttt cgagcccgg gaaagccgca aaagcagtgt gcacattgac   11460
ggatgtgtac ctcccagacc ttgaggccta cctccaccca gagactcagt ccaagtgctg   11520
gaaagttatg ttggacttca aggaagttcg actgatggtc tggaaagaca agacggccta   11580
tttccaactt gaaggccgct atttcacctg gtatcagctt gcaagctacg cctcgtacat   11640
```

```
ccgtgttcct gtcaactcca cggtgtatct ggacccctgc atgggccctg cccttttgcaa   11700 cagaagagtt gtcgggtcca cccattgggg agctgacctc gcagtcaccc cttatgatta   11760
cggtgctaaa atcatcttgt ctagcgctta ccatggtgaa atgcctcctg gatacaagat   11820
tctggcgtgc gcggagttct cgctcgacga cccagtcaag tacaaacaca cctggggttt   11880
tgaatcggat acagcgtatc tgtatgagtt caccggaaac ggtgaggact gggaggatta   11940
caatgatgcg tttcgtgcgc gccagaaagg gaaaatttat aaggccactg ctaccagcat   12000
gaagttttat tttcccccgg gccccgtcat tgaaccaact ttaggcctga attgaaatga   12060
aatggggtct atacaaagcc tcttcgacaa aattggccag cttttttgtgg atgctttcac   12120 ggaatttttg gtgtccattg ttgatatcat catattttttg gccattttgt ttggcttcac   12180
catcgccggt tggctggtgg tcttttgcat cagattggtt tgctccgcgg tattccgtgc   12240
gcgccctgcc attcaccctg agcaattaca gaagatccta tgaggccttt ctttctcagt   12300
gccgggtgga cattcccacc tgggggggtaa acaccccttt ggggatgttt tggcaccata   12360
aggtgtcaac cctgattgat gaaatggtgt cgcgtcgaat gtaccgcgtc atggataaag   12420
cagggcaagc tgcctggaaa caggtggtga gcgaggctac gctgtctcgc attagtagtc   12480
tggatgtggt ggctcatttt caacatcttg ccgccattga agccgagacc tgtaaatatt   12540
tggcttctcg actgcccatg ctacacaacc tgcgcatgac agggtcaaat gtaaccatag   12600
tgtataatag cactttaaat caggtgtttg ctatttttcc aacccctggt tcccggccaa   12660
agcttcatga ttttcagcaa tggctaatag ctgtacattc ctccatattt tcctctgttg   12720
cagcttcttg tactcttttt gttgtgctgt ggttgcgggt tccaatgcta cgtactgttt   12780
ttggtttccg ctggttaggg gcaatttttc tttcgaactc atggtgaatt acacggtgtg   12840
tccaccttgc ctcacccgac aagcagccgc tgaggtcctt gaacccggta ggtctctttg   12900
gtgcaggata gggcatgacc gatgtgggga ggacgatcac gacgaactgg ggttcatggt   12960
tccgcctggc ctctccagcg aaagccactt gaccagtgtt tacgcctggt tggcgttcct   13020
gtccttcagc tacacggccc agttccatcc cgagatattt gggataggga acgtgagtga   13080
agtttatgtt gacatcaagc accaattcat ctgcgccgtt catgacgggc agaacaccac   13140
cttgcctcgc catgacaata tttcagccgt atttcagacc tactatcaac atcaggtcga   13200
cggcggcaat tggtttcacc tagaatggct gcgtcccttc ttttcctctt ggttggtttt   13260
aaatgtttcg tggtttctca ggcgttcgcc tgcaagccat gtttcagttc gagtctttca   13320
gacatcaaaa ccaacactac cgcagcatca ggctttgttg tcctccagga catcagctgc   13380
cttaggcatg gcgactcgtc cttttccgacg attcgcaaaa gctctcaatg ccgcacggcg   13440 ataggggacac ctgtgtatat caccatcaca gccaatgtga cagatgagaa ttacttacat   13500
tcttctgatc tcctcatgct ttcttcttgc ctttttctatg cttctgagat gagtgaaaag   13560
ggattcaagg tggtatttgg caatgtgtca ggcatcgtgg ctgtgtgtgt caactttacc   13620
agctacgtcc aacatgtcaa agagtttact caacgctcct tggtggtcga tcatgtgcgg   13680
ctgcttcatt tcatgacacc tgagaccatg aggtgggcaa ccgttttagc ctgtctttttt   13740 gccatcctac tggcaatttg aatgttcaag tatgttgggg aaatgcttga ccgcgggctg   13800
ttgctcgcga ttgctttctt tgtggtgtat cgtgccgttc tggtttgctg tgctcggcaa   13860
cgccaacagc agcagcagct ctcatttcca gttgatttat aacttgacgc tatgtgagct   13920
gaatggcaca gattggctgg cagaaaaatt tgattgggcg gtggagactt ttgtcatctt   13980
tcccgtgttg actcacattg tttcctattg tgcactcacc accagccatt tccttgacac   14040
```

-continued

```
agttggtctg gttactgtgt ccaccgccgg gttttatcac gggcggtatg tcttgagtag    14100
catctacgcg gtctgtgctc tggctgcgtt gatttgcttc gttattaggc ttgcgaagaa    14160
ctgcatgtcc tggcgctact cttgtaccag atataccaac ttccttctgg acactaaggg    14220
cagactctat cgttggcggt cgcccgttat catagaaaaa aggggtaagg ttgaggtcga    14280
aggtcatctg atcgacctca aaagagttgt gcttgatggt tccgtggcaa cccctttaac    14340
cagagtttca gcggaacaat ggggtcgtct ctagacgact tttgccatga tagcactgct    14400
ccacaaaagg tgcttttggc gttttccatt acctacacgc cagtaatgat atatgctcta    14460
aaggtaagtc gcggccgact gctagggctt ctgcaccttt tgatcttcct gaattgtgct    14520
tttaccttcg ggtacatgac attcgcgcac tttcagagca caaatagggt cgcgctcgct    14580
atgggagcag tagttgcact tctttgggg gtgtactcag ccatagaaac ctggaaattc    14640
atcacctcca gatgccgttt gtgcttgcta ggccgcaagt acattctggc ccctgcccac    14700
cacgtcgaaa gtgccgcggg ctttcatccg attgcggcaa atgataacca cgcatttgtc    14760
gtccggcgtc ccggctccat tacggttaac ggcacattgg tgcccgggtt gaaaagcctc    14820
gtgttgggtg gcagaaaagc tgttaaacag ggagtggtaa accttgtcaa atatgccaaa    14880
taacaacggc aagcagcaaa agaaaaagaa ggggaatggc cagccagtca accagctgtg    14940
ccagatgctg ggtaaaatca tcgcccagca aaaccagtcc agaggcaagg gaccgggcaa    15000
gaaaagtaag aagaaaaacc cggagaagcc ccattttcct ctagcgaccg aagatgacgt    15060
caggcatcac ttcaccctg gtgagcggca attgtgtctg tcgtcgatcc agactgcctt     15120
taaccagggc gctggaactt gtaccctgtc agattcaggg aggataagtt acactgtgga    15180
gtttagtttg ccgacgcatc atactgtgcg cctgatccgc gtcacagcat caccctcagc    15240
atgatgggct ggcattcttt aggcacctca gtgtcagaat tggaagaatg tgtggtggat    15300
ggcactgatt gacattgtgc ctctaagtca cctattcaat tagggcgacc gtgtgggggt    15360
aaaatttaat tggcgagaac catgcggccg caattaaaaa aaaaaaaaaa aaaaaaaaa     15420 aaaaaaaaaa aaaaaaaaaa aaaaaaaaa                                      15450
```

<210> SEQ ID NO 7
<211> LENGTH: 7
<212> TYPE: PRT
<213> ORGANISM: Artificial Sequence
<220> FEATURE:
<223> OTHER INFORMATION: genome position 735, ORF1a: 182, Nsp1b: 2,
      passage 0 amino acid

<400> SEQUENCE: 7

Ala Met Ala Asp Val Tyr Asp
1               5

<210> SEQ ID NO 8
<211> LENGTH: 7
<212> TYPE: PRT
<213> ORGANISM: Artificial Sequence
<220> FEATURE:
<223> OTHER INFORMATION: genome position 735, ORF1a: 182, Nsp1b: 2,
      passage 17 amino acid

<400> SEQUENCE: 8

Ala Met Ala Asn Val Tyr Asp
1               5

<210> SEQ ID NO 9

```
<211> LENGTH: 7
<212> TYPE: PRT
<213> ORGANISM: Artificial Sequence
<220> FEATURE:
<223> OTHER INFORMATION: genome position 735, ORF1a: 182, Nsp1b: 2,
      passage 52 amino acid

<400> SEQUENCE: 9

Ala Met Ala Asn Val Tyr Asp
1               5

<210> SEQ ID NO 10
<211> LENGTH: 7
<212> TYPE: PRT
<213> ORGANISM: Artificial Sequence
<220> FEATURE:
<223> OTHER INFORMATION: genome position 756, ORF1a: 189, Nsp1b: 9,
      passage 0 amino acid

<400> SEQUENCE: 10

Ile Ser His Asp Ala Val Met
1               5

<210> SEQ ID NO 11
<211> LENGTH: 7
<212> TYPE: PRT
<213> ORGANISM: Artificial Sequence
<220> FEATURE:
<223> OTHER INFORMATION: genome position 756, ORF1a: 189, Nsp1b: 9,
      passage 17 amino acid

<400> SEQUENCE: 11

Ile Gly His Asn Ala Val Met
1               5

<210> SEQ ID NO 12
<211> LENGTH: 7
<212> TYPE: PRT
<213> ORGANISM: Artificial Sequence
<220> FEATURE:
<223> OTHER INFORMATION: genome position 756, ORF1a: 189, Nsp1b: 9,
      passage 52 amino acid

<400> SEQUENCE: 12

Ile Gly His Asn Ala Val Met
1               5

<210> SEQ ID NO 13
<211> LENGTH: 7
<212> TYPE: PRT
<213> ORGANISM: Artificial Sequence
<220> FEATURE:
<223> OTHER INFORMATION: genome position 992, ORF1a: 267, Nsp1b: 87,
      passage 0 amino acid

<400> SEQUENCE: 13

Thr Val Pro Glu Gly Asn Cys
1               5

<210> SEQ ID NO 14
<211> LENGTH: 7
<212> TYPE: PRT
<213> ORGANISM: Artificial Sequence
<220> FEATURE:
<223> OTHER INFORMATION: genome position 992, ORF1a: 267, Nsp1b: 87,
      passage 17 amino acid

<400> SEQUENCE: 14
```

-continued

Thr Val Pro Asp Gly Asn Cys
1               5

<210> SEQ ID NO 15
<211> LENGTH: 7
<212> TYPE: PRT
<213> ORGANISM: Artificial Sequence
<220> FEATURE:
<223> OTHER INFORMATION: genome position 992, ORF1a: 267, Nsp1b: 87,
      passage 52 amino acid

<400> SEQUENCE: 15

Thr Val Pro Asp Gly Asn Cys
1               5

<210> SEQ ID NO 16
<211> LENGTH: 7
<212> TYPE: PRT
<213> ORGANISM: Artificial Sequence
<220> FEATURE:
<223> OTHER INFORMATION: genome position 1009, ORF1a: 273, Nsp1b: 93,
      passage 0 amino acid

<400> SEQUENCE: 16

Cys Trp Trp Cys Leu Phe Asp
1               5

<210> SEQ ID NO 17
<211> LENGTH: 7
<212> TYPE: PRT
<213> ORGANISM: Artificial Sequence
<220> FEATURE:
<223> OTHER INFORMATION: genome position 1009, ORF1a: 273, Nsp1b: 93,
      passage 17 amino acid

<400> SEQUENCE: 17

Cys Trp Trp Tyr Leu Phe Asp
1               5

<210> SEQ ID NO 18
<211> LENGTH: 7
<212> TYPE: PRT
<213> ORGANISM: Artificial Sequence
<220> FEATURE:
<223> OTHER INFORMATION: genome position 1009, ORF1a: 273, Nsp1b: 93,
      passage 52 amino acid

<400> SEQUENCE: 18

Cys Trp Trp Tyr Leu Phe Asp
1               5

<210> SEQ ID NO 19
<211> LENGTH: 7
<212> TYPE: PRT
<213> ORGANISM: Artificial Sequence
<220> FEATURE:
<223> OTHER INFORMATION: genome position 1096, ORF1a: 302, Nsp1b: 122,
      passage 0 amino acid

<400> SEQUENCE: 19

His Gly Val Pro Gly Lys Tyr
1               5

<210> SEQ ID NO 20
<211> LENGTH: 7
<212> TYPE: PRT
<213> ORGANISM: Artificial Sequence
<220> FEATURE:

<223> OTHER INFORMATION: genome position 1096, ORF1a: 302, Nsp1b: 122,
      passage 17 amino acid

<400> SEQUENCE: 20

His Gly Val His Gly Lys Tyr
1               5

<210> SEQ ID NO 21
<211> LENGTH: 7
<212> TYPE: PRT
<213> ORGANISM: Artificial Sequence
<220> FEATURE:
<223> OTHER INFORMATION: genome position 1096, ORF1a: 302, Nsp1b: 122,
      passage 52 amino acid

<400> SEQUENCE: 21

His Gly Val His Gly Lys Tyr
1               5

<210> SEQ ID NO 22
<211> LENGTH: 7
<212> TYPE: PRT
<213> ORGANISM: Artificial Sequence
<220> FEATURE:
<223> OTHER INFORMATION: genome position 2106, ORF1a: 639, Nsp2: 256,
      passage 0 amino acid

<400> SEQUENCE: 22

Ala Ala Lys Ile Asp Gln Tyr
1               5

<210> SEQ ID NO 23
<211> LENGTH: 7
<212> TYPE: PRT
<213> ORGANISM: Artificial Sequence
<220> FEATURE:
<223> OTHER INFORMATION: genome position 2106, ORF1a: 639, Nsp2: 256,
      passage 17 amino acid

<400> SEQUENCE: 23

Ala Ala Lys Val Asp Gln Tyr
1               5

<210> SEQ ID NO 24
<211> LENGTH: 7
<212> TYPE: PRT
<213> ORGANISM: Artificial Sequence
<220> FEATURE:
<223> OTHER INFORMATION: genome position 2106, ORF1a: 639, Nsp2: 256,
      passage 52 amino acid

<400> SEQUENCE: 24

Ala Ala Lys Val Asp Gln Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: genome position 2185, ORF1a: 665, Nsp2: 282,
      passage 0 amino acid

<400> SEQUENCE: 25

Pro Ser Ala Met Asp Thr Ser
1               5

```
<210> SEQ ID NO 26
<211> LENGTH: 7
<212> TYPE: PRT
<213> ORGANISM: Artificial Sequence
<220> FEATURE:
<223> OTHER INFORMATION: genome position 2185, ORF1a: 665, Nsp2: 282,
      passage 17 amino acid

<400> SEQUENCE: 26

Pro Ser Ala Thr Asp Thr Ser
1               5

<210> SEQ ID NO 27
<211> LENGTH: 7
<212> TYPE: PRT
<213> ORGANISM: Artificial Sequence
<220> FEATURE:
<223> OTHER INFORMATION: genome position 2185, ORF1a: 665, Nsp2: 282,
      passage 52 amino acid

<400> SEQUENCE: 27

Pro Ser Ala Thr Asp Thr Ser
1               5

<210> SEQ ID NO 28
<211> LENGTH: 7
<212> TYPE: PRT
<213> ORGANISM: Artificial Sequence
<220> FEATURE:
<223> OTHER INFORMATION: genome position 2403, ORF1a: 738, Nsp2: 355,
      passage 0 amino acid

<400> SEQUENCE: 28

Leu Val Ser Val Leu Ser Lys
1               5

<210> SEQ ID NO 29
<211> LENGTH: 7
<212> TYPE: PRT
<213> ORGANISM: Artificial Sequence
<220> FEATURE:
<223> OTHER INFORMATION: genome position 2403, ORF1a: 738, Nsp2: 355,
      passage 17 amino acid

<400> SEQUENCE: 29

Leu Asn Ser Leu Leu Ser Lys
1               5

<210> SEQ ID NO 30
<211> LENGTH: 7
<212> TYPE: PRT
<213> ORGANISM: Artificial Sequence
<220> FEATURE:
<223> OTHER INFORMATION: genome position 2403, ORF1a: 738, Nsp2: 355,
      passage 52 amino acid

<400> SEQUENCE: 30

Leu Asn Ser Leu Leu Ser Lys
1               5

<210> SEQ ID NO 31
<211> LENGTH: 7
<212> TYPE: PRT
<213> ORGANISM: Artificial Sequence
<220> FEATURE:
<223> OTHER INFORMATION: genome position 3019, ORF1a: 943, Nsp2: 560,
      passage 0 amino acid

<400> SEQUENCE: 31
```

```
Ala Pro Met Tyr Gln Asp Glu
1               5

<210> SEQ ID NO 32
<211> LENGTH: 7
<212> TYPE: PRT
<213> ORGANISM: Artificial Sequence
<220> FEATURE:
<223> OTHER INFORMATION: genome position 3019, ORF1a: 943, Nsp2: 560,
      passage 17 amino acid

<400> SEQUENCE: 32

Ala Pro Met Cys Gln Asp Glu
1               5

<210> SEQ ID NO 33
<211> LENGTH: 7
<212> TYPE: PRT
<213> ORGANISM: Artificial Sequence
<220> FEATURE:
<223> OTHER INFORMATION: genome position 3019, ORF1a: 943, Nsp2: 560,
      passage 52 amino acid

<400> SEQUENCE: 33

Ala Pro Met Cys Gln Asp Glu
1               5

<210> SEQ ID NO 34
<211> LENGTH: 7
<212> TYPE: PRT
<213> ORGANISM: Artificial Sequence
<220> FEATURE:
<223> OTHER INFORMATION: genome position 4477, ORF1a: 1429, Nsp3: 72,
      passage 0 amino acid

<400> SEQUENCE: 34

Cys Ala Pro Lys Gly Met Asp
1               5

<210> SEQ ID NO 35
<211> LENGTH: 7
<212> TYPE: PRT
<213> ORGANISM: Artificial Sequence
<220> FEATURE:
<223> OTHER INFORMATION: genome position 4477, ORF1a: 1429, Nsp3: 72,
      passage 17 amino acid

<400> SEQUENCE: 35

Cys Ala Pro Thr Gly Met Asp
1               5

<210> SEQ ID NO 36
<211> LENGTH: 7
<212> TYPE: PRT
<213> ORGANISM: Artificial Sequence
<220> FEATURE:
<223> OTHER INFORMATION: genome position 4477, ORF1a: 1429, Nsp3: 72,
      passage 52 amino acid

<400> SEQUENCE: 36

Cys Ala Pro Thr Gly Met Asp
1               5

<210> SEQ ID NO 37
<211> LENGTH: 7
<212> TYPE: PRT
<213> ORGANISM: Artificial Sequence
```

<220> FEATURE:
<223> OTHER INFORMATION: genome position 4705, ORF1a: 1505, Nsp3: 148,
      passage 0 amino acid

<400> SEQUENCE: 37

Pro Lys Val Val Lys Val Ser
1               5

<210> SEQ ID NO 38
<211> LENGTH: 7
<212> TYPE: PRT
<213> ORGANISM: Artificial Sequence
<220> FEATURE:
<223> OTHER INFORMATION: genome position 4705, ORF1a: 1505, Nsp3: 148,
      passage 17 amino acid

<400> SEQUENCE: 38

Pro Lys Val Ala Lys Val Ser
1               5

<210> SEQ ID NO 39
<211> LENGTH: 7
<212> TYPE: PRT
<213> ORGANISM: Artificial Sequence
<220> FEATURE:
<223> OTHER INFORMATION: genome position 4705, ORF1a: 1505, Nsp3: 148,
      passage 52 amino acid

<400> SEQUENCE: 39

Pro Lys Val Ala Lys Val Ser
1               5

<210> SEQ ID NO 40
<211> LENGTH: 7
<212> TYPE: PRT
<213> ORGANISM: Artificial Sequence
<220> FEATURE:
<223> OTHER INFORMATION: genome position 5985, ORF1a: 1932, Nsp4: 129,
      passage 0 amino acid

<400> SEQUENCE: 40

Ala Gly Glu Leu Val Gly Val
1               5

<210> SEQ ID NO 41
<211> LENGTH: 7
<212> TYPE: PRT
<213> ORGANISM: Artificial Sequence
<220> FEATURE:
<223> OTHER INFORMATION: genome position 5985, ORF1a: 1932, Nsp4: 129,
      passage 17 amino acid

<400> SEQUENCE: 41

Ala Gly Glu Ile Val Gly Val
1               5

<210> SEQ ID NO 42
<211> LENGTH: 7
<212> TYPE: PRT
<213> ORGANISM: Artificial Sequence
<220> FEATURE:
<223> OTHER INFORMATION: genome position 5985, ORF1a: 1932, Nsp4: 129,
      passage 52 amino acid

<400> SEQUENCE: 42

Ala Gly Glu Ile Val Gly Val
1               5

<210> SEQ ID NO 43
<211> LENGTH: 7
<212> TYPE: PRT
<213> ORGANISM: Artificial Sequence
<220> FEATURE:
<223> OTHER INFORMATION: genome position 7419, ORF1a: 2410, Nsp7: 217, passage 0 amino acid

<400> SEQUENCE: 43

Ala Asp Phe Asp Pro Glu Lys
1               5

<210> SEQ ID NO 44
<211> LENGTH: 7
<212> TYPE: PRT
<213> ORGANISM: Artificial Sequence
<220> FEATURE:
<223> OTHER INFORMATION: genome position 7419, ORF1a: 2410, Nsp7: 217, passage 17 amino acid

<400> SEQUENCE: 44

Ala Asp Phe Asn Pro Glu Lys
1               5

<210> SEQ ID NO 45
<211> LENGTH: 7
<212> TYPE: PRT
<213> ORGANISM: Artificial Sequence
<220> FEATURE:
<223> OTHER INFORMATION: genome position 7419, ORF1a: 2410, Nsp7: 217, passage 52 amino acid

<400> SEQUENCE: 45

Ala Asp Phe Asn Pro Glu Lys
1               5

<210> SEQ ID NO 46
<211> LENGTH: 7
<212> TYPE: PRT
<213> ORGANISM: Artificial Sequence
<220> FEATURE:
<223> OTHER INFORMATION: genome position 8831, ORF1a/1b: 2881, Nsp9: 429, passage 0 amino acid

<400> SEQUENCE: 46

Gln Thr Pro Val Leu Gly Arg
1               5

<210> SEQ ID NO 47
<211> LENGTH: 7
<212> TYPE: PRT
<213> ORGANISM: Artificial Sequence
<220> FEATURE:
<223> OTHER INFORMATION: genome position 8831, ORF1a/1b: 2881, Nsp9: 429, passage 17 amino acid

<400> SEQUENCE: 47

Gln Thr Pro Ile Leu Gly Arg
1               5

<210> SEQ ID NO 48
<211> LENGTH: 7
<212> TYPE: PRT
<213> ORGANISM: Artificial Sequence
<220> FEATURE:
<223> OTHER INFORMATION: genome position 8831, ORF1a/1b: 2881, Nsp9: 429, passage 52 amino acid -continued

```
<400> SEQUENCE: 48

Gln Thr Pro Ile Leu Gly Arg
1               5

<210> SEQ ID NO 49
<211> LENGTH: 7
<212> TYPE: PRT
<213> ORGANISM: Artificial Sequence
<220> FEATURE:
<223> OTHER INFORMATION: genome position 13,857, ORF5: 29, passage 0
      amino acid

<400> SEQUENCE: 49

Ala Val Leu Val Asn Ala Asn
1               5

<210> SEQ ID NO 50
<211> LENGTH: 7
<212> TYPE: PRT
<213> ORGANISM: Artificial Sequence
<220> FEATURE:
<223> OTHER INFORMATION: genome position 13,857, ORF5: 29, passage 17
      amino acid

<400> SEQUENCE: 50

Ala Val Leu Gly Asn Ala Asn
1               5

<210> SEQ ID NO 51
<211> LENGTH: 7
<212> TYPE: PRT
<213> ORGANISM: Artificial Sequence
<220> FEATURE:
<223> OTHER INFORMATION: genome position 13,857, ORF5: 29, passage 52
      amino acid

<400> SEQUENCE: 51

Ala Val Leu Gly Asn Ala Asn
1               5

<210> SEQ ID NO 52
<211> LENGTH: 7
<212> TYPE: PRT
<213> ORGANISM: Artificial Sequence
<220> FEATURE:
<223> OTHER INFORMATION: genome position 14,578, ORF6: 74, passage 0
      amino acid

<400> SEQUENCE: 52

Val Ala Leu Thr Met Gly Ala
1               5

<210> SEQ ID NO 53
<211> LENGTH: 7
<212> TYPE: PRT
<213> ORGANISM: Artificial Sequence
<220> FEATURE:
<223> OTHER INFORMATION: genome position 14,578, ORF6: 74, passage 17
      amino acid

<400> SEQUENCE: 53

Val Ala Leu Ala Met Gly Ala
1               5

<210> SEQ ID NO 54
<211> LENGTH: 7
<212> TYPE: PRT
```

```
<213> ORGANISM: Artificial Sequence
<220> FEATURE:
<223> OTHER INFORMATION: genome position 14,578, ORF6: 74, passage 52
      amino acid

<400> SEQUENCE: 54

Val Ala Leu Ala Met Gly Ala
1               5

<210> SEQ ID NO 55
<211> LENGTH: 7
<212> TYPE: PRT
<213> ORGANISM: Artificial Sequence
<220> FEATURE:
<223> OTHER INFORMATION: genome position 14,780, ORF6: 141, passage 0
      amino acid

<400> SEQUENCE: 55

Pro Gly Ser Thr Thr Val Asn
1               5

<210> SEQ ID NO 56
<211> LENGTH: 7
<212> TYPE: PRT
<213> ORGANISM: Artificial Sequence
<220> FEATURE:
<223> OTHER INFORMATION: genome position 14,780, ORF6: 141, passage 17
      amino acid

<400> SEQUENCE: 56

Pro Gly Ser Ile Thr Val Asn
1               5

<210> SEQ ID NO 57
<211> LENGTH: 7
<212> TYPE: PRT
<213> ORGANISM: Artificial Sequence
<220> FEATURE:
<223> OTHER INFORMATION: genome position 14,780, ORF6: 141, passage 52
      amino acid

<400> SEQUENCE: 57

Pro Gly Ser Ile Thr Val Asn
1               5

<210> SEQ ID NO 58
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 58
gcagagctcg ttaattaaac cgtc                                          24

<210> SEQ ID NO 59
<211> LENGTH: 83
<212> TYPE: DNA
<213> ORGANISM: Artificial Sequence
<220> FEATURE:
<223> OTHER INFORMATION: oligonucleotide primer

<400> SEQUENCE: 59
aaaaaaaaaa aaaaaaaaaa atgcatattt aaatcccaag ccgaattcca gcacactggc   60
ggccgttact agtgagcggc cgc                                           83
```